United States Patent [19]

Matteucci et al.

[11] Patent Number: 5,434,257
[45] Date of Patent: Jul. 18, 1995

[54] BINDING COMPENTENT OLIGOMERS CONTAINING UNSATURATED 3′,5′ AND 2′,5′ LINKAGES

[75] Inventors: Mark D. Matteucci, Burlingame; Xiaodong Cao, Carlsbad, both of Calif.

[73] Assignee: Gilead Sciences, Inc., Foster City, Calif.

[21] Appl. No.: 142,785

[22] Filed: Oct. 26, 1993

Related U.S. Application Data

[63] Continuation-in-part of Ser. No. 892,902, Jun. 1, 1992.
[51] Int. Cl.$^6$ .................... C07H 19/00; C07H 21/00
[52] U.S. Cl. .................... 536/24.3; 536/23.1; 536/24.33; 536/24.5; 536/25.3; 536/25.1; 536/25.2
[58] Field of Search .................... 536/22.1, 23.1, 24.3, 536/24.33, 24.5, 25.1, 25.2, 25.3; 514/43, 44; 424/9

[56] References Cited

U.S. PATENT DOCUMENTS 5,034,506 7/1991 Summerton et al. ............... 528/391
5,079,151 1/1992 Lampson et al. ...................... 435/91

FOREIGN PATENT DOCUMENTS

WO86/05518 9/1986 WIPO .
WO89/05358 6/1989 WIPO ............................ C12Q 1/68
WO89/12060 12/1989 WIPO .
WO90/15065 12/1990 WIPO ............................ C07H 21/00
WO91/14436 10/1991 WIPO .
WO91/15500 10/1991 WIPO .
WO92/20822 11/1992 WIPO .

OTHER PUBLICATIONS

Agarwal et al., "Synthesis and enzymatic properties of deoxyribooligonucleotides containing methyl and phenylphosphonate linkages," Nucl. Acids. Res. 6:3009–3024 (1979).
Agrawal et al., "Oligodeoxynucleoside phosphoramidates and phosphoramidates as inhibitors of human immunodeficiency virus," Proc. Natl. Acad. Sci. 85:7079–7083 (1988).
Asseline et al., "Nucleic acid–binding molecules with high affinity and base sequence specificity: Intercalating agents covalently linked to oligodeoxynucleotides," Proc. Natl. Acad. Sci. 81:3297–3301 (1984).
Coull et al., "Synthesis and Characterization of a Carbamate–Linked Oligonucleoside," Tet. Lett. 28:745–748 (1987).
Inoue et al., "Synthesis and hybridization of dodecadeoxyribocucleotides containing a fluorescent pyridopyrimidine deoxynucleoside," Nuc. Acids Res. 13:7119–7128 (1985).
Kierzek et al., "Association of 2′–5′ oligoribonucleotides," Nuc. Acids. Rs. 20(7):1685–1690 (1992).
Letsinger et al., "Cationic Oligonucleotides," J. Am. Chem. Soc. 110:4470–4471 (1988).
Stein et al., "Oligodeoxynucleotides as Inhibitors of Gene Expression: A Review," Cancer Res. 48:2659–2668 (1988).
Stirchak et al., "Uncharged Stereoregular Nucleic Acid Analogues. 1. Synthesis of a Cytosine–Containing Oligomer with Carbamate Internucleoside Linkages," J. Org. Chem. 52:4202–4206 (1987).
Uhlmann et al., "Antisense Oligonucleotides: A New Therapeutic Principle," Chem. Rev. 90:543–584 (1990).
Young et al., "Triple helix formation inhibits transcription elongation in vitro," Proc. Natl. Acad. Sci. 88:10023–10026 (1991).
Agrawal et al., "Oligodeoxynucleoside Methylphosphonates: Synthesis and Enzymic Degradation," TET LETT 28:3539–3542 (1987).
Lin et al., "Hybridization properties of deoxyoligonucleotides containing antraquinone pseudonucelosides," Nuc Acids Res 19(11):3111–3114 (1991).

Primary Examiner—Suzanne E. Ziska
Assistant Examiner—Bruce Campbell
Attorney, Agent, or Firm—Daryl D. Muenchau

[57] ABSTRACT

Oligonucleotide analogs having one or more substitute linkages of the formula 2′/3′—S—$CH_2$—CH=5′ or 2′/3′—O—$CH_2$—CH=5′ between adjacent nucleomonomers are disclosed. The substitute linkage replace the usual phosphodiester linkage found in unmodified nucleic acids. The oligonucleotide analogs are easy to synthesize, stable in vivo, resistant to endogenous nucleases and are able to hybridize to target nucleic acid sequences in a sequence specific manner.

9 Claims, 47 Drawing Sheets a: X=F Y=H
b: X=H Y=F a: X=H  Y=F
b: X=F  Y=H

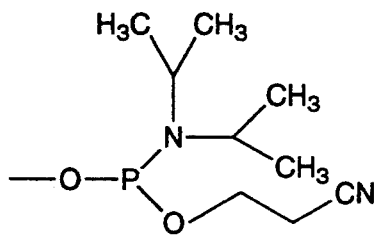
N,N-diisopropylamino-β-cyanoethoxyphosphine
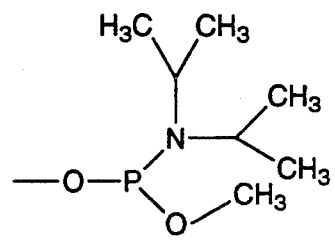
N,N-diisopropylamino-methoxyphosphine
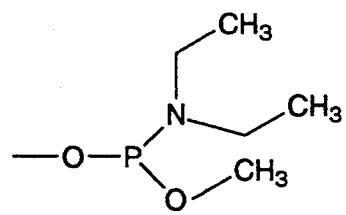
N,N-diethylamino-methoxyphosphine
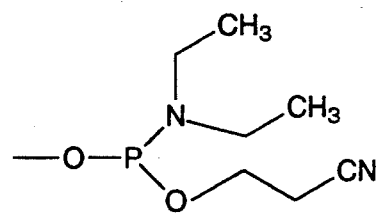
N,N-diethylamino-β-cyanoethoxy phosphine
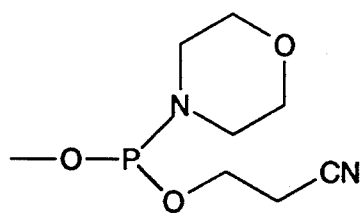
N-morpholino-β-cyanoethoxyphosphine
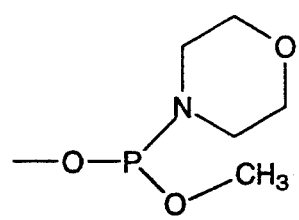
N-morpholino methoxyphosphine
Figure 26A-1

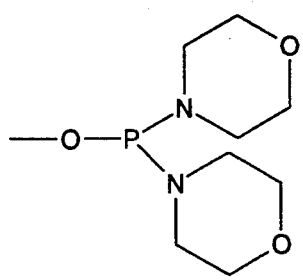
Bis morpholino-phosphine
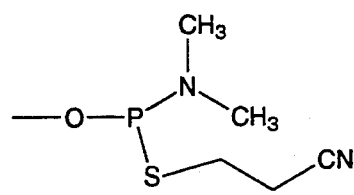
N,N-dimethylamino-β-cyanoethylmercapto-phosphine
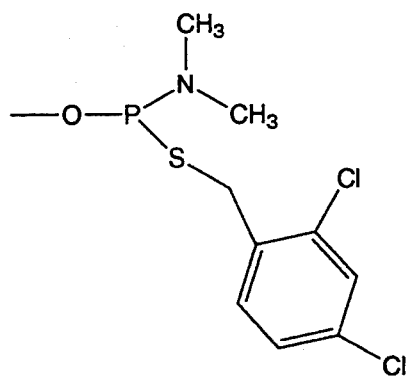
N,N-dimethylamino-2,4-dichlorobenzylmercapto-phosphine
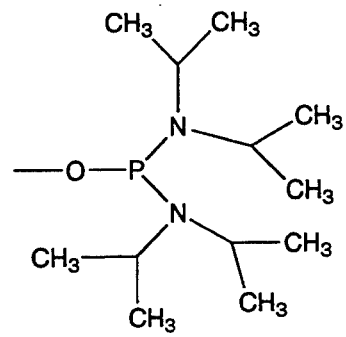
Bis(N,N-diisopropylamino)-phosphine
Figure 26A-2

A: Ac₂O/Pyridine;
B: 2-mesitylsulfonyl chloride/
4-dimethylaminopyridine/TEA/CH₂Cl₂;
C: corresponding 2-aminophenol; DBU
D: NH₃/CH₃OH E: 10 eq. KF/ethanol, refluxed;
F: DMT-Cl/Pyridine
G: PA

BINDING COMPENTENT OLIGOMERS CONTAINING UNSATURATED 3',5' AND 2',5' LINKAGES

This is a continuation-in-part of U.S.Ser. No. 07/892,902, filed Jun. 1, 1992, and pending.

BACKGROUND OF THE INVENTION

This invention relates to new oligonucleotide analogs. In particular, it relates to oligonucleotide analogs that have new substitute linkages in place of one or more of the phosphodiester linkages found in native DNA or RNA. Methods to synthesize the oligomers are described along with methods to use the oligomers as diagnostic reagents, or probes.

The use of oligomers (oligonucleotides and oligonucleotide analogs) as diagnostic reagents and probes is based on their ability to form duplex or triplex structures with complementary base sequences in target nucleic acids. Oligomers have also been used to inhibit gene expression by sequence-specific binding to target RNA sequences, "antisense inhibition", in living cells (for example see: Wagner et al, *Science* (1993) 260:1510–1513; Woolf et al, *Nucleic Acid Res* (1990) 18:1763–1769). In these studies, oligomers were introduced into cells using means such as microinjection or transfection to enhance the intracellular oligomer concentration. Antisense inhibition of gene expression using oligomers has been extensively described (Milligan et al, *J Med Chem* (1993) 36:1923–1937; Uhlmann et al, *Chem Reviews* (1990) 90:543–584; and Stein et al, *Cancer Res* (1988) 48:2659–2668). Another approach, referred to herein as "triple helix" therapy utilizes oligomers that bind to duplex DNA in a sequence-specific manner via "Hoogsteen" base pairing (Beal et al, *Science* (1991) 251:1360–1363; Young et al, *Proc Natl Acad Sci* (1991) 88:10023–10026). Both antisense and triple helix therapies exert therapeutic effects via binding to nucleic acid sequences that are responsible for establishing or maintaining disease conditions. Such sequences are found in the genome of pathogenic organisms including bacteria, protozoa, yeasts, parasites, fungi or viruses or may be endogenous sequences (oncogenes). By modulating the expression of a gene important for establishment, maintenance or elimination of a disease condition, the corresponding condition may be cured, prevented or ameliorated.

Another therapeutic approach that is based on the use of oligomers includes generation of "aptamers", oligomers that bind to intracellular or extracellular target molecules such as polypeptides or enzymes thereby interfering with their function (Bock, et al, *Nature* (1992) 355:564–566; PCT/US92/01383). Aptamers have successfully blocked target protein function in vivo (Griffin, et al, *Blood* (1993) 81:3271–3276). The use of oligomers for other therapeutic applications has been described (PCT/US91/01822). The invention oligomers can thus be used in applications where base pairing competence is not needed.

An important feature of oligomers is the type of backbone or linkage between adjacent nucleomonomers (nucleotides, nucleosides or their analogs) in an oligomer. Specifically, the backbone should contain internucleoside linkages that are stable in vivo and should be structured such that the oligomer is resistant to endogenous nucleases. At the same time, the oligomer must also retain its ability to hybridize to the target DNA or RNA.

A need exists for oligomers that are easy to synthesize, that are nuclease resistant, or have other useful properties such as improved permeation into cells.

It is an object of this invention to provide oligomers with substitute linkages that are easy to synthesize and that retain their ability to hybridize to complementary nucleic acid sequences.

These and other objects of the invention will be apparent from consideration of the specification as a whole.

SUMMARY OF THE INVENTION

The present invention is based on the construction of oligomers containing novel substitute linkages which substitute linkages are also referred to as allyl ether and allyl sulfide substitute linkages. Such linkages comprise substitution, for one or more linkages between adjacent nucleomonomers a linkage between the 2' and 5' or the 3' and 5' position of adjacent nucleomonomers. The substitute linkages comprise a three atom long substitute linkage of the formula 2'/3'—S—CH$_2$—CH=5' or 2'/3'-O-CH$_2$CH=5' wherein a double bond is located between the 5' carbon atom and the adjacent substitute linkage atom (i.e., the carbon atom of —CH=). These oligonucleotides are easy to synthesize, stable in vivo, resistant to endogenous nucleases and are able to hybridize to target nucleic acid sequences.

In another embodiment, the invention is directed to an oligomer of the formula I or Ia:

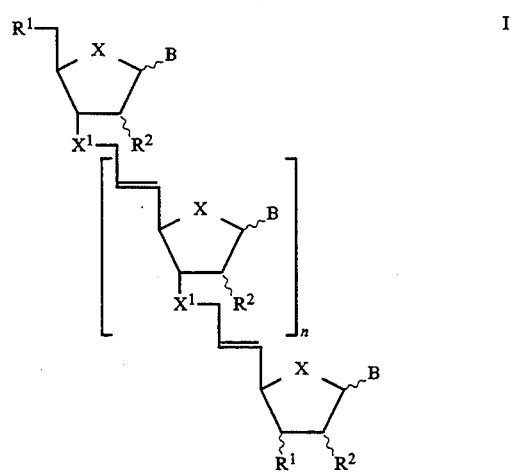

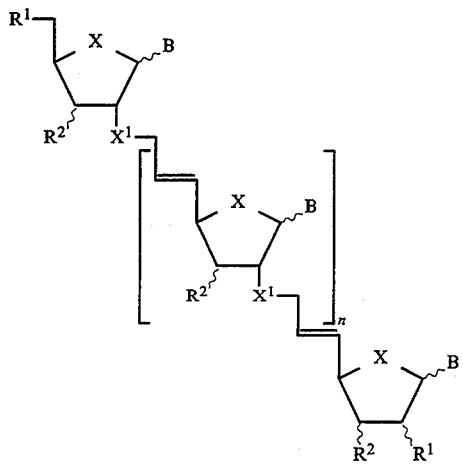

where X is S, O, $CH_2$, CHF or $CF_2$; $X^1$ is O or S; $R^1$ is independently H, an oligomer or a blocking group including $PO_3^{-2}$, O-dimethoxytrityl (DMTO), O-monomethoxytrityl (MMTO), H-phosphonate ($OPO_2H$), methylphosphonate ($OPO_3CH_3$), methylphosphonamidite, or a phosphoramidite such as β-cyanoethylphosphoramidite; $R^2$ independently is -O-alkyl ($C_1$–$C_{12}$ including O-methyl, O-ethyl, O-propyl, O-butyl and their isomers),-S-alkyl($C_1$–$C_{12}$), H, OH, $OCH_3$, $SCH_3$, $OCH_2CHCH_2$ (O-allyl), $OC_3C_7$ (O-propyl), $SCH_2CHCH_2$, or a halogen (F, Cl, Br or I); B is independently a base, and n is 0–100, preferably 0–28. Both $R^1$ taken together can comprise a circular oligomer and may be covalently linked, for example, at a terminal 5' position with a terminal 2' or 3' position.

In preferred embodiments structure I or Ia is an oligomer having uniform polarity although, circular or branched oligomers may be obtained, where $R^1$ is an oligomer which are useful in oligonucleotide based therapies or diagnostic applications.

BRIEF DESCRIPTION OF THE FIGURES

FIGS. 1 through 39 are depictions of chemical reaction sequences usable for synthesizing internucleoside linkages.

FIG. 1 shows the synthesis of a three atom long linkage with a nitrogen at the 5' end. FIG. 2 shows the synthesis of a three atom long linkage with a nitrogen at the 2' end. FIG. 3 depicts the synthesis of a three atom long linkage with a nitrogen in the middle. FIG. 4 depicts the formation of a four atom long linkage with oxygen at the 2' end and nitrogen at the 5' end. FIG. 5 shows the formation of a four atom long linkage with nitrogen at the 2' end and oxygen at the 5' end. FIG. 6 depicts the formation of a two atom long linkage with nitrogen at the 5' end. FIG. 7 shows the formation of a two atom long linkage with nitrogen at the 2' end. FIG. 8 shows the formation of three different three atom long linkages with sulfur at the 2' end. FIG. 9 depicts the formation of three different two atom long linkages with sulfur at the 2' end. FIG. 10 shows the synthesis of three different two atom long linkages with sulfur at the 5' end. FIG. 11 depicts the synthesis of a two atom long linkage with oxygen at the 2' end. FIG. 12 depicts the formation of a three atom long linkage with oxygen at the 5' end. FIG. 13 shows the formation of several three atom long linkages with derivatized nitrogen at the 2' end. FIG. 14 shows the synthesis of a three atom long linkage containing nitrogen at the 2' end and oxygen at the 5' end. FIG. 15 shows the formation of a three atom long linkage with sulfur at the 2' end. FIG. 16 shows the formation of a three atom linkage having a nitrogen atom at the 2' end and an oxygen-bearing carbon atom at mid-linkage and oxygen at the 5' end. FIG. 17 shows the formation of a three atom linkage having an oxygen atom at the 2' end and an oxygen-bearing carbon atom at mid linkage and nitrogen at the 5' end and also a linkage having an oxygen at the 2' end and a sulfur at the 5' end and a carbon midlinkage. FIGS. 18 and 19 show the formation of certain feedstocks such as compound 1 in FIG. 1 and compound 10 in FIG. 2 suitable for synthesis of the desired oligomers of this invention. FIG. 20 shows the formation of a three atom formacetal linkage. FIG. 21 shows the synthesis of a xylosofluoro monomer synthon. FIG. 22 shows the synthesis of a ribofluoro monomer synthon. FIG. 23 shows the formation of a three atom 2', 5'-thioformacetal linkage using xylosofluoro and ribofluoro monomers. FIG. 24 shows the formation of a three atom 2',5' formacetal linkage using xylosofluoro and ribofluoro monomers. FIG. 25 shows the formation of a three atom 2',5' thioformacetal linkage. FIG. 26A-1 shows structures of coupling groups used for linkage of nucleomonomers linked via phosphorous containing linkages. FIG. 26A-2 shows structures of coupling groups used for linkage of nucleomonomers linked via phosphorous containing linkages. FIG. 27 shows synthesis of a nucleomonomer used to synthesize substitute linkages containing a double bond. FIG. 28A-1 shows synthesis of an intermediate in the synthesis of a dimer linked by a three atom substitute linkage having sulfur at the 2' position and a double bond. FIG. 28A-2 shows synthesis of a dimer linked by a three atom substitute linkage having sulfur at the 2' position and a double bond. FIG. 29A-1 shows synthesis of an intermediate in the synthesis of a dimer linked by a three atom substitute linkage having oxygen at the 2' position and a double bond. FIG. 29A-2 shows synthesis of a dimer linked by a three atom substitute linkage having oxygen at the 2' position and a double bond. FIG. 30A-1 shows synthesis of an allyl bromide monomer. FIG. 30A-2 shows synthesis of 3',5' linked dimers having an unsaturated three atom substitute linkage having oxygen or sulfur at the 3' position and a double bond. FIGS. 30A-3 and 30A-4 show synthesis of a 3',5' linked dimer having a three atom substitute linkage with sulfur at the 3' position. FIG. 31 shows synthesis of a diazine tricyclic cytosine nucleomonomer. FIG. 32 shows synthesis of a triazine tricyclic cytosine nucleomonomer. FIG. 33 shows synthesis of a 2-pyridone tricyclic cytosine nucleomonomer. FIG. 34 shows synthesis of a 4-pyridone tricyclic cytosine nucleomonomer. FIG. 35 shows synthesis of a phenopyrroline tricyclic cytosine nucleomonomer. FIG. 36 shows synthesis of a pyridinopyrroline tricyclic cytosine nucleomonomer. FIG. 37 shows synthesis of a phenothiazine and phenoxazine tricyclic cytosine nucleomonomer. FIG. 38A-1 shows synthesis of a phenoxazine tricyclic cytosine nucleomonomer. FIG. 38A-2 shows synthesis of a phenoxazine tricyclic cytosine nucleomonomer. FIG. 39A-1 shows synthesis of an oligomer containing formula IX bases. FIG. 39A-3 shows synthesis of an oligomer containing formula IX bases. FIG. 39A-3 shows synthesis of an oligomer containing formula IX bases.

Figure 1:
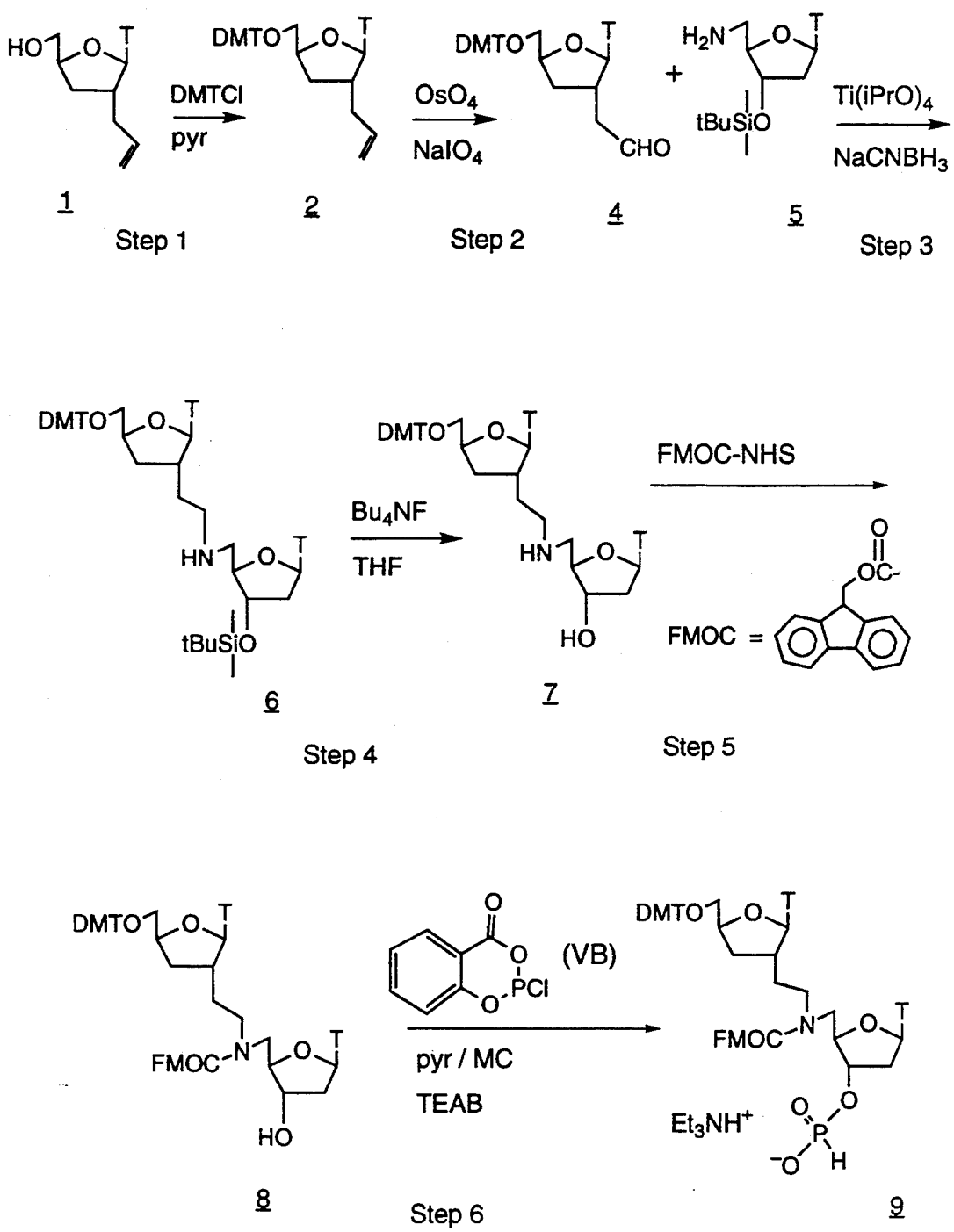

Structural Formulas.

Structural formulas described herein are designated as roman numerals (I, II, etc) and chemical compounds are designated a numeral (1, 2, etc).

DETAILED DESCRIPTION OF THE INVENTION

The practice of the present invention will employ, unless otherwise indicated, conventional techniques of chemistry, molecular biology, biochemistry, protein chemistry, and recombinant DNA technology, which are within the skill of the art. Such techniques are explained in the literature. See, e.g., Oligonucleotide Synthesis (M.J. Gait ed. 1984); Nucleic Acid Hybridization (B.D. Hames & S.J. Higgins eds. 1984); Sambrook, Fritsch & Maniatis, Molecular Cloning: A Laboratory Manual, Second Edition (1989); and the series *Methods in Enzymology* (S. Colowick and N. Kaplan eds., Academic Press, Inc.).

Nucleomonomer.

As used herein, the term "nucleomonomer" means a moiety comprising (1) a base covalently linked to (2) a second moiety. Nucleomonomers include nucleosides and nucleotides. Nucleomonomers can be linked to form oligomers that bind to target or complementary base sequences in nucleic acids in a sequence specific manner.

A "second moiety" as used herein includes a sugar moiety, usually a pentose, and those species which contain modifications of the sugar moiety, for example, wherein one or more of the hydroxyl groups are replaced with a halogen (Cl, Br, F, I), a heteroatom (including N, S and O), an aliphatic group, or are functionalized as ethers, amines, thiols, and the like. The pentose moiety can be replaced by a hexose or an alternate structure such as a cyclopentane ring, a 6-member morpholino ring and the like. Nucleomonomers as defined herein are also intended to include a base linked to an amino acid and/or an amino acid analog having a free carboxyl group and/or a free amino group and/or protected forms thereof.

Base.

"Base" as used herein includes those moieties which contain not only the known purine and pyrimidine heterocycles, but also heterocycle analogs and tautomers thereof.

Nucleoside.

As used herein, "nucleoside" means a base covalently attached to a sugar or sugar analog and which may contain a phosphite or phosphine. The term nucleoside includes ribonucleosides, deoxyribonucleosides, or any other nucleoside which is an N-glycoside or C-glycoside of a base. The stereochemistry of the sugar carbons can be other than that of D-ribose.

Nucleosides include those species which contain modifications of the sugar moiety, for example, wherein one or more of the hydroxyl groups are replaced with a halogen, a heteroatom, an aliphatic group, or are functionalized as ethers, amines, thiols, and the like. The pentose moiety can be replaced by a hexose or an alternate structure such as a cyclopentane ring, a 6-member morpholino ring and the like.

The term "nucleoside" will include ribonucleosides, deoxyribonucleosides, or any other nucleoside which is an N-glycoside or C-glycoside of a base, including purine or pyrimidine bases. The stereochemistry of the sugar carbons can be other than that of D-ribose in one or more residues. The pentose moiety can be replaced by a hexose and incorporated into oligomers as described (Augustyns, K., et al, *Nucl Acids Res* (1992) 20:4711–4716). Also included are analogs where the ribose or deoxyribose moiety is replaced by an alternate structure such as a hexose or such as the 6-member morpholino ring described in U.S. Pat. No. 5,034,506. Nucleosides as defined herein also include a purine or pyrimidine base linked to an amino acid or amino acid analog having a free carboxyl group and a free amino group or protected forms thereof.

Nucleotide.

As used herein, "nucleotide" means a nucleoside having a phosphate group or phosphate analog (groups with phosphorus in the same oxidation state as in the phosphate group e.g. thiophosphate, amidate).

Sugar Modification.

As used herein, "sugar modification" means any pentose or hexose moiety other than 2'-deoxyribose. Modified sugars include D-ribose, 2'-O-alkyl (1–12C), 2'-amino, 2'-halo (F, Cl, Br, I) functionalized pentoses, hexoses and the like. Sugars having a stereochemistry other than that of a D-ribose are also included. For nucleomonomers where the 3' position is not part of the substitute linkage, modified sugars also include 3'-O-alkyl (1–12C), 3'-amino and 3'-halo functionalized pentoses, hexoses and the like.

Linkage.

As used herein, "linkage" means a phosphodiester moiety (—O—P(O)(O)—O—) that covalently couples adjacent nucleomonomers.

Substitute Linkages.

As used herein, "substitute linkage" means any analog of the native phosphodiester group or any suitable moiety that covalently couples adjacent nucleomonomers. Substitute linkage(s) can be utilized in the oligomers for a number of purposes such as to further facilitate binding with complementary target nucleic acid sequences and/or to increase the stability of the oligomers toward nucleases. Substitute linkages include phosphodiester analogs and nonphosphorus containing linkages, e.g. such as acetals and amides. Substitute linkages include the 3',5' allyl ether and 3',5' allyl sulfide linkages of the invention. By "phosphodiester analog" is meant an analog of the conventional phosphodiester linkage —O—P(O)O—O—as well as alternative linking groups, e.g. such as phosphorothioate and methylphosphonate.

Switchback.

As used herein, "switchback" means an oligomer having at least one region of inverted polarity. Switchback oligomers are able to bind to opposite strands of a duplex to form a triplex on both strands of the duplex. Suitable linkers ("switchback linker") joining the regions of inverted polarity are substitute linkages and have been described.

Crosslinking moiety.

"Crosslinking moiety" includes a group or moiety in an oligomer that forms a covalent bond with a target nucleic acid. Crosslinking moieties include covalent bonding species that covalently link an oligomer to target nucleic acids either spontaneously (e.g. $N^4,N^4$-ethanocytosine) or via photoactivation (e.g. psoralen and the like).

Oligomers.

"Oligomers or oligomer" are defined herein as two or more nucleomonomers covalently coupled to each other by a linkage or substitute linkage. Thus, an oligomer can have as few as two covalently linked nucleomonomers (a dimer). Oligomers can be binding competent and, thus, can base pair with cognate single-stranded or double-stranded nucleic acid sequences. Short oligomers (e.g. dimers, trimers, tetramers, pentamers, hexamers and the like) are also useful as synthons for longer oligomers as described herein. Oligomers usually will be single stranded and have a uniform polarity but can have regions of inverted polarity or can be circular or branched. Oligomers can also contain abasic sites and pseudonucleosides (US91/01141).

Oligomer includes oligonucleotides, oligonucleosides, polydeoxyribonucleotides (containing 2′-deoxy-D-ribose or modified forms thereof), i.e., DNA, polyribonucleotides (containing D-ribose or modified forms thereof), i.e., RNA, and any other type of polynucleotide which is an N-glycoside or C-glycoside of a purine or pyrimidine base, or modified purine or pyrimidine base. Oligomer as used herein is also intended to include compounds where adjacent nucleomonomers are linked via amide linkages. Elements ordinarily found in oligomers, such as the furanose ring and/or the phosphodiester linkage can be replaced with any suitable functionally equivalent element. "Oligomer" is thus intended to include any structure that serves as a scaffold or support for the bases wherein the scaffold permits binding to target nucleic acids in a sequence-dependent manner.

Oligomers that are currently known can be defined into four groups that can be characterized as having (i) phosphodiester and phosphodiester analog (phosphorothioate, methylphosphonate, etc) linkages, (ii) substitute linkages that contain a non-phosphorous isostere (riboacetal, formacetal, carbamate, etc), (iii) morpholino residues, carbocyclic residues or other furanose sugars, such as arabinose, or a hexose in place of ribose or deoxyribose and (iv) nucleomonomers linked via amide bonds or acyclic nucleomonomers linked via any suitable substitute linkage.

Blocking Groups.

As used herein, "blocking group" refers to a substituent other than H that is conventionally coupled to oligomers or nucleomonomers, either as a protecting group, a coupling group for synthesis, $OPO_3^{-2}$, or other conventional conjugate such as a solid support, label, antibody, monoclonal antibody or fragment thereof and the like. As used herein, "blocking group" is not intended to be construed solely as a protecting group, according to slang terminology, but is meant also to include, for example, coupling groups such as a H-phosphonate or a phosphoramidite. By "protecting group" is meant is any group capable of protecting the 0-atom, S-atom or N-atom to which it is attached from participating in a reaction or bonding. Such protecting groups for N-atoms on a base moiety in a nucleomonomer and their introduction are conventionally known in the art. Non-limiting examples of suitable protecting groups include diisobutylformamidine, benzoyl and the like. Suitable "protecting groups" for O-atoms and S-atoms are, for example, DMTO, MMTO, FMOC or esters.

Protecting group.

"Protecting group" as used herein includes any group capable of preventing the O-atom, S-atom or N-atom to which it is attached from participating in a reaction or bonding. Such protecting groups for O-, S- and N-atoms in nucleomonomers are described and methods for their introduction are conventionally known in the art. Protecting groups also include any group capable of preventing reactions and bonding at carboxylic acids, thiols and the like.

Coupling group.

"Coupling group" as used herein means any group suitable for generating a linkage or substitute linkage between nucleomonomers such as a hydrogen phosphonate, a phosphoramidite and an alkyl ether.

Conjugate.

"Conjugate" as used herein means any group attached to the oligomer at a terminal end or within the oligomer itself. Conjugates include solid supports, such as silica gel, controlled pore glass and polystyrene; labels, such as fluorescent, chemiluminescent, radioactive atoms or molecules, enzymatic moieties and reporter groups; oligomer transport agents, such as polycations, serum proteins and glycoproteins and polymers and the like.

Synthon.

"Synthon" as used herein means a structural unit within a molecule that can be formed and/or assembled by known or conceivable synthetic operations.

Transfection.

"Transfection" as used herein refers to any method that is suitable for enhanced delivery of oligomers into cells.

Subject.

"Subject" as used herein means a plant or an animal, including a mammal, particularly a human.

Additional Nucleomonomer Modifications

Oligomers that are comprised of nucleomonomers can also contain various modifications in addition to the substitute linkages of the invention. A non-limiting exemplary list of such additional modifications includes oligomers where (i) one or more nucleomonomer residues are modified at the 2′ or 3′ nonlinking position, (ii) one or more covalent crosslinking moieties are incorporated, (iii) inverted polarity linkers (switchback linkers) are incorporated, (iv) other non-invention substitute linkages are included, (v) other base analogs, such as 8-oxo-$N^6$-methyladenine, are included and (vi) conjugates such as cholesterol, intercalating agents or polylysine that respectively enhance binding affinity to target nucleic acid sequences or that enhance association of the oligomer with cells are included. The binding competence of the invention oligomers for single-stranded and duplex targets is compatible with further modifications to the oligomer. These further modifications may also confer other useful properties such as stability to nuclease cleavage (e.g. in a domain of an invention oligomer having phosphodiester linkages), or enhance their ability to permeate cell membranes, and the like.

Oligomers.

In oligomers of the invention, at least one allyl ether or allyl sulfide linkage is present. One substitute linkage may be used repeatedly in this structure, or, if desired a variety of substitute linkages may be used. The oligomers of the invention can be formed using invention and conventional nucleomonomers and synthesized using standard solid phase (or solution phase) oligomer synthesis techniques, which are now commercially available. In general, the invention oligomers can be synthesized by a method comprising the steps of: synthesizing a nucleomonomer or oligomer synthon having a protecting group and a base and a coupling group capable of coupling to a nucleomonomer or oligomer; coupling the nucleomonomer or oligomer synthon to an acceptor nucleomonomer or an acceptor oligomer; removing the protecting group; and repeating the cycle as needed until the desired oligomer is synthesized. The oligomers of the present invention can be of any length including those of greater than 40, 50, 100, 200 or 500 nucleomonomers. In general, preferred oligomers contain 2-30 nucleomonomers. Lengths of greater than or equal to about 8 to 20 nucleomonomers are useful for therapeutic or diagnostic applications. Short oligomers containing 2, 3, 4 or 5 nucleomonomers are specifically included in the present invention and are useful as synthons.

Oligomers having a randomized sequence and containing about 6, 7 or 8 nucleomonomers are useful for primers that are used in cloning or amplification protocols that use random sequence primers, provided that the oligomer contains about 1 or 2 residues at the 3' end that can serve as a primer for polymerases or reverse transcriptases or that otherwise do not interfere with polymerase activity. Oligomers can contain conventional phosphodiester linkages or can contain other non-invention substitute linkages such as phosphoramidate linkages in addition to the invention substitute linkages. Particularly preferred substitute linkages for use in the oligomers of the present invention include phosphodiester, phosphorothioate, methylphosphonate and thionomethylphosphonate substitute linkages.

Oligomers of the invention can be synthesized one nucleomonomer residue at a time, each individual linkage, and/or substitute linkage, and the nature of each individual "B" substituent can be chosen at will. Since the oligomers are prepared sequentially, any pattern of linkage or substitute linkage types, bases and sugar modifications may be used. In some preferred embodiments, the substitute linkages alternate in a regular pattern. For example, one invention substitute linkage followed by two phosphodiester linkages followed by one invention substitute linkage etc. Additional alternatives might include, for example, alternating linkages such as a an invention substitute linkage followed by a phosphodiester analog (thioate, etc) followed by an invention substitute linkage followed by a phosphodiester analog, etc., so that there is a one-by-one alternation of the two types of substitute linkages. A variety of different patterns is readily derived. Abbreviation of oligomer base sequences may be used. For example, in standard DNA (or RNA) the sequences are generally denoted by the sequence of bases alone, such as, for example, ATG CGC TGA. In general, it is simply stated in advance whether this represents RNA, DNA or an analog. In the compounds of the invention, similar notation will be used for modifications of otherwise physiological DNA or RNA molecules but the 3',5' phosphodiester linkages replaced by the invention substitute linkages will be noted.

Salts.

Any acceptable salt can be used and such salt forming materials are well known in the art. acceptable salts are preferably metal or ammonium salts of the oligomers of the invention and include alkali or alkaline earth metal salts, e.g., the sodium, potassium, magnesium or calcium salt; or advantageously easily crystallizing ammonium salts derived from ammonia or organic amines, such as mono-, di- or tri-lower (alkyl, cycloalkyl or hydroxyalkyl)-amides, lower alkylenediamines or lower (hydroxyalkyl or arylalkyl)-alkylammonium bases, e.g. methylamine, diethylamine, triethylamine, dicyclohexylamine, triethanolamine, ethylenediamine, tris-(hydroxymethyl)-aminomethane or benzyl-trimethylammonium hydroxide. The oligomers of the invention form acid addition salts, which are preferably such of therapeutically acceptable inorganic or organic acids, such as strong mineral acids, for example hydrohalic, e.g., hydrochloric or hydrobromic acid; sulfuric, phosphoric; aliphatic or aromatic carboxylic or sulfonic acids, e.g., formic, acetic, propionic, succinic, glycollic, lactic, malic, tartaric, gluconic, citric, ascorbic, maleic, fumaric, hydroxymaleic, pyruvic, phenylacetic, benzoic, 4-aminobenzoic, anthranilic, 4-hydroxybenzoic, salicylic, 4-aminosalicylic, methanesulfonic, ethanesulfonic, hydroxyethanesulfonic, benzenesulfonic, sulfanilic or cyclohexylsulfamic acid and the like.

Blocking Groups.

Figure 2:
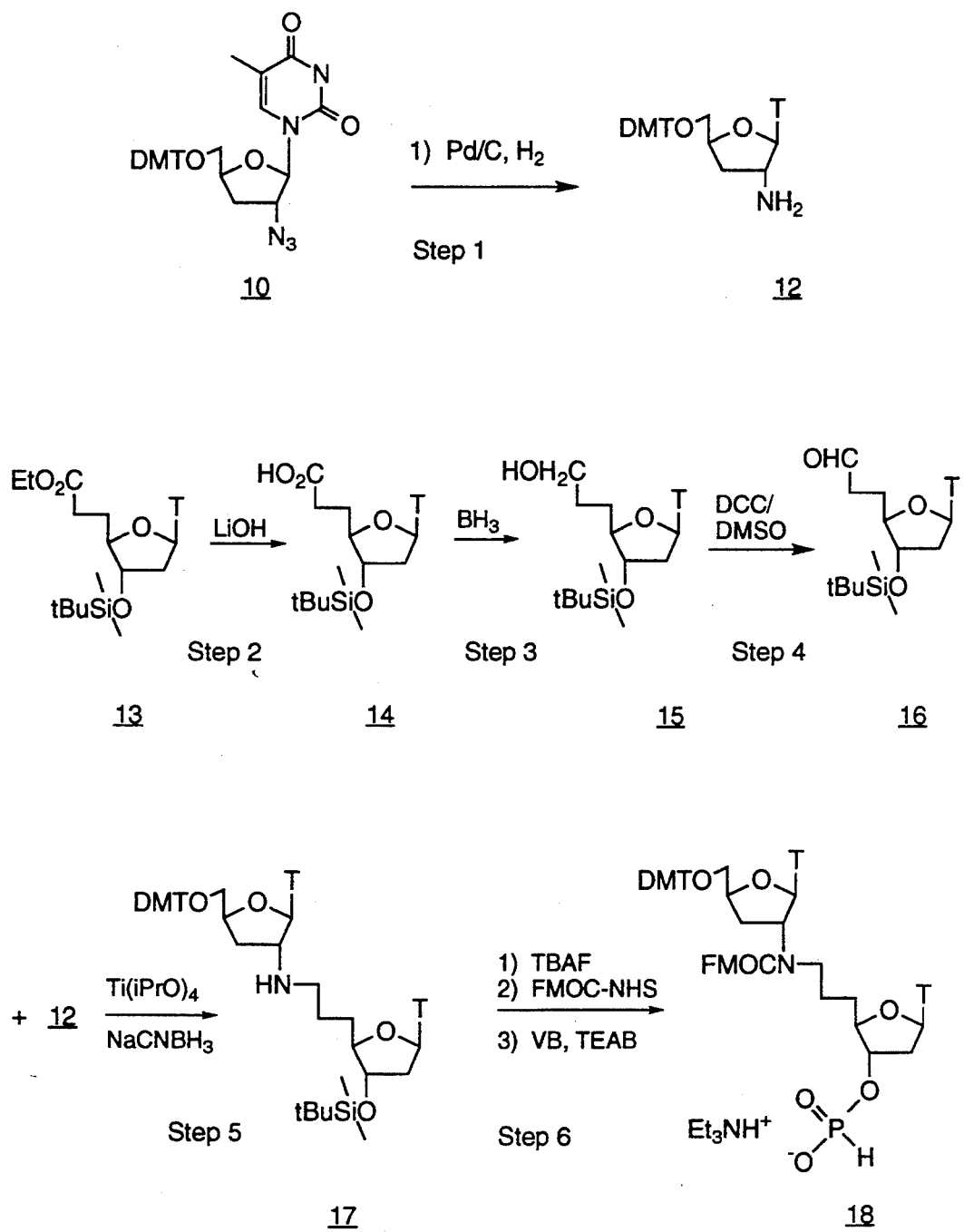

1. Coupling Groups. Suitable coupling groups are, for example, H-phosphonate, a methyl-phosphonamidite, or a phosphoramidite. Phosphoramidites that can be used include $\beta$-cyanoethylphosphoramidites (preferred). Methylphosphonamidites, alkylphosphonamidites (including ethylphosphonamidites and propylphosphonamidites) can also be used. Exemplary phosphoramidites are shown in FIGS. 26-1 and 26-2.

Figure 4:
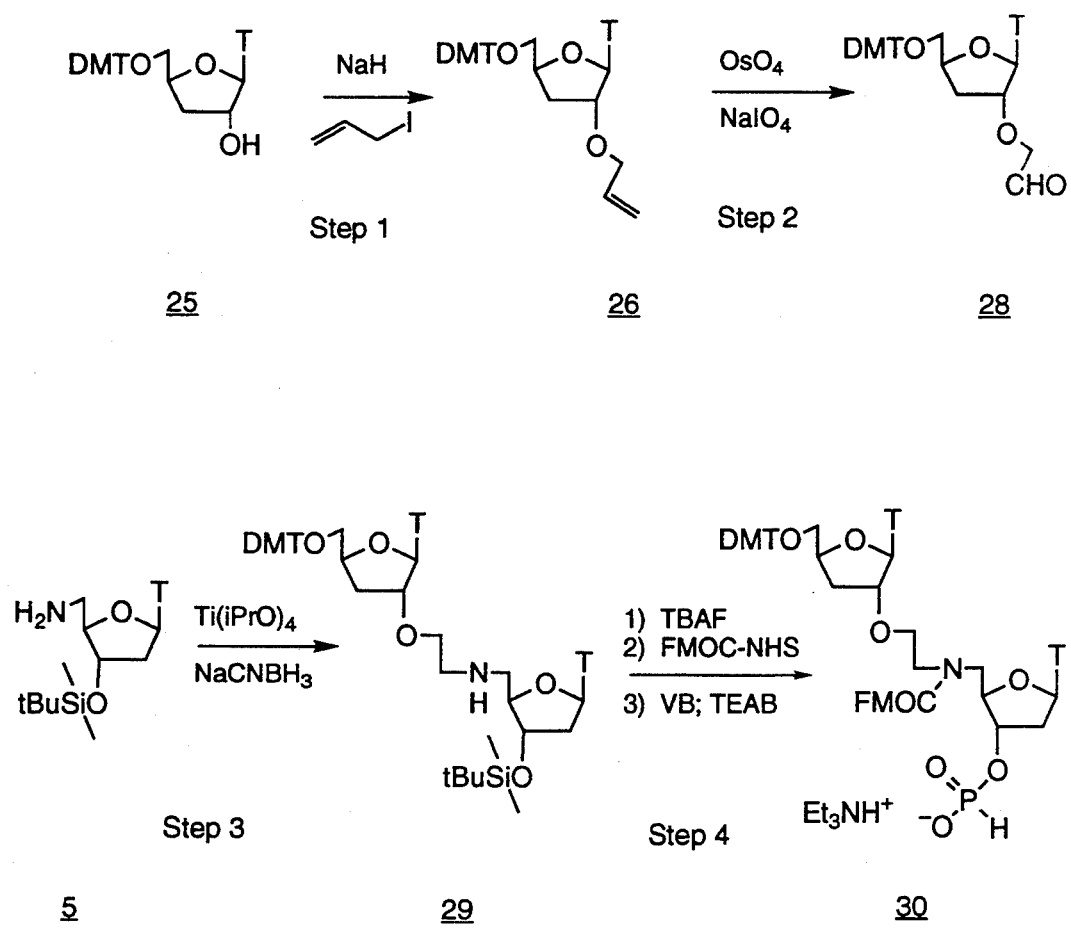
Figure 25:
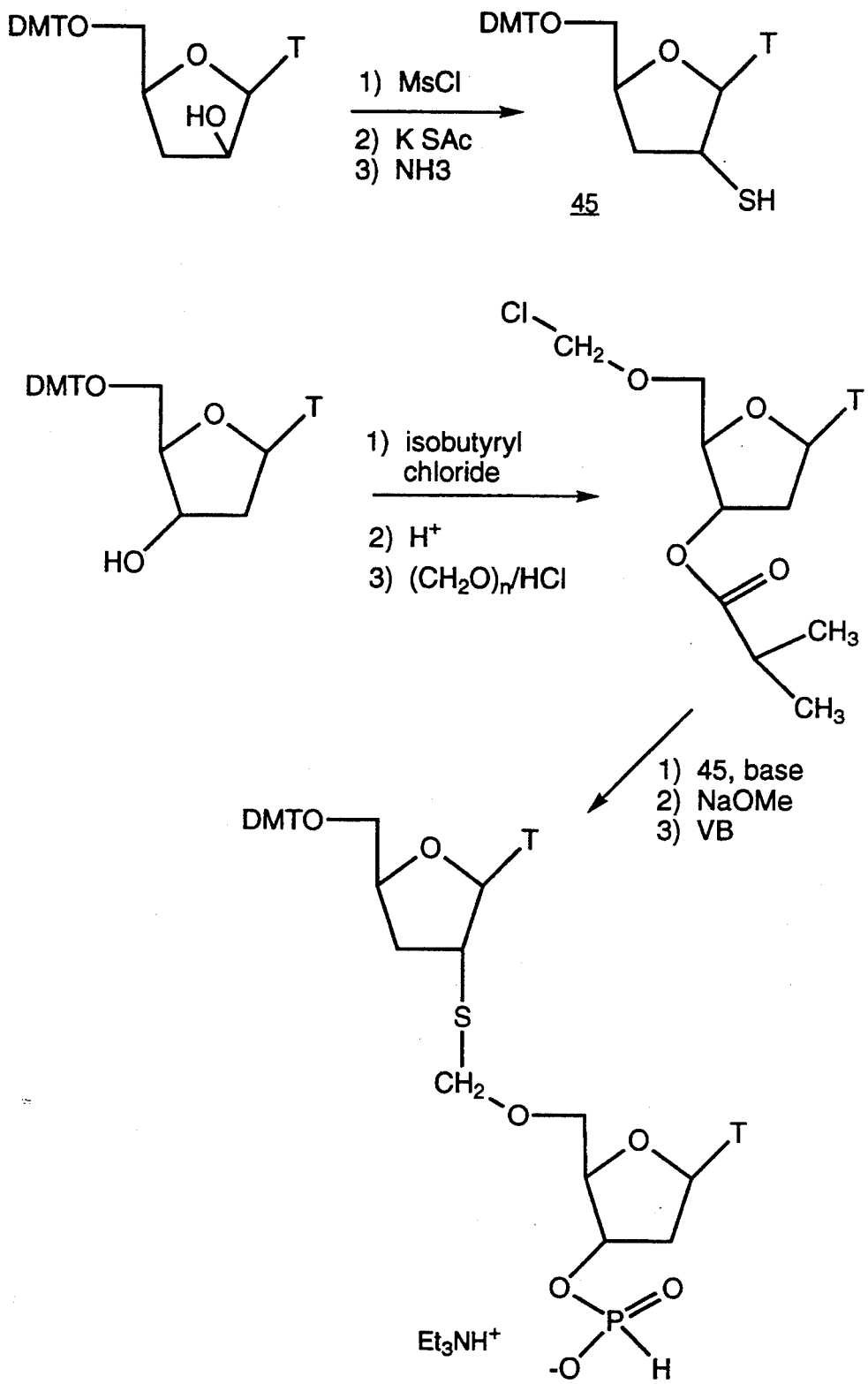
Figure 27:
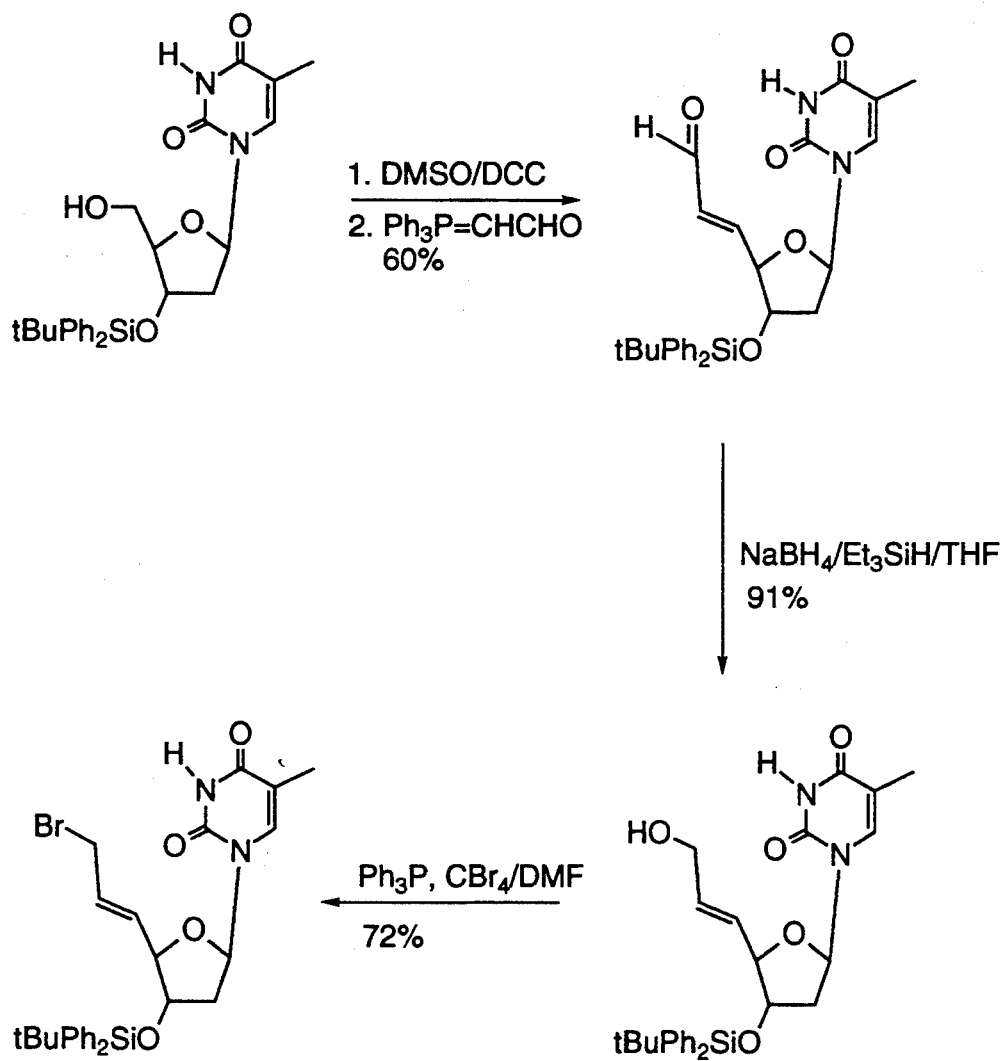
Figures 1, 28A:
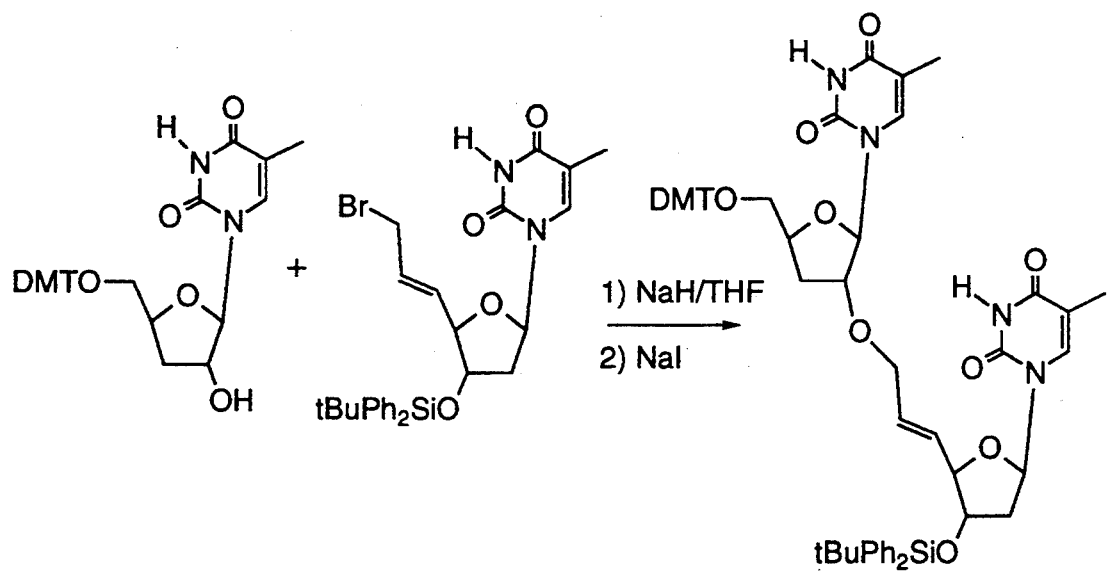
Figures 2, 28A:
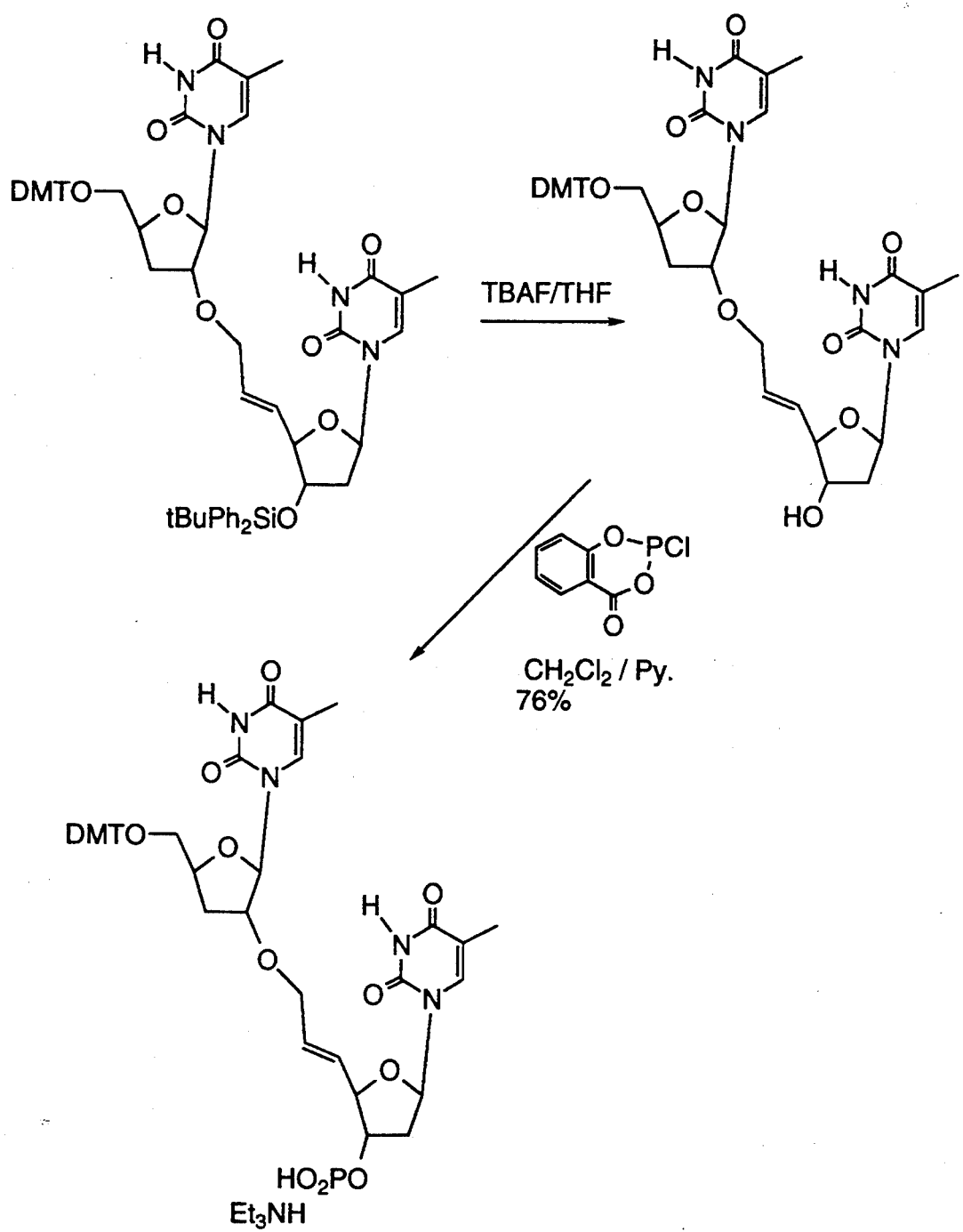
Figures 1, 29A:
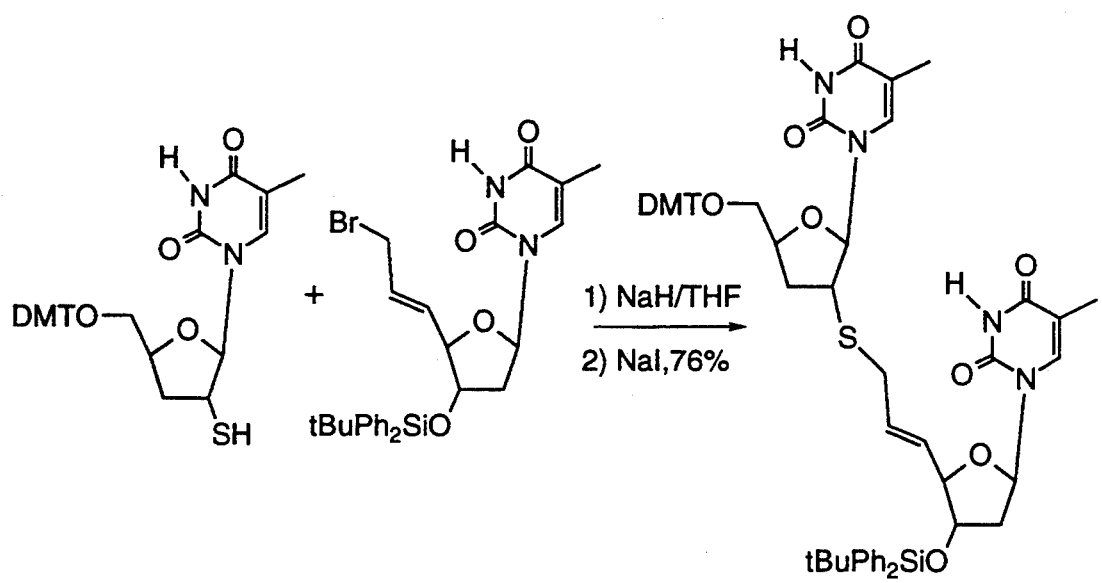
Figures 2, 29A:
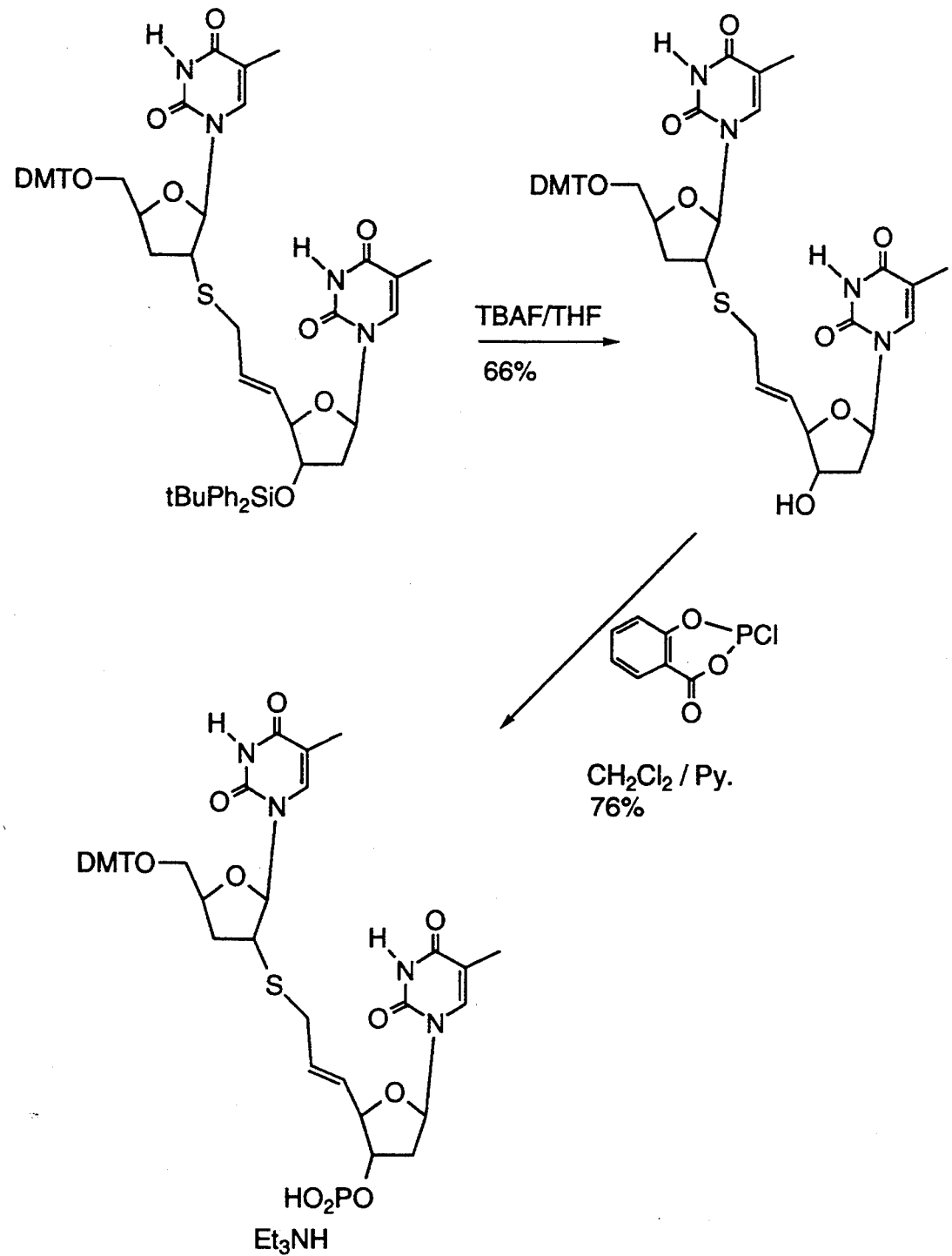
Figures 1, 30A:
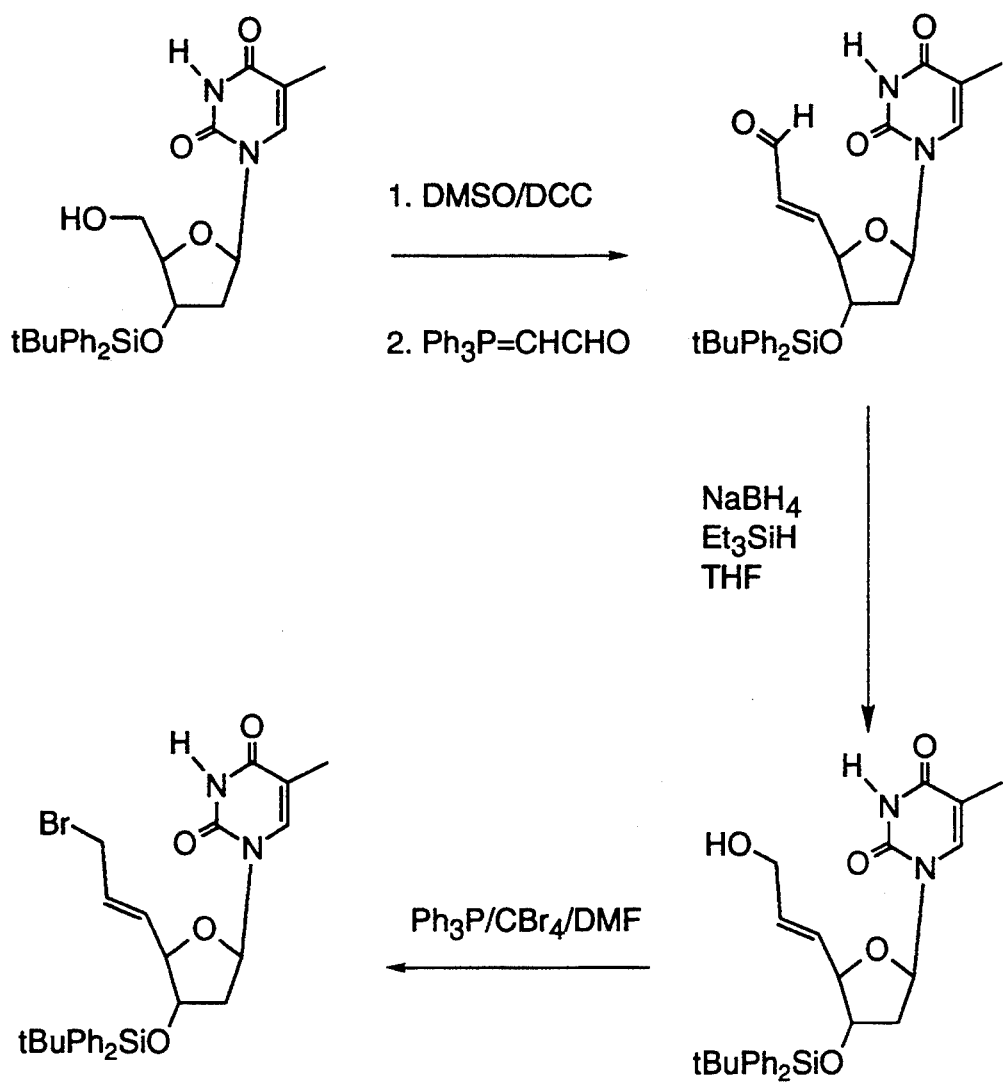
Figures 2, 30A:
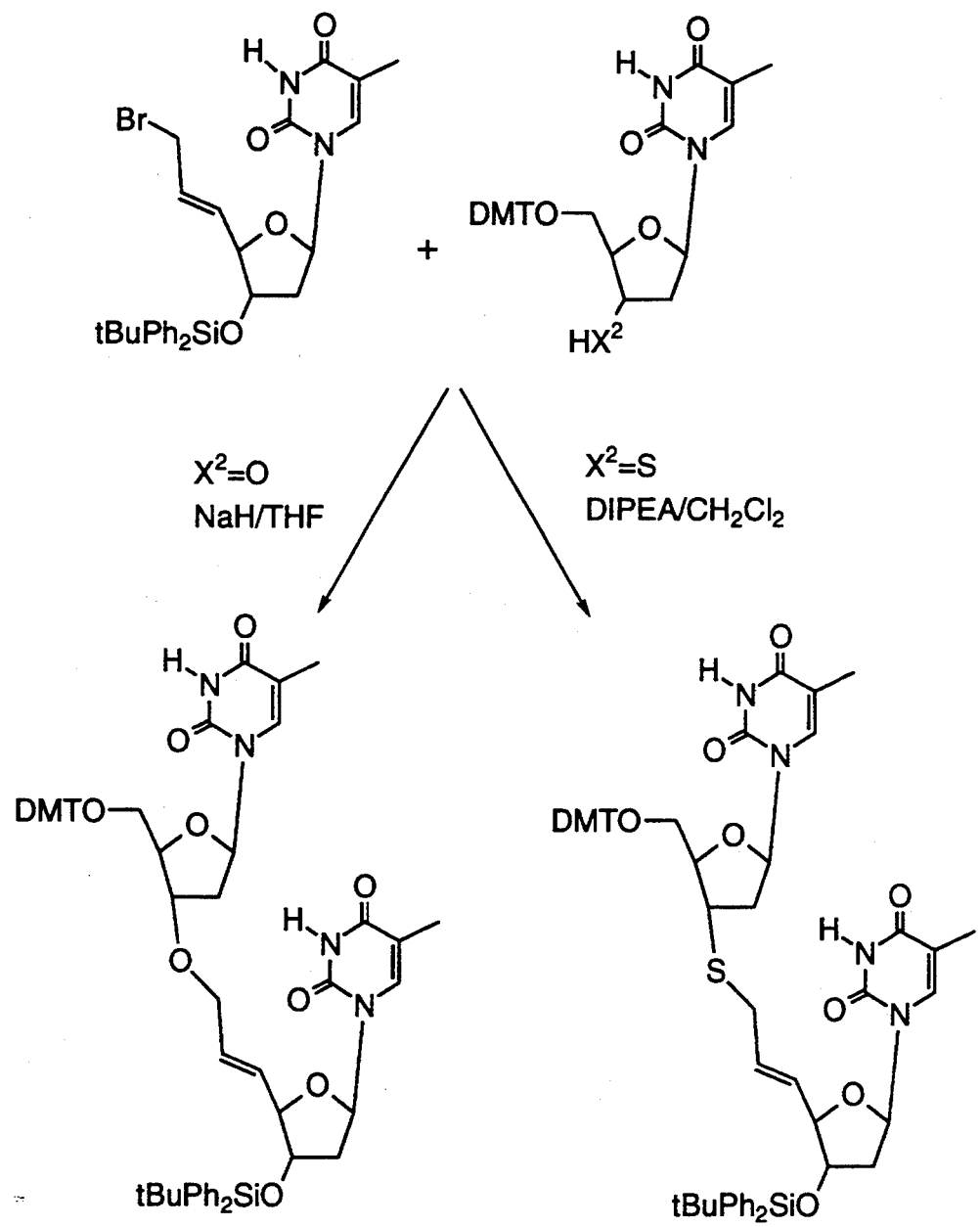
Figures 3, 30A:
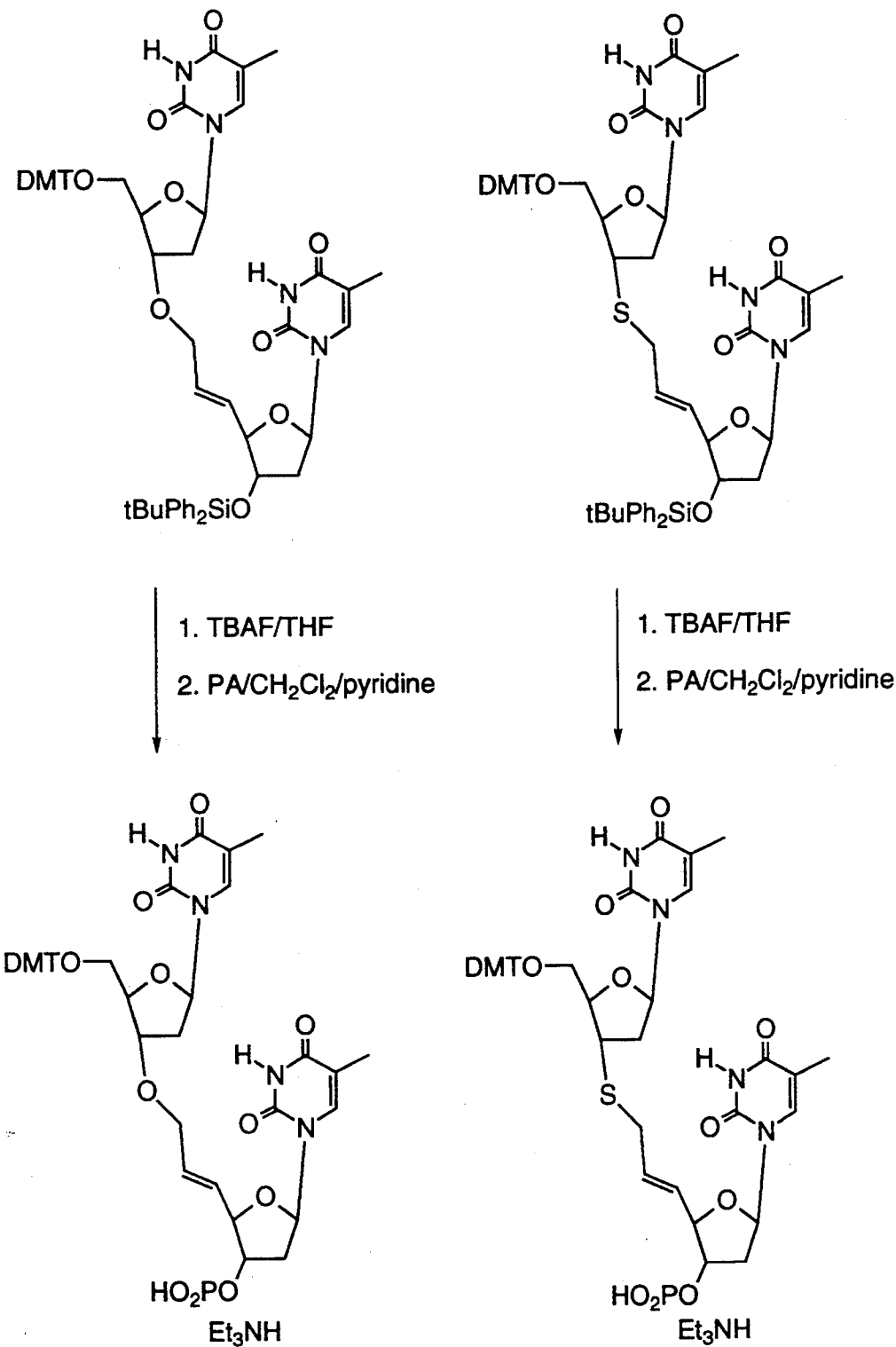
Figures 4, 30A:
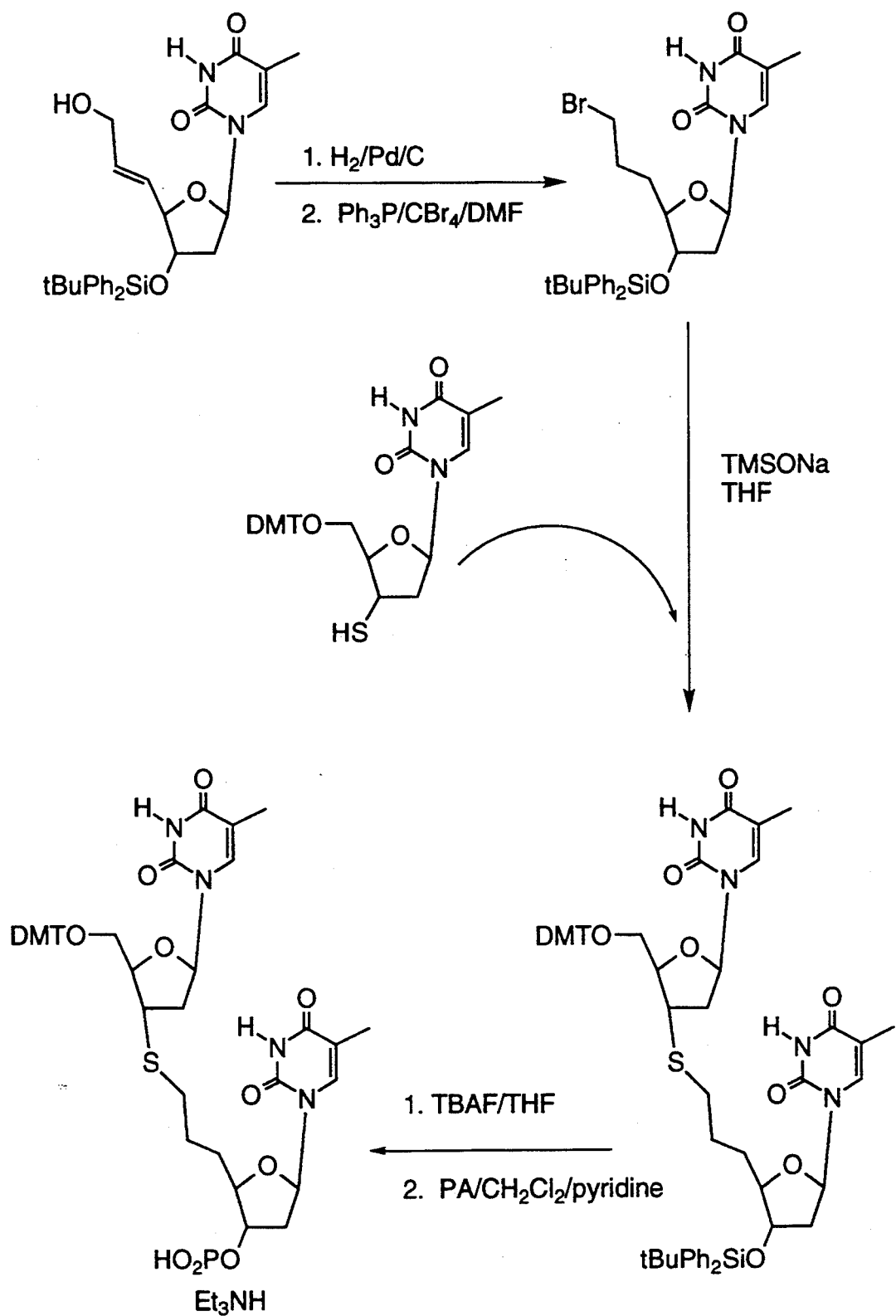
Figure 31:
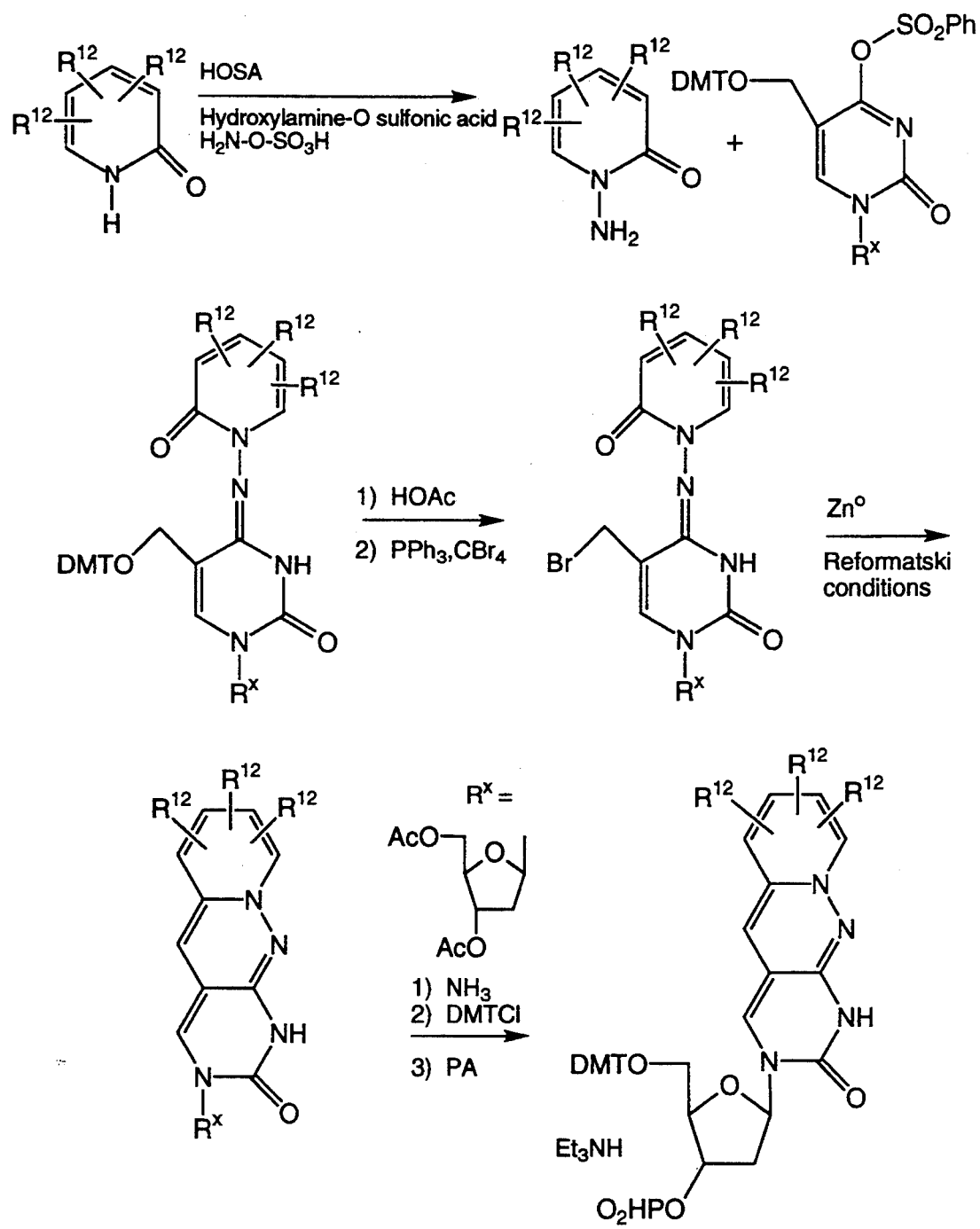
Figure 32:
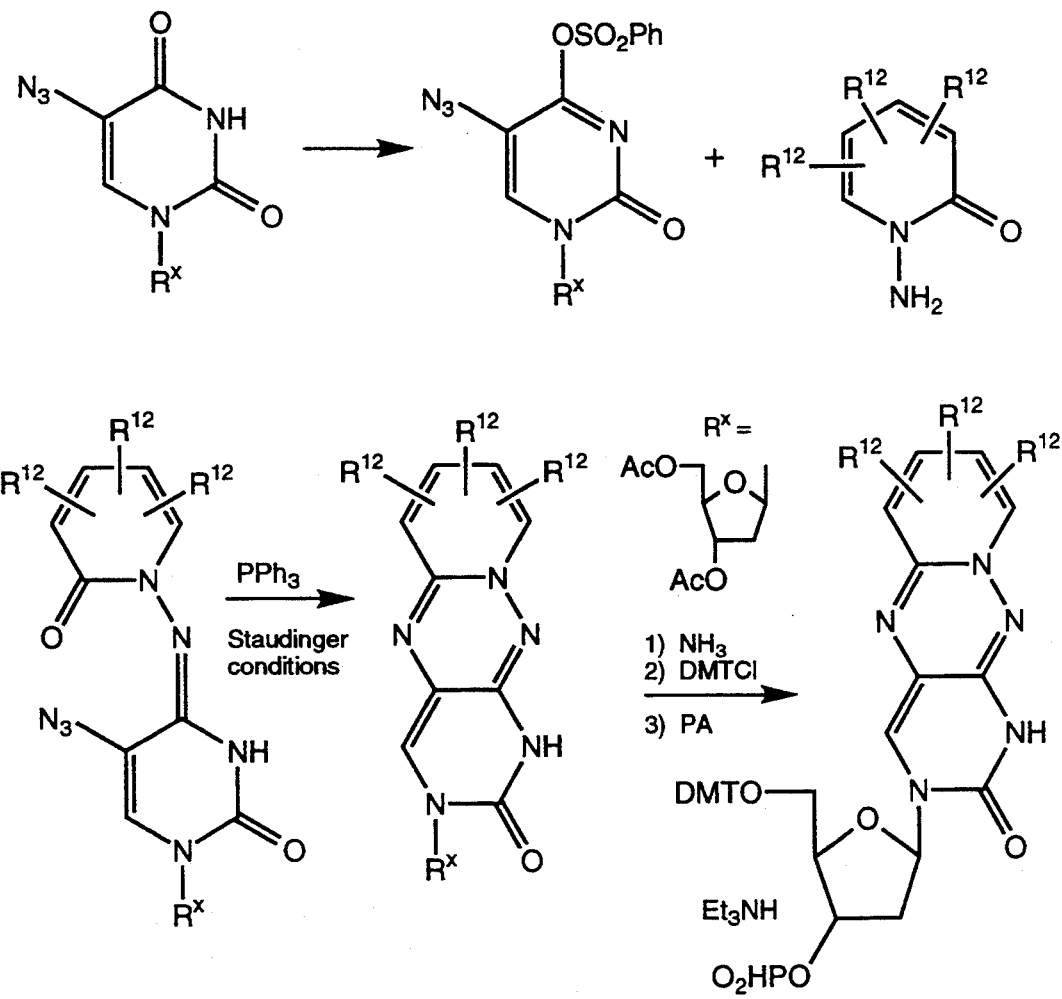
Figure 33:
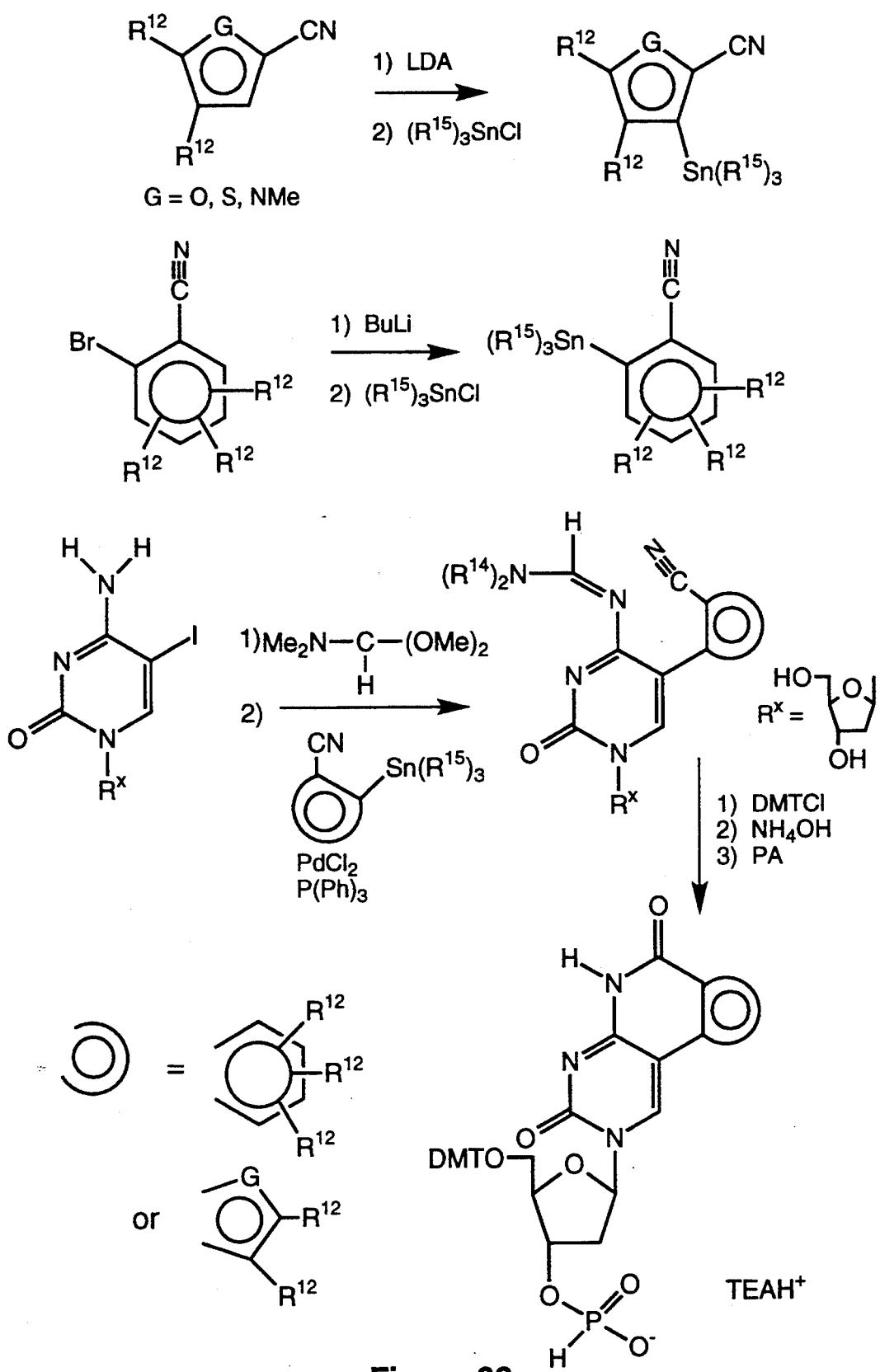
Figure 34:
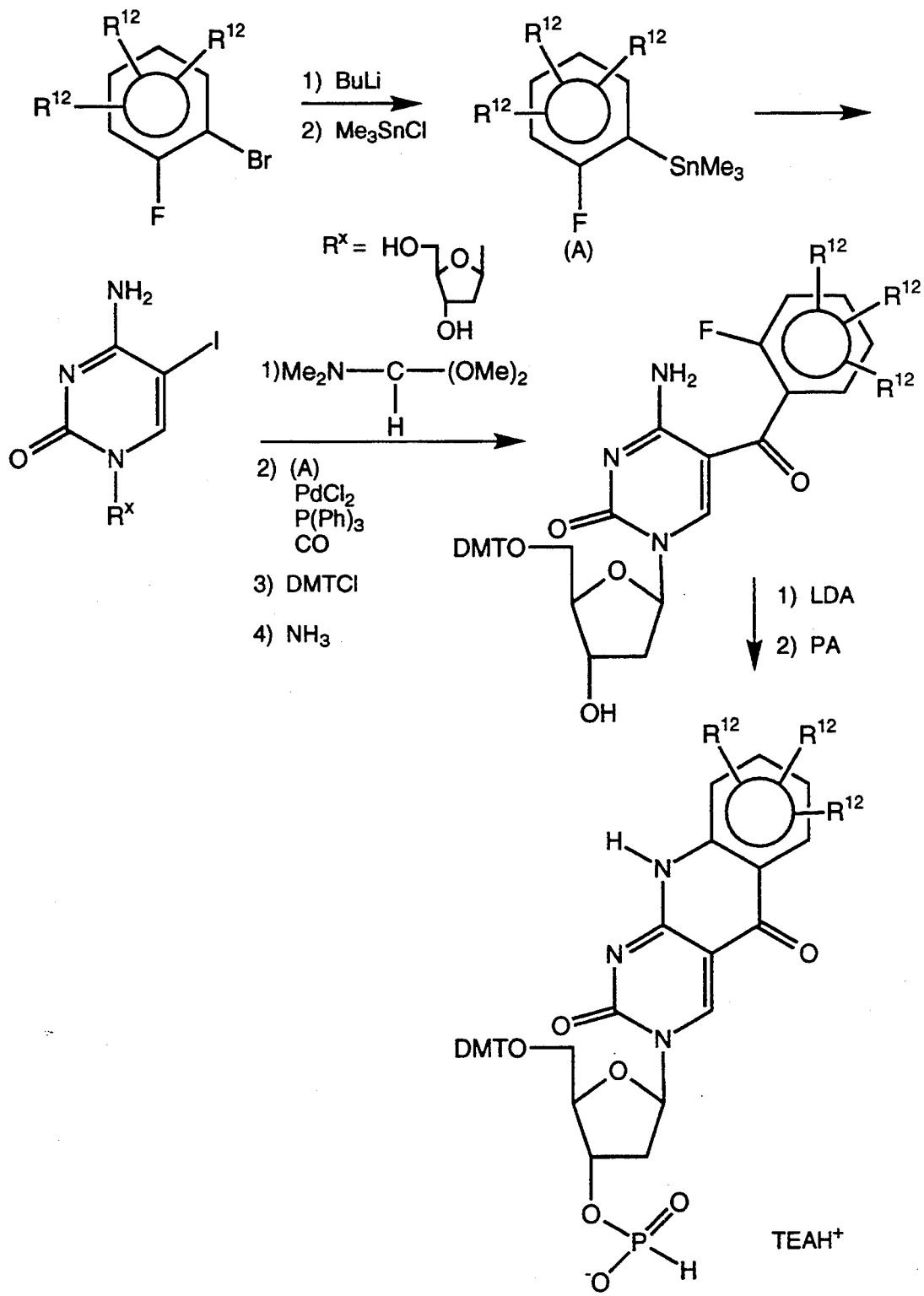

Suitable "coupling groups" at the 3', 2' or 5' position for oligomer synthesis via phosphoramidite triester chemistry, referred to herein as "amidite" chemistry, include N,N-diisopropylamino-$\beta$-cyanoethoxyphosphine, N,N-diisopropylaminomethoxyphosphine, N,N-diethylamino-$\beta$-cyanoethoxyphosphine, (N-morpholino)-$\beta$-cyanoethoxyphosphine, and (N-morpholino)-methoxyphosphine (Moore, M. F. et al, *J Org Chem* (1985) 50:2019-2025; Uznanski, A. W., et al, *Tel Lett* (1987) 28:3401-3404; Bjergarde, K., et al, *Nucl Acids Res* (1991) 19:5843-5850; Dahl, O. *Sulfur Reports* (1991) 11:167-192). Related coupling groups such as N,N-diisopropylamino-methyl-phosphine or N,N-diethylamino-methylphosphine can also be used to prepare methylphosphonates (FIG. 25-4). Methylphosphonate oligomers can be conveniently synthesized using coupling groups such as N,N-diisopropylamino-methyl-phosphonamidite, and N,N-diethylamino-methylphosphonamidite. Synthesis of nucleomonomer amidites of the invention can be accomplished by conventional methods (for example, Gryaznov, S. M., et al, *Nucl Acids Res* (1992) 20:1879-1882; Vinayak, R., et al, *Nucl Acids Res* (1992) 20:1265-1269; Sinha, N. D., et al, *Nucl Acids Res* (1984) 12:4539-4557; and other references cited herein). Suitable coupling groups at the 3', 2'(or 5') position for oligomer synthesis via phosphate triester chemistry, referred to herein as "triester" chemistry, include 2-chlorophenyl phosphate, 4-chlorophenyl phosphate, 2,4-dichlorophenyl phosphate and 2,4,-dibromophenyl phosphate nucleotide diester derivatives or, for synthesis of phosphorothioate linkages, the thiono derivatives thereof (Marugg, J. E., et al, *Nucl Acids Res* (1984) 12:9095-9110; Kemal, O., et al, *J Chem Soc Chem Commun* (1983) 591-593; Kamer, P. C. J., et al, *Tet Lett* (1989) 3:6757-6760).

2. Protecting Groups.

Protecting groups such as diisobutylformamidine, benzoyl, isobutyryl, FMOC, dialkylformamidine, dialkylacetamidine or other groups known in the art can be used to protect the exocyclic nitrogen of the cytosine, adenine or guanine heterocycles. Alternatively, cytidine can be directly incorporated into oligomers without a protecting group at the exocyclic nitrogen using described methods (Gryaznov, S. M. et al, *J Amer Chem Soc* (1991) 113:5876-5877; Gryaznov, S. M., et al, *Nucl Acids Res* (1992) 20:1879-1882; Kung, P.-P., et al, *Tetrahedron Letters* (1992) 33:5869-5872). Suitable protecting groups are DMTO, Bz (benzoyl), iBu (isobutyryl), phenoxyacetyl, MMTO or FMOC at the 5' terminus and/or hydrogen phosphonate, methyl phosphoramidite, methyl phosphonamidite, β-cyanoethylphosphoramidite, TBS (t-butyldimethylsilyl) or TBDPS (t-butyldiphenylsilyl) at the 3'-terminus.

Preferred protecting groups are Bz (benzoyl), DMTO, MMTO or FMOC at the 5' terminus or position and/or TBS, hydrogen phosphonate, methylphosphoramidite, methylphosphonamidite, β-cyanoethylphosphoramidite at the 3'- terminus. However, it is intended that the position of the blocking groups can be reversed as needed (e.g., a phosphoramidite at the 5'-position and DMT at the 3'- position). In general, the nucleomonomers and oligomers of the invention can be derivatized to such "blocking groups" as indicated in the relevant formulas by methods known in the art.

Conjugates.

Also included are "conjugates" of oligomers. "Conjugates" of the oligomers include those conventionally recognized in the art. For instance, the oligomers can be covalently linked to various moieties such as, intercalators, and substances which interact specifically with the minor groove of the DNA double helix. Other chosen conjugate moieties, can be labels such as radioactive, fluorescent, enzyme, or moieties which facilitate cell association using cleavable linkers and the like. Suitable radiolabels include $32_P$, $35_S$, $3_H$, $131_I$ and $14_C$; and suitable fluorescent labels include fluorescein, resorufin, rhodamine, BODIPY (Molecular Probes) and Texas red; suitable enzymes include alkaline phosphatase and horseradish peroxidase. Other compounds which can be used as covalently linked moieties include biotin, antibodies or antibody fragments, asialoglycoprotein, transferrin and the HIV Tat protein can also conveniently be linked to the oligomers of the invention. These additional moieties can be derivatized through any convenient moiety. For example, intercalators, such as acridine or psoralen can be linked to the oligomers of the invention through any available —OH or —SH, e.g., at the terminal 5'- position of the oligomer, the 2'-positions of RNA, or an OH, $NH_2$, COOH or SH incorporated into the 5-position of pyrimidines. A derivatized form which contains, for example, $—CH_2CH_2NH_2$, $—CH_2CH_2CH_2OH$ or $—CH_2CH_2CH_2SH$ in the 5- position of pyrimidines is convenient. Conjugates including polylysine or lysine can be synthesized as described and can further enhance the binding affinity of an oligomer to its target nucleic acid sequence (Lemaitre, M. et al, Proc Natl Acad Sci (1987) 84:648–652; Lemaitre, M. et al, Nucleosides and Nucleotides (1987) 6:311–315).

A wide variety of substituents can be attached, including those bound through linkages or substitute linkages. The —OH moieties in the oligomers can be replaced by phosphate groups, protected by standard protecting groups, or coupling groups to prepare additional linkages to other nucleomonomers, or can be bound to the conjugated substituent. The 5'- terminal OH can be phosphorylated; the 2'—OH or OH substituents at the 3'- terminus can also be phosphorylated. The hydroxyls can also be derivatized to standard protecting groups. Oligomers of the invention can be covalently derivatized to moieties that facilitate cell association using cleavable linkers. Linkers used for such conjugates can include disulfide linkages that are reduced after the oligomertransport agent conjugate has entered a cell. Appropriate molecular linkers include for example, $—R^7—X^8—CH_2CHR^{10}—SS—CHR^{10}CH_2—X^8—Y^1$- wherein each $R^7$ is independently alkylene (1–9C; including methylene, ethylene and propylene), or CO, each $X^8$ is independently O, S(O)(O), S(O), $NR^{10}$, $CH_2$, $C(R^{10})_2$ or CO; $R^{10}$ wherein each $R^{10}$ is independently H, alkyl (1–6C; including methyl, ethyl and propyl), or 6–10C aryl and which linkers have been previously described (WO 91/14696). Disulfide-containing linkers of this type have a controllable half-life in vivo, facilitating its use as a prodrug/transport component. Such linkers are stable under extracellular conditions relative to intracellular conditions due to the redox potential of the disulfide linkage. Suitable conjugates also include solid supports for oligomer synthesis and to facilitate detection of nucleic acid sequences. Solid supports include, but are not limited to, silica gel, controlled pore glass, polystyrene, and magnetic glass beads.

Sugar Modifications.

Derivatives can be made by substitution on the sugars. Among the preferred derivatives of the oligomers of the invention are the 2'—O—allyl or 3'—O—allyl derivatives of ribose or xylose.

Because the α-anomer binds to duplex DNA or single-stranded RNA in a manner similar to that for the β anomers but with a reversed polarity, oligomers can contain nucleomonomers having this epimer or a domain thereof (Praseuth, D., et al, Proc Natl Acad Sci (USA) (1988) 85:1349–1353; Sun, J. S. et al, Proc Natl Acad Sci (1991) 88:6023–6027; Debart, F., et al, Nucl Acids Res (1992) 20:1193–1200). α-Anomeric oligomers containing the substitute linkages described herein represent a class of modified oligomers included in the present invention.

When X is $CH_2$ or CHF, the material may be produced according to published procedures (Otvos, et al, Tet Letters (1987) 28:6381–6384; Divakar, et al, J Chem Soc Perkin Trans I (1982) 1625; J Chem Soc. Perk Trans I (1991) 2373–2377).

Nucleomonomers comprising morpholino sugar analogs and their incorporation into oligomers have been described (Stirchak, E. P. et al, Nucleic Acids Res (1989) 17:6129–6141; EP 216 860; WO 86/05518; U.S. Pat. No. 5,034,506). Such nucleomonomers can be linked by various different substitute linkages including the invention substitute linkages.

Noninvention Substitute Linkages.

Typical invention oligomers will contain one or more invention substitute linkages and one or more phosphodiester linkages or one or more noninvention substitute linkages such as phosphorothioate, 2'- or 3'-thioformacetal, 2'- or 3'-formacetal, methylphosphonate or thionomethylphosphonate. The invention oligomers can comprise invention substitute linkages in combination with other types of linkages, wherein an invention linkage and a noninvention linkage links every other nucleomonomer. Invention oligomers can also comprise a domain of 3, 4, 5, 6, 7, 8, 9, 10, 11, 12, 13, 14, 15, 16, 17, 18 or more nucleomonomers that are uniformly linked by invention substitute linkages which optionally includes such oligomers having one or more other noninvention linkage types.

Noninvention substitute linkages, in addition to the novel linkages disclosed herein, are generally understood in the art. Noninvention substitute linkages include phosphorus-containing moieties. Such substitute linkage groups include, but are not limited to embodiments wherein the P(O)O is replaced with P(S)S (phosphorodithioate), P(O)S (phosphorothioate), P(O)NR$^3$, P(O)R$^3$, P(O)OR$^4$, wherein R$^3$ is H or alkyl (1–6C) and R$^4$ is alkyl (1–6C including methyl, ethyl, propyl, butyl and their isomers), —O—P(O)(NR$^{11}$$_2$)—X$^1$, —O—P-(O)(R$^{11}$)—O—, —O—P(S)(R$^{11}$)—O— (thionoalkylphosphonate including thionomethylphosphonate and thionoethylphosphonate),—P(O)(OR$^{11}$)-X$^1$, —O—C(O)—X$^1$, or —O—C(O)(NR$^{11}$$_2$)—X$^1$—, wherein R$^{11}$ is H (or a salt) or alkyl (1-12C including methyl, ethyl, propyl, butyl and their isomers) and R$^{11}$ is alkyl (1-9C including methyl, ethyl, propyl, butyl and their isomers) and the linkage is joined to adjacent nucleomonomers through an —O— or —S— bonded to a carbon of the nucleomonomer and X$^1$ is O or S, alkylphosphonates (including methylphosphonate, and ethylphosphonate), morpholino carbamate, morpholino sulfamate, morpholino sulfamide, boranophosphate (—O—P(OCH$_3$)(BH-3)—O—), siloxane (—O—Si(X$^4$)(X$^4$)—O—; X$^4$ is 1-6C alkyl including methyl, ethyl, propyl, butyl and their isomers or phenyl) and phosphoramidate (methoxyethylamine (—O—P(NCH$_2$CH$_2$OCH$_3$)(O)—O—) and the like), and are synthesized as described (Sood, A., et al, *J Am Chem Soc* (1990) 112:9000-9001; WO 91/08213; WO 90/15065; WO 91/15500; US90/03138; Stirchak, E. P. et al, *Nucleic Acid Res* (1989) 17:6129-6141; U.S. Pat. Nos. 5,034,506; 5,142,047; Hewitt, J. M. et al, Nucleosides and Nucleotides (1992) 11:1661-1666; EP 216 860).

Noninvention substitute linkages that can be used in the oligomers disclosed herein also include the sulfonamide (—O—SO$_2$—NH—), sulfide (—CH$_2$—S—CH$_2$—), sulfonate (—O—SO$_2$—CH$_2$—), carbamate (—O—C(O)—NH—, —NH—C(O)—O—), N,N'-dimethylhydrazino (—CH$_2$—N(CH$_3$)-N(CH$_3$)—), sulfamate (—O—S(O)(O)—N—; —N—S(O)(O)—N—), 2'- or 3'-thioformacetal (—S—CH$_2$—O—), formacetal (—O—CH$_2$—O—), 3'-amine (—NH—CH$_2$—CH$_2$—), N-methylhydroxylamine (—CH$_2$—N(CH$_3$)—O—) and 2',5'linkages (such as 2',5' carbamate (2'-N(H)-C(O)-O-5'), 5',2' carbamate (2'—O—C(O)—N(H)—5'), 5',2' methylcarbamate (2'-O-C(O)-N(CH)-5'), 5',2' thioformacetal (2'—O—CH$_2$—S—5'), 2' or 3' —CH=N—O—5', 2' or 3' —CH$_2$-N(H)—O—, 2' or 3'—CH$_2$—N(H)—N(H)—5'. Also included are linkages where the 5' methylene carbon (—CH$_2$—) of ribose or deoxyribose is replaced by a group such as —C(O)— or =CH— to give substitute linkages of the formulas 2' or 3' —CH$_2$—CH$_2$-N(H)—C(O)—or 2' or 3'—CH$_2$—O—N=CH—. Substitute linkages have been disclosed (see for example, U.S. Ser. Nos. 91/06855; 92/03385; WO 92/20822; WO92/20823; 07/892,902; 92/04294; Vaseur, J-J. et al, *J Amer Chem Soc* (1992) 114:4006-4007; Musicki, B. et al, *J Org Chem* (1990) 55:4231-4233; Reynolds, R. C., et al, *J Org Chem* (1992) 57:2983-2985; Mertes, M. P., et al, *J Med Chem* (1969) 12:154-157; Mungall, W. S., et al, *J Org Chem* (1977) 42:703706; Stirchak, E. P., et al, *J Org Chem* (1987) 52:4202-4206; Coull, J. M., et al, *Tet Lett* (1987) 28:745; Wang, H., et al, *Tet Lett* (1991) 32:7385-7388; US91/03680; WO 91/15500; WO 89/12060, incorporated herein by reference in their entirety). Except where specifically indicated, the substitute linkages, such as a formacetal linkage, —O—CH$_2$—O—, are linked to either the 3' or 2' carbon of a nucleomonomer on the left side of the formula and to the 5' carbon of a nucleomonomer on the right side. Thus a formacetal linkage can be indicated as 3' —O—CH$_2$—O— 5' or 2'—O—CH$_2$—O— 5'. The designations of a 3', 2' or 5' carbon can be modified accordingly when a structure other than ribose, deoxyribose or arabinose is linked to an adjacent nucleomonomer. Such structures include xylose, a hexose, morpholino ring, carbocyclic ring (e.g. cyclopentane) and the like.

Riboacetal and formacetal linkages are disclosed in Ser. No. 7/990,848, 07/690,786, 07/763,130, 07/806,710, and PCT/US92/10793 all of which are incorporated herein by reference, and include formacetal linkages such as: 3'-thioformacetal (3'—S—CH$_2$—O—5'), 2'-thioformacetal (2'—S—CH$_2$—O—5'), formacetal (3'—O—CH$_2$—O—5'), 3'-amino (3'—N-H—CH$_2$—CH$_2$—5'), 3'-thioketal (3'—S—C(R$^8$-)$_2$—O—5'), and ketal 3'—O—C(R$^8$)$_2$—O—5' where R$^8$ is CH$_2$F or, when both R$^8$ are taken together with the atom to which they are attached, form a 4-membered ring or a 6-membered ring where (R$^8$)$_2$ is —CH$_2$—X$^2$—CH$_2$—, or —CH$_2$—CH$_2$—X$^2$—CH$_2$—CH$_2$—; and wherein X$^2$ is S, SO, SO$_2$, O, CF$_2$, CHF, NH, NMe, NEt or NPr. U.S. patent application Ser. No. 690,786, filed Apr. 24, 1991, the entirety of which is incorporated by reference, describes modified linkages of the formula —Y'CX'$_2$Y'- wherein Y' is independently O or S and wherein each X' is a stabilizing substituent and independently chosen.

Modifications of oligomers that enhance their affinity for target molecules will generally improve the therapeutic potential for those compounds. Previous approaches to improve binding affinity for complementary nucleic acids have centered primarily on (i) covalent linkage of intercalating agents to oligomers (Asseline, U., et al, *Proc Natl Acad Sci* (1984) 81:3297-3401), (ii) introduction of modified bases to form more stable base pairs (Inoue, H. et al, *Nucl Acids Res* (1985) 13:7119) and (iii) altering the charge characteristics of oligomer internucleotide linkages (Letsinger, R. L. et al, *J Am Chem Soc* (1988) 110:4470).

Oligomers comprising acyclic nucleomonomer residues linked via amide bonds have been described (Nielsen, P. E., et al, *Science* (1991) 254:1497-1500; 07/894,397; WO 92/20702; 07/889,736; 07/894,397). In some cases, an invention oligomer may contain a domain comprising such linkages and a domain comprising the invention linkages. In preferred embodiments, invention oligomers will not comprise any acyclic nucleomonomer residues linked via amide bonds.

Oligomers can contain one or more 2', 5' linkages of the formula (W,Y)—Q—(Z—Q)$_{2n}$—(W,Y), where each W, Y and Z is

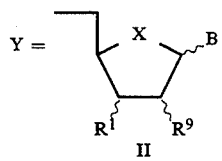

II

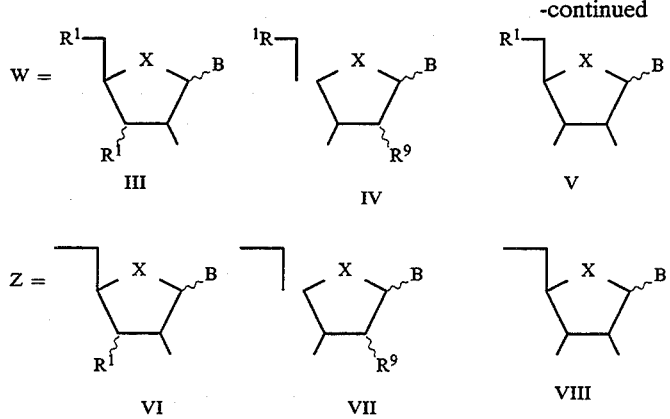

where X is S, O, CH$_2$, CHF or CF$_2$; X$^1$ is O or S; R$^1$ is an oligomer or where R$^1$ is on a terminal group of the oligomer, R$^1$ may additionally be a blocking group including PO$_3^{-2}$, DMTO, MMTO, H-phosphonate (OPO$_2$H), methylphosphonate (OPO$_3$CH$_3$), methylphosphonamidite, alkylphosphoramidite (C$_1$-C$_9$ alkyl), or a phosphoramidite such as β-cyanoethylphosphoramidite; R$^9$ independently is —O—alkyl (C$_1$-C$_{12}$), —S—alkyl (C$_1$-C$_{12}$), H, OH, OCH$_3$, SCH$_3$, OCH$_2$CHCH$_2$ (O-allyl), OC$_3$C$_7$ (O-propyl), SCH$_2$CHCH$_2$, fluorine (F) an oligomer or a blocking group; B is independently a base, and Q is independently a substitute linkage shown in Table 1 and; (2n is 1-100, preferably 2-28, but where each Q and each Z in each mer (n) is independently selected. The designation (W, Y) means that either W or Y is linked to Q at the indicated positions. In oligomer embodiments comprising a 2′,5′ substitute linkage, a maximum of 20% of the linkages give rise to inversion of oligomer polarity. Substitute linkages that invert polarity occur when there is a 5′ to 5′, 3′ to 2′ or 3′, or 2′ to 3′ or 2′ linkage between adjacent nucleomonomer residues. The preferred linkage type for the majority of linkages and substitute linkages in most oligomers is thus 3′ or 2′ to 5′. R$^9$ will generally a radical as defined for R$^2$, but in oligomer embodiments comprising for example, a 2′,5′ substitute linkage or inverted polarity oligomer, R$^9$ can be an oligomer or blocking group.

In preferred embodiments nucleomonomers of structure VIII are included in oligomers linked to an adjacent nucleomonomer through a riboacetal substitute linkage. In other embodiments where VIII is not linked via a riboacetal-type substitute linkage as described in U.S. Ser. No. 92/10793, or as circular or branched oligomers which are useful in oligonucleotide based therapies or diagnostic applications.

TABLE 1

| | |
|---|---|
| —N(R$^6$)—CH$_2$— | —CH$_2$—N(R$^6$)— |
| —N(R$^6$)—N(R$^6$)— | —N(R$^6$)—CH$_2$—CH$_2$— |
| —CH$_2$—N(R$^6$)—CH$_2$— | —CH$_2$—CH$_2$—N(R$^6$)— |
| —N(R$^6$)—N(R$^6$)—CH$_2$— | —N=C(NH$_2$)—N(R$^6$)— |
| —O—CH$_2$— | —CH$_2$—O— |
| —O—CH$_2$—CH$_2$— | —CH$_2$—O—CH$_2$— |
| —CH$_2$—CH$_2$—O— | —O—CH$_2$—O— |
| —S—CH$_2$—O— | —O—CH$_2$—S— |
| —S—CH$_2$—S— | —S—CH$_2$—S(O)(O)— |
| —S—CH$_2$— | —CH$_2$—S— |
| —S(O)—CH$_2$— | —S(O)(O)—CH$_2$— |
| —CH$_2$—S(O)— | —CH$_2$—S(O)(O)— |
| —S—CH$_2$—CH$_2$— | —S(O)—CH$_2$—CH$_2$— |
| —S(O)(O)—CH$_2$—CH$_2$— | —CH$_2$—CH$_2$—S(O)(O)— |
| —CH$_2$—S(O)(O)—CH$_2$— | —CH$_2$—S—CH$_2$— |
| —CH$_2$—CH$_2$—S— | —S(O)—CH$_2$—S— |

TABLE 1-continued

| | |
|---|---|
| —S(O)(O)—CH$_2$S(O)(O)— | —N(R$^6$)—C(O)—S— |
| —N(R$^6$)—C(S)—S— | —N(R$^6$)—C(S)—N(R$^6$)— |
| —N(R$^6$)—C(O)—N(R$^6$)— | —S—C(O)—N(R$^6$)— |
| —S—C(S)—N(R$^6$)— | —N(R$^6$)—O— |
| —O—N(R$^6$)— | —N(R$^6$)—O—CH$_2$— |
| —N(R$^6$)—CH$_2$—O— | —O—C(O)—N(R$^6$)— |
| —O—C(S)—N(R$^6$)— | —N(R$^6$)—C(O)—O— |
| —N(R$^6$)—C(S)—O— | —CH$_2$—N(R$^6$)—O— |
| —O—N(R$^6$)—CH$_2$— | —O—CH$_2$—N(R$^6$)— |
| —CH$_2$—O—N(R$^6$)— | —N(R$^6$)—S(O)— |
| —N(R$^6$)—S(O)(O)— | —S(O)—N(R$^6$)— |
| —S(O)(O)—N(R$^6$)— | —N(R$^6$)—S(O)—CH$_2$— |
| —N(R$^6$)—S(O)(O)—CH$_2$— | —N(R$^6$)—CH$_2$—S— |
| —N(R$^6$)—CH$_2$—S(O)— | —N(R$^6$)—CH$_2$—S(O)(O)— |
| —N(R$^6$)—S(O)(O)— | —S(O)(O)—N(R$^6$)— |
| —S—N(R$^6$)—CH$_2$— | —S(O)—N(R$^6$)—CH$_2$— |
| —S(O)(O)—N(R$^6$)—CH$_2$— | —CH$_2$—N(R$^6$)—S— |
| —CH$_2$—N(R$^6$)—S(O)— | —CH$_2$—N(R$^6$)—S(O)(O)— |
| —S—CH$_2$—N(R$^6$)— | —S(O)—CH$_2$N(R$^6$)— |
| —S(O)(O)—CH$_2$—N(R$^6$)— | —CH$_2$—S—N(R$^6$)— |
| —CH$_2$—S(O)—N(R$^6$)— | —CH$_2$—S(O)(O)—N (R$^6$)— |
| —N(R$^6$)—S(O)(O)—N(R$^6$)— | —N(R$^6$)—S(O)(O)—O— |
| —O—S(O)(O)—N(R$^6$)— | —O—S(O)(O )—O— |
| —N(R$^6$)—S(O)(O)—N(R$^6$)— | —CH$_2$—S (O)(O)—O— |
| —O—CH$_2$—S(O)(O)— | —S(O)—CH$_2$O— |
| —O—CH$_2$—S(O)— | —O—C(R$^8$)$_2$—O— |
| —S—C(R$^8$)$_2$—O— | —O—C(R$^8$)$_2$—S— |
| —O—CH$_2$—C≡C— | —S—CH$_2$—C≡C— |
| —O—CH$_2$—CH= (cis and trans isomers) | |
| —S—CH$_2$—CH= (cis and trans isomers) | |

For the 2′,5′ linkages in Table 1, the atom on the left side of the structure is attached to the 2′ carbon of a nucleomonomer and the atom on the right side is attached to the 5′ carbon of an adjacent nucleomonomer, R$^6$ is H, lower alkyl (1-6C), including methyl, ethyl, propyl, isopropyl and butyl, OMe, OH, heteroalkyl (1-6C, 1-2 halo, S, N or O heteroatoms), or aryl (3-6C); and wherein R$^8$ is CH$_2$F, or when both R$^8$ are taken together with the atom to which they are attached, form a 4-membered or 6-membered ring where (R$^8$)$_2$ is —CH$_2$—X$^5$—CH$_2$—, —(CH$_2$)$_2$—X$^5$—(CH$_2$)$_2$—; wherein X$^5$ is selected from the group consisting of NH, NMe, NEt, NPr, S, SO, SO$_2$, O, CF$_2$ and CHF as described (U.S. Ser. No. 07/892,902, PCT/US93/05202).

Contemplated equivalents of 2′,5′ linkages include 3 or 4 atom substitute linkages where the methylene group at the 5′ position is substituted with CO, CS, CNH$_2$, COH, CSH and the like as described in PCT/US92/04294.

Nucleosides.

Exemplary nucleosides suitable for synthesis of amide linked nucleomonomers have been described (Nielsen, P. E. ibid; WO 92/20702; 07/889,736 and 07/894,397 all applications incorporated herein by reference in their entirety). "Nucleosides" also include those moieties which contain modifications of the sugar, for example, wherein one or more of the hydroxyl groups are replaced with halogen, aliphatic groups, or functionalized as ethers, amines, and the like. Such structures include a hexose, morpholino ring, carbocyclic ring (e.g. cyclopentane) and the like.

Base.

Suitable bases for use within the present invention include not only the known purine and pyrimidine bases, but also analogs of these heterocyclic bases and tautomers thereof. Such analogs include alkylated purines or pyrimidines, acylated purines or pyrimidines, or other heterocycles. Such "analogous purines" and "analogous pyrimidines" or purine or pyrimidine analogs are those generally known in the art. An exemplary, but not exhaustive, list includes $N^4,N^4$-ethanocytosine, 7-deaza-7-methylguanine, 7-deaza-7-methyladenine, 7-deaza-7-(1-propynyl)guanine, 7-deaza-7-(1-propynyl)adenine, 7-deazaxanthine, 7-deazaguanine, 8-oxo-$N^6$-methyladenine, 4-acetylcytosine, 5-(carboxyhydroxylmethyl) uracil, 5-fluorouracil, 5-bromouracil, 5-carboxymethylaminmethyl-2-thiouracil, 5-carboxmethylaminmethyl uracil, inosine, $N^6$-isopentenyl-adenine, 1-methyladenine, 2-methylguanine, 5-methylcytosine, $N^6$-methyladenine, 7-methylguanine, 5-methylaminomethyluracil, 5-methoxy aminomethyl-2-thiouracil, 5-methoxyuracil, pseudouracil, 5-methyl-2-thiouracil, 2-thiouracil, 4-thiouracil, 5-(1-propynyl)-4-thiouracil, 5-(1-propynyl)-2-thiouracil, 5-(1-propynyl)-2-thiocytosine, 2-thiocytosine, 6-azacytosine, 6-azathymidine and 5-trifluoromethyluracil, 2,6-diaminopurine, phenothiazine tricyclic cytidine, phenoxazine tricyclic cytidine, benzene tricyclic cytidine or 2-pyridine tricyclic cytidine. Some of the base analogs and their use in oligomers have been described (see for example, U.S. Ser. Nos. 92/10115; 91/08811; 92/09195; WO 02258; Nikiforov, T. T., et al, *Tet Lett* (1992) 33:2379–2382; Clivio, P., et al, *Tet Lett* (1992) 33:65–68; Nikiforov, T. T., et al, *Tet Lett* (1991) 32:2505–2508; Xu, Y.-Z., et al, *Tet Lett* (1991) 32:2817–2820; Clivio, P., et al, *Tet Lett* (1992) 33:69–72; Connolly, B. A., et al, *Nucl Acids Res* (1989) 17:49574974).

Preferred bases include adenine, guanine, thymine, uracil, cytosine, 5-methylcytosine, 5-(1-propynyl)uracil, 5-(1-propynyl)cytosine, 7-deazaxanthosine, 7-deaza-7-methylguanine and 7-deaza-7-methyladenine.

Bases also include the pyrimidine derivatives described in U.S. Ser. No. 08/123,505, incorporated herein by reference, of the formula IX:

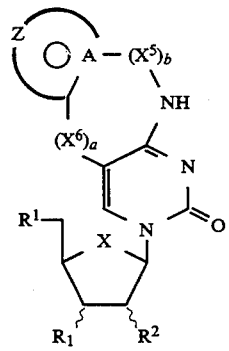

wherein $R^1$, $R^2$ and X are as defined above;

a and b are 0 or 1, provided that the total of a and b is 0 or 1;

A is N or C;

$X^6$ is S, O, —C(O)—, NH or NCH$_2$R$^{12}$;

$X^5$ is —C(O)—;

Z is taken together with A to form an aryl or heteroaryl ring structure comprising 5 or 6 ring atoms wherein the heteroaryl ring comprises a single O ring heteroatom, a single N ring heteroatom, a single S ring heteroatom, a single O and a single N ring heteroatom separated by a carbon atom, a single S and a single N ring heteroatom separated by a carbon atom, 2 N ring heteroatoms separated by a carbon atom, or 3 N ring heteroatoms at least two of which are separated by a carbon atom, and wherein the aryl or heteroaryl ring carbon atoms are unsubstituted with other than H or at least 1 nonbridging ring carbon atom is substituted with $R^{12}$ or =O;

$R^{13}$ is a protecting group or H;

$R^{12}$ is independently H, C$_1$-C$_6$ alkyl, C$_2$-C$_6$ alkenyl, C$_2$-C$_6$ alkynyl, NO$_2$, N(R$^{13}$)$_2$, C≡N or halo, or an $R^{12}$ is taken together with an adjacent $R^{12}$ to complete a ring containing 5 or 6 ring atoms, and tautomers, solvates and salts thereof. The compounds of structure (IX) are made through several intermediates as described. The 4-pyridones are obtained from an intermediate having structure (X)

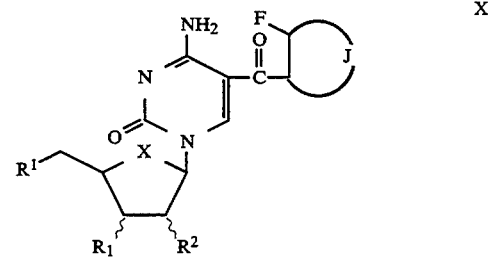

wherein $R^1$, $R^2$ and X are as defined above;

J is an aryl or heteroaryl ring structure comprising 5 or 6 ring atoms wherein the heteroaryl ring comprises a single O ring heteroatom, a single N ring heteroatom, a single S ring heteroatom, a single O and a single N ring heteroatom separated by a carbon atom, a single S and a single N ring heteroatom separated by a carbon atom, or 2 N ring heteroatoms separated by a carbon atom, and wherein the aryl or heteroaryl ring carbon atoms are unsubstituted with other than H or at least 1 nonbridging ring carbon atom is substituted with $R^{12}$; and $R^{12}$ is defined above; and tautomers, salts and solvates thereof.

The 2-pyridones are synthesized from the intermediates of structures (XI) and (XII):

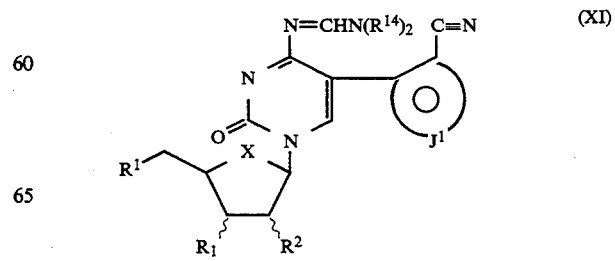

wherein $R^1$, $R^2$ and X are as defined above;

$R^{14}$ is $C_1$–$C_3$ alkyl; and $J^1$ is an aryl or heteroaryl ring structure comprising 5 or 6 ring atoms wherein the heteroaryl ring comprises a single O ring heteroatom, a single N ring heteroatom, a single S ring heteroatom, a single O and a single N ring heteroatom separated by a carbon atom, a single S and a single N ring heteroatom separated by a carbon atom, or 2 N ring heteroatoms separated by a carbon atom, and wherein the aryl or heteroaryl ring carbon atoms are unsubstituted with other than H or at least 1 nonbridging ring carbon atom is substituted with $C_1$–$C_6$ alkyl, $C_2$–$C_6$ alkenyl, $C_2$–$C_6$ alkynyl, $NO_2$, $N(R^{13})_2$, or halo;

$R^{13}$ is a protecting group or H;

and tautomers, solvates and salts thereof.

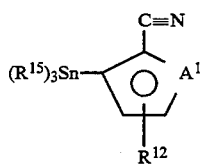

(XII)

wherein $A^1$ is independently S, O, N or $CR^{12}$;

$R^{12}$ is defined above; and $R^{15}$ is $C_1$–$C_4$ alkyl; and tautomers, salts and solvates thereof.

Phenoxazines and oxadiazines also are made from the intermediate (XIII), as are pyridinopyrrolines, thiazines and oxazines.

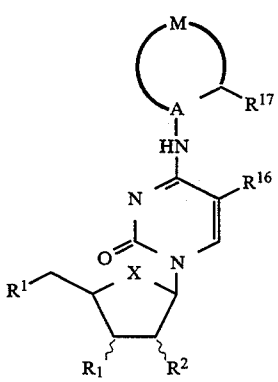

(XIII)

wherein $R^1$, $R^2$, A and X are as defined above;

$R^{16}$ is independently halo or $C_1$–$C_2$ haloalkyl;

$R^{17}$ is independently —SH, —OH, =S or =O;

A is independently N or C; and

M, taken together with the radical —A—C(—$R^{17}$), completes an aryl or heteroaryl ring structure comprising 5 or 6 ring atoms wherein the heteroaryl ring comprises a single O ring heteroatom, a single N ring heteroatom, a single S ring heteroatom, a single O and a single N ring heteroatom separated by a carbon atom, a single S and a single N ring heteroatom separated by a carbon atom, 2 N ring heteroatoms separated by a carbon atom, or 3 N ring heteroatoms at least two of which are separated by a carbon atom, and wherein the aryl or heteroaryl ring carbon atoms are unsubstituted with other than H or at least 1 nonbridging ring carbon atom is substituted with $R^{12}$; and $R^{12}$ is defined above, and tautomers, solvates and salts thereof.

The phenopyrrolines are made by the use of the intermediate of structure (XIV)

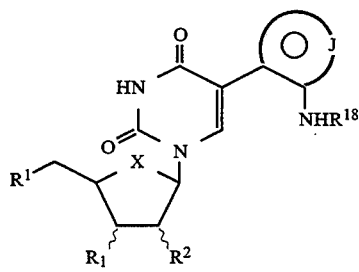

XIV wherein $R^1$, $R^2$ and X are as described above;

J is an aryl or heteroaryl ring structure comprising 5 or 6 ring atoms wherein the heteroaryl ring comprises a single O ring heteroatom, a single N ring heteroatom, a single S ring heteroatom, a single O and a single N ring heteroatom separated by a carbon atom, a single S and a single N ring heteroatom separated by a carbon atom, or 2 N ring heteroatoms separated by a carbon atom, andwherein the aryl or heteroaryl ring carbon atoms are unsubstituted with other than H or at least 1 nonbridging ring carbon atom is substituted with $R^{12}$;

$R^{12}$ is defined above; $R^{18}$ is a protecting group; and tautomers, salts and solvates thereof.

Synthesis of representative compounds of formula IX is shown in FIGS. 31 to 37. Oligomers having bases of structure IX that are capable of forming high melting duplexes with complementary sequences are useful in numerous processes, including diagnostics. High melting duplexes are those having melting temperatures substantially above the melting temperatures of oligonucleotide or nucleic acid duplexes of the same sequence that contain the ordinary, naturally occuring bases, e.g., adenosine, cytidine, uridine, guanosine, thymidine and the like. "Substantially above" means that the derivative oligonucleotide, when hybridized with its complementary sequence, will not dissociate from the duplex until the temperature is raised from about 2° to 40° C., ordinarily about 8 to 40° C., above the dissociation temperature of the same oligonucleotide having the analogous normal A, C, U, G or T bases, but to no greater temperature than about 95° C. This is known as the Δ Tm. Ordinarily, Δ Tm is measured by comparing control oligonucleotide binding to complementary RNA with the binding of test oligonucleotide to the same KNA, following the method described in Jones et al, *J Org Chem* (1993) 58:2983.

Nucleomonomers comprising the formula IX bases, phenothiazine deoxyriboside and phenoxazine deoxyriboside have excitation and emission wavelengths of Ex380nM/EM492nM and Ex360nM/EM450nM, respectively, and are intensely fluorescent. The compounds remain fluorescent upon incorporation into oligonucleotides and are visible intracellularly when bound to target sequences after direct injection in accord with known methods. Oligomers comprising one or more such bases can be used in various fluorescent assays to detect complementary nucleic acid sequences. The test phenoxazine oligonucletides bind to a target complementary RNA sequence upon direct injection at an $IC_{50}$ of 5–10 μM, with expression of a beta-galactosidase control gene remaining unaffected, and therefore are useful in antisense methods for inhibition of translation of target RNAs in living cells.

Covalent Bonding Moiety.

Included in some oligomer embodiments is a moiety which is capable of effecting at least one covalent bond between the oligomer and the duplex. Multiple covalent bonds can also be formed by providing a multiplicity of such crosslinking moieties. The covalent bond is preferably to a base residue in the target strand, but can also be made with other portions of the target, including the saccharide or phosphodiester. The reaction nature of the moiety which effects crosslinking determines the nature of the target in the duplex. Preferred crosslinking moieties include acylating and alkylating agents, and, in particular, those positioned relative to the sequence specificity-conferring portion so as to permit reaction with the target location in the strand. Crosslinking moieties are disclosed and claimed in commonly owned pending application Ser. No. 640,654.

Inverted Polarity.

In their most general form, inverted polarity oligomers, that can incorporate one or more nucleomonomers described above, contain at least one segment along their length of the formula: 3'-5'—C—5'-3' (1) or 5'-3'—C—3'5' (2) where —C— symbolizes any method of coupling the nucleomonomer sequences of opposite polarity (PCT/US90/06128, Froehler, B. C., et al, *Biochemistry* (1992) 31:1603–1609; Horne, D.A., et al, *J Am Chem Soc* (1990) 112:2435–2437; Beal, P. A., et al, *J Am Chem Soc* (1992) 114:4976–4978). In these formulas, the symbol 3'-5' indicates a stretch of oligomer in which the linkages are consistently formed between the 5'-hydroxyl of the ribosyl residue of the nucleomonomer to the left with the 3'-(or 2'-for oligomers having 2', 5' linkages) hydroxyl of the ribosyl residue of the nucleomonomer to the right (i.e., a region of uniform polarity), thus leaving the 5'-hydroxyl of the rightmost nucleomonomer ribosyl residue free for additional conjugation.

2' and 3' Modified Oligomers.

Oligomers within the present invention include nucleomonomers having modifications of the ribose or deoxyribose sugar. Modifications described for the 2' position are often applicable to the 3' position for 2',5' linked oligomers. 2'—O—methyl-, 2'—O—ethyl- and 2'—O—allyl oligomers have been synthesized and shown to bind to single-stranded complementary nucleic acid sequences (Cotten, M., et al, *Nucleic Acids Res* (1990) 19:2629–2635; Blencowe, B. J., et al, *Cell* (1989) 59:531–539; Sproat, B. S., et al, *Nucleic Acids Res* (1989) 17:3373–3386; Inoue, H., et al, *Nucleic Acids Res* (1987) 15:6131–6148; Morisawa, H., et al, European Patent Serial No. 0339842; Chavis, C., et al, *J Organic Chem* (1982) 47:202–206; Sproat, B.S., et al, *Nucleic Acids Res* (1991) 19:733–738). The 2'-modified oligomers were reported to be relatively nuclease stable compared to unmodified controls. Synthesis of 2' fluoro nucleomonomers and their incorporation into oligomers has also been described (Codington, J. F., et al, *J Org Chem* (1964) 29:558–564; Fazakerley, G. V., et al, *FEBS Lett* (1985) 182:365–369). Synthesis of oligomer analogs containing the modified bases described herein would be based on methods described. Synthesis of oligomers containing 2'-amino nucleomonomers has been described (Pieken, W. A., et al, *Science* (1991) 253:314–317). In an additional use of substitute linkages of the invention, 2'- or 3'—O—allyl modified sugar forms of the nucleomonomers can be included in the oligomer. The 2'- and 3'—O—allyl nucleomonomers can be prepared and incorporated into oligomers using standard methods.

Synthesis.

Oligomers or the segments thereof are conventionally synthesized. The synthetic methods known in the art and described herein can be used to synthesize oligomers containing substitute linkages of the invention, as well as other linkages or substitute linkages known in the art, using appropriately protected nucleomonomers. Methods for the synthesis of oligomers having phosphorous containing linkages are found, for example, in Froehler, B., et al, *Nucleic Acids Res* (1986) 14:5399–5467; *Nucleic Acids Res* (1988) 16:4831–4839; *Nucleosides and Nucleotides* (1987) 6:287–291; Froehler, B., *Tetrahedron Letters* (1986) 27:5575–5578; Caruthers, M. H. in Oligodeoxynucleotides-Antisense Inhibitions of Gene Expression (1989), J. S. Cohen, editor, CRC Press, Boca Raton, p7–24; Reese, C. B. et al, *Tetrahedron Letters* (1985) 26:2245–2248. Synthesis of the methylphosphonate linked oligomers via methyl phosphonamidite chemistry has also been described (Agrawal, S. et al, *Tetrahedron Letters* (1987) 28:3539–3542; Klem, R. E., et al, WO 92/07864).

Oligomers containing nonphosphorous based substitute linkages that have been previously described in commonly owned pending applications nos. 07/874,334, PCT/US90/06110 and PCT/US91/06855 are preferably synthesized using suitably blocked dimer synthons as a starting material Oligomers containing linkages of the present invention are also conveniently synthesized by preparation of dimer or trimer compounds by solution phase chemistry followed by conversion of the synthon to a derivative that is incorporated into oligomers by either solid or solution phase chemistry. Typical synthons are 5' DMT or MMT blocked 3' phosphonate or phosphoramidate derivatives which are prepared by standard methods (see: Gait, M. J. ed., Oligonucleotide Synthesis; A Practical Approach (1984) IRL Press, Oxford).

Oligomers having phosphorous-containing linkages or segments thereof are conventionally synthesized. Methods known in the art and described herein can be used to synthesize oligomers containing bases of the invention, as well as other bases known in the art, using appropriately protected nucleomonomers. Methods for the synthesis of oligomers are found, for example, in Froehler, B., et al, *Nucleic Acods Res* (1986) 14:5399–5467; *Nucleic Acids Res* (1988) 16:4831–4839; *Nucleosides and Nucleotides* (1987) 6:287–291; Froehler, B., *Tetrahedron Letters* (1986) 27:5575–5578; Caruthers, M. H. in Oligodeoxynucleotides-Antisense Inhibitions of Gene Expression (1989), J. S. Cohen, editor, CRC Press, Boca Raton, 7–24; Reese, C. B. et al, *Tetrahedron Letters* (1985) 26:2245–2248. Synthesis of the methylphosphonate linked oligomers via methyl phosphonamidite chemistry has also been described (Agrawal, S. et al, *Tetrahedron Letters* (1987) 28:3539–3542; Klem, R. E., et al, International Publication Number WO 92/07864). Synthons that are included in the scope of the present invention include dimers, trimers, tetramers, hexamers and longer oligomers made by solid or solution phase synthesis. Trimers and longer synthons may contain more than one type of linkage. The synthons may include any base as described above or 2', 3' and 5' groups such as OH, DMTO, MMTO, O-allyl, phosphate, a phosphonate or an amidite as described above.

Utility and Administration.

As the oligomers of the invention are capable of significant single-stranded or double-stranded target nucleic acid binding activity to form duplexes, triplexes or other forms of stable association, these oligomers are useful in diagnosis or detection of complementary nucleic acid sequences that are associated with expression of one or more genes such as those associated with pathological conditions. Exemplary genes or RNAs encoded by those genes that can be targeted include those that encode enzymes, hormones, serum proteins, transmembrane proteins, adhesion molecules (LFA-1, GPIIb/IIIa, ELAM-1, VACM-1, ICAM-1, E-selectin, and the like), receptor molecules including cytokine receptors, cytokines (IL-1, IL-2, IL-3, IL-4, IL-6 and the like), oncogenes, growth factors, and interleukins. Target genes or RNAs can be associated with any pathological condition such as those associated with inflammatory conditions, cardiovascular disorders, immune reactions, cancer, viral infections, bacterial infections, yeast infections, parasite infections and the like. Target genes or RNAs encoded by those genes that can serve as targets for cancer treatments include oncogenes, such as ras, k-ras, bcl-2, c-myb, bcr, c-myc, c-abl or overexpressed sequences such as mdm2, oncostatin M, IL-6 (Kaposi's sarcoma), HER-2 and translocations such as bcr/abl. Viral gene sequences or RNAs encoded by those genes such as polymerase or reverse transcriptase genes of herpesviruses such as CMV, HSV-1, HSV-2, retroviruses such as HTLV-1, HIV-1, HIV-2, or other DNA or RNA viruses such as HBV, HPV, VZV, influenza virus, adenoviruses, flaviviruses, rhinovirus and the like are also suitable targets. Application of specifically binding oligomers can be used in conjunction with other therapeutic treatments.

Delivery of oligomers of the invention into cells can be enhanced by any suitable method including calcium phosphate, DMSO, glycerol or dextran transfection, electroporation or by the use of cationic anionic and/or neutral lipid compositions or liposomes by methods described (International Publication Nos. WO 90/14074, WO 91/16024, WO 91/17424, U.S. Pat. No. 4,897,355). The oligomers can be introduced into cells by complexation with cationic lipids such as DOTMA (which may or may not form liposomes) which complex is then contacted with the cells. Suitable cationic lipids include but are not limited to N-(2,3-di(9-(Z)-octadecenyloxyl))-prop-l-yl- N,N,N-trimethylammonium (DOTMA) and its salts, 1—O—oleyl-2—O—oleyl-3-dimethylaminopropyl-$\beta$-hydroxyethylammonium and its salts and 1, 2-bis(oleyloxy)-3-(trimethylammonio) propane and its salts.

Enhanced delivery of the invention oligomers can also be mediated by the use of (i) viruses such as Sendai virus (Bartzatt, R., Biotechnol Appl Biochem (1989) 11:133–135) or adenovirus (Wagner, E., et al, Proc Natl Acad Sci (1992) 89:6099–6013; (ii) polyamine or polycation conjugates using compounds such as polylysine, protamine or N1, N12-bis(ethyl)spermine (Wagner, E., et al, Proc Natl Acad Sci (1991) 88:4255–4259; Zenke, M., et al, Proc Natl Acad Sci (1990) 87:3655–3659; Chank, B.K., et al, Biochem Biophys Res Commun (1988) 157:264–270; U.S. Pat. No. 5,138,045); (iii) lipopolyamine complexes using compounds such as lipospermine (Behr, J.-P., et al, Proc Natl Acad Sci (1989) 86:6982–6986; Loeffler, J. P., et al, J Neurochem (1990) 54:1812– 1815); (iv) anionic, neutral or pH sensitive lipids using compounds including anionic phospholipids such as phosphatidyl glycerol, cardiolipin, phosphatidic acid or phosphatidylethanolamine (Lee, K.-D., et al, Biochim Biophys ACTA (1992) 1103:185–197; Cheddar, G., et al, Arch Biochem Biophys (1992) 294:188–192; Yoshimura, T., et al, Biochem Int (1990) 20:697–706); (v) conjugates with compounds such as cholesterol, transferrin or biotin or (vi) conjugates with compounds such as serum proteins (including albumin or antibodies), glycoproteins or polymers (including polyethylene glycol) that enhance pharmacokinetic properties of oligomers in a subject. As used herein, transfection refers to any method that is suitable for delivery of oligomers into cells. Any reagent such as a lipid or any agent such as a virus that can be used in transfection protocols is collectively referred to herein as a "permeation enhancing agent". Delivery of the oligomers into cells can be via cotransfection with other nucleic acids such as (i) expressable DNA fragments encoding a protein(s) or a protein fragment or (ii) translatable RNAs that encode a protein(s) or a protein fragment.

RNase H "competent" or RNase H "incompetent" oligomers can be easily designed using the substitute linkages of the invention. RNase H competent oligomers can comprise one or more RNase H competent domains comprised of linked RNase H competent nucleomonomers. Oligomers having modifications such as 2'-substitutions (2'-(O—allyl and the like) or certain uncharged linkages (methylphosphonate, phosphoramidate and the like) are usually incompetent as a substrate that is recognized by and/or acted on by RNase H. RNase H competence can facilitate antisense oligomer function by degrading the target RNA in an RNA-oligomer duplex (Dagle, J. M., et al,) Nucl Acids Res (1990) 18:4751–4757; WO 89/05358). The enzyme cleaves RNA in RNA-DNA duplexes.

In order to retain RNase H competence, an oligomer requires a RNase H competent domain of three or more competent contiguous nucleomonomers located within it (Quartin, R.S., et al, Nucl Acids Res (1989) 17:7253–7262). Design of oligomers resistant to nuclease digestion will have terminal linkage, sugar and/or base modifications to effect nuclease resistance. Thus, the oligomers can be designed to have modified nucleomonomer residues at either or both the 5'- and/or 3'- ends, while having an internal RNase H competent domain. Exemplary oligomers that retain RNase H competence would generally have uniform polarity and would comprise about 2 to about 12 nucleomonomers at the 5'- end and at the 3'- end which stabilize the oligomer to nuclease degradation and about three to about 26 nucleomonomers that function as a RNase H competent domain between the RNase H incompetent 3'- and 5'- ends. Variations on such an oligomer would include (1) a shorter RNase H competent domain comprising 1 or 2 RNase H competent linkages or substitute linkages, (2) a longer RNase H incompetent domain comprising up to 15, 20 or more substitute linkages or nucleomonomers, (3) a longer RNase H competent domain comprising up to 30, 40 or more linkages, (4) oligomers with only a single RNase H incompetent domain at the 3'end or at the 5'end, or (5) oligomers having more than one RNase H competent domain. RNase H competence also applies as a consideration to oligomers having one or more regions of inverted polarity, to circular oligomers and to other types of oligomers.

Oligomers containing as few as about 8 nucleomonomers can be used to effect inhibition of target protein(s) expression by formation of duplex or triplex structures with target nucleic acid sequences. However, linear oligomers used to inhibit target protein expression via duplex or triplex formation will preferably have from about 10 to about 20 nucleomonomer residues.

Oligomers containing substitute linkages of the invention can be conveniently circularized as described (International Publication No. WO 92/19732; Kool, E. T. *J Am Chem Soc* (1991) 113:6265-6266; Prakash, G., et al, *J Am Chem Soc* (1992) 114:3523-3527). Such oligomers are suitable for binding to single-stranded or double-stranded nucleic acid targets. Circular oligomers can be of various sizes. Such oligomers in a size range of about 22-50 nucleomonomers can be conveniently prepared. The circular oligomers can have from about three to about six nucleomonomer residues in the loop region that separate binding domains of the oligomer as described (Prakash, G. ibid). Oligomers can be enzymatically circularized through a terminal phosphate by ligase or by chemical means via linkage through the 5'- and 3'-terminal sugars and/or bases. Base recognition rules in Watson-Crick duplex binding differ from those in Hoogsteen controlled triplex binding. Because of this, the oligomer base sequence can be used to dictate the type of binding rules an oligomer will utilize.

In addition, the oligomers of the invention can be used as diagnostic reagents to detect the presence or absence of the target nucleic acid sequences to which they specifically bind. The enhanced binding affinity of the invention oligomers is an advantage for their use as primers and probes. Diagnostic tests can be conducted by hybridization through either double or triple helix formation which is then detected by conventional means. For example, the oligomers can be labeled using radioactive, fluorescent, or chromogenic labels (or any detectable label) and the presence of label bound to solid support detected. Detection of specific sequences would be accomplished by separation of unbound oligomer from bound oligomer followed by detection of the specifically bound oligomer by conventional means (autoradiography, scintillation counting, and the like). Alternatively, the presence of a double or triple helix can be detected by antibodies which specifically recognize these forms. Means for conducting assays using oligomers as probes are generally known.

Diagnostic assays based on detection of RNA for identification of bacteria, fungi or protozoa sequences often require isolation of RNA from samples or organisms grown in the laboratory, which is laborious and time consuming, as RNA is extremely sensitive to ubiquitous nucleases. The oligomer probes can also incorporate additional modifications such as modified sugars and/or substitute linkages that render the oligomer especially nuclease stable, and would thus be useful for assays conducted in the presence of cell or tissue extracts which normally contain nuclease activity. Oligomers containing terminal modifications often retain their capacity to bind to complementary sequences without loss of specificity (Uhlmann et al, *Chemical Reviews* (1990) 90:543-584). As set forth above, the invention probes can also contain linkers that permit specific binding to alternate DNA strands by incorporating a linker that permits such binding (Froehler et al, *Biochemistry* (1992) 31:1603-1609); Horne et al, *J Am Chem Soc* (1990) 112:2435-2437).

Incorporation of substitute linkages of the present invention into probes that also contain covalent crosslinking agents has the potential to increase sensitivity and reduce background in diagnostic or detection assays. In addition, the use of crosslinking agents will permit novel assay modifications such as (1) the use of the crosslink to increase probe discrimination, (2) incorporation of a denaturing wash step to reduce background and (3) carrying out hybridization and crosslinking at or near the melting temperature of the hybrid to reduce secondary structure in the target and to increase probe specificity. Modifications of hybridization conditions have been previously described (Gamper et al, *Nucleic Acids Res* (1986) 14:9943). Oligomers of the invention are suitable for use in diagnostic assays that employ methods wherein either the oligomer or nucleic acid to be detected are covalently attached to a solid support as described (U.S. Pat. No. 4,775,619). The oligomers are also suitable for use in diagnostic assays that rely on polymerase chain reaction techniques to amplify target sequences according to described methods (EP 0 393 744). Oligomers of the invention containing a 3' terminus that can serve as a primer are compatible with polymerases used in polymerase chain-reaction methods such as the Taq or Vent TM (New England Biolabs) polymerase. Oligomers of the invention can thus be utilized as primers in PCR protocols.

The oligomers are useful as primers that are discrete sequences or as primers with a random sequence. Random sequence primers can be generally about 6, 7, or 8 nucleomonomers in length. Such primers can be used in various nucleic acid amplification protocols (PCR, ligase chain reaction, etc) or in cloning protocols. The substitute linkages of the invention generally do not interfere with the capacity of the oligomer to function as a primer. Oligomers of the invention having 2'- modifications at sites other than the 3' terminal residue, other modifications that render the oligomer RNase H incompetent or otherwise nuclease stable can be advantageously used as probes or primers for RNA or DNA sequences in cellular extracts or other solutions that contain nucleases. Thus, the oligomers can be used in protocols for amplifying nucleic acid in a sample by mixing the oligomer with a sample containing target nucleic acid, followed by hybridization of the oligomer with the target nucleic acid and amplifying the target nucleic acid by PCR, LCR or other suitable methods.

The oligomers derivatized to chelating agents such as EDTA, DTPA or analogs of 1,2-diaminocyclohexane acetic acid can be utilized in various in vitro diagnostic assays as described (U.S. Pat. Nos. 4,772,548, 4,707,440 and 4,707,352). Alternatively, oligomers of the invention can be derivatized with crosslinking agents such as 5-(3-iodoacetamidoprop-1-yl)-2'-deoxyuridine or 5-(3-(4-bromobutyramido)prop-1-yl)-2'-deoxyuridine and used in various assay methods or kits as described (WO 90/14353).

All references cited herein are incorporated herein by reference in their entirety.

Synthesis Of the Oligomers.

The oligomers of the invention can be synthesized using reactions known in the art of oligonucleotide derivative synthesis. See e.g. Flandor et al *Tet Lett* (1990) 31:597-600; Mattson et al, *J Org Chem* (1990) 55:2552-2554; Chung et al, *J Org Chem* (1989) 54:2767-2769 synthesis of invention oligomers is described in Example 18 and shown in FIGS. 30-1 through 30-4.

Figure 3:
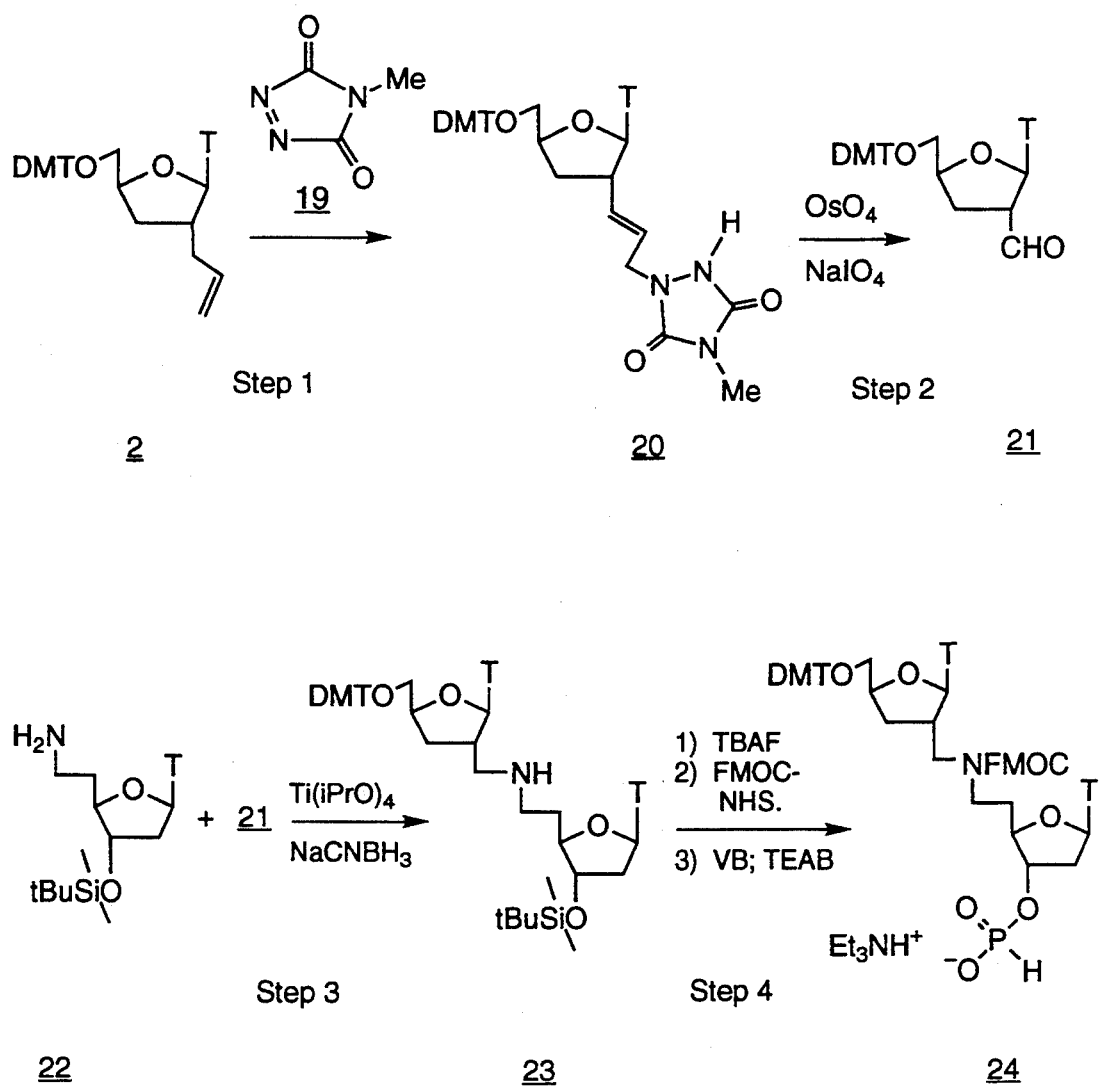
Figure 18:
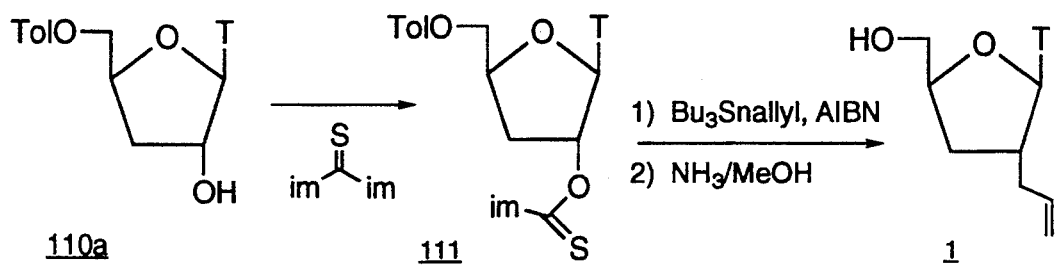
Figure 19:
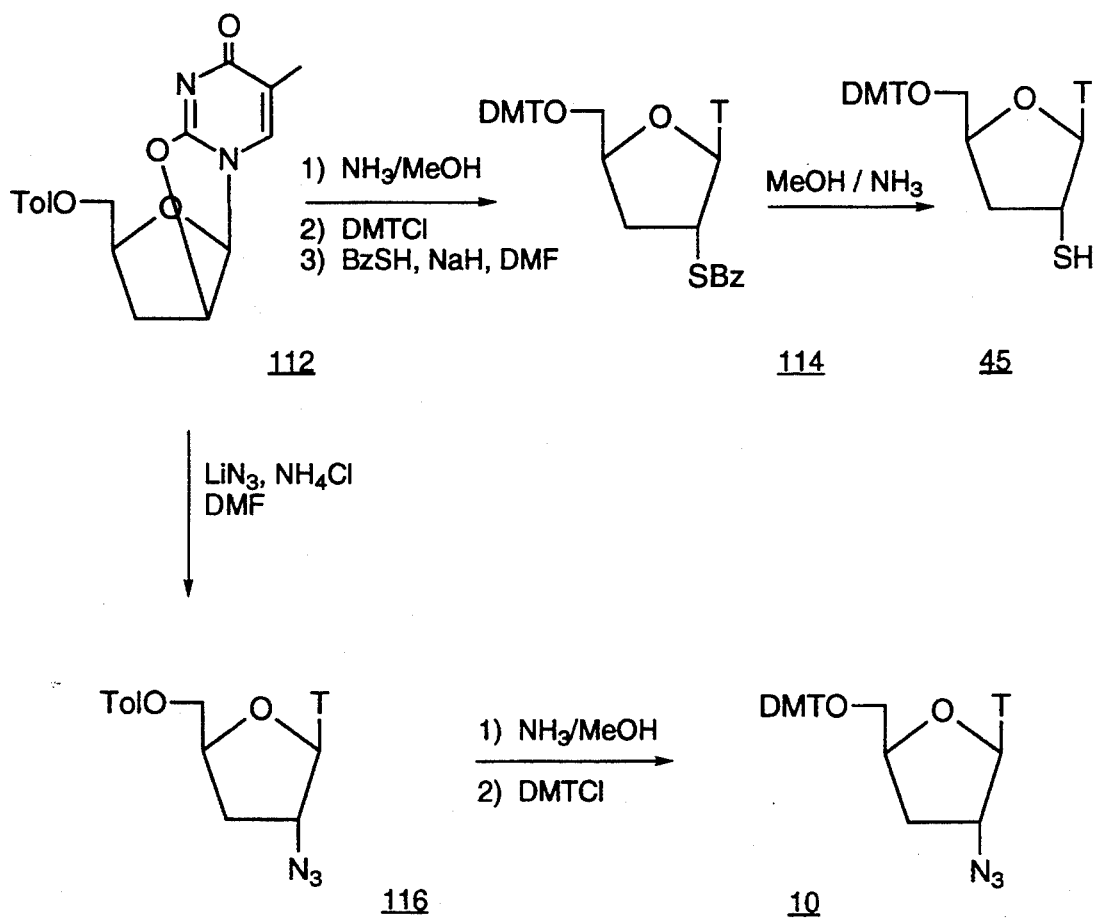
Figure 20:
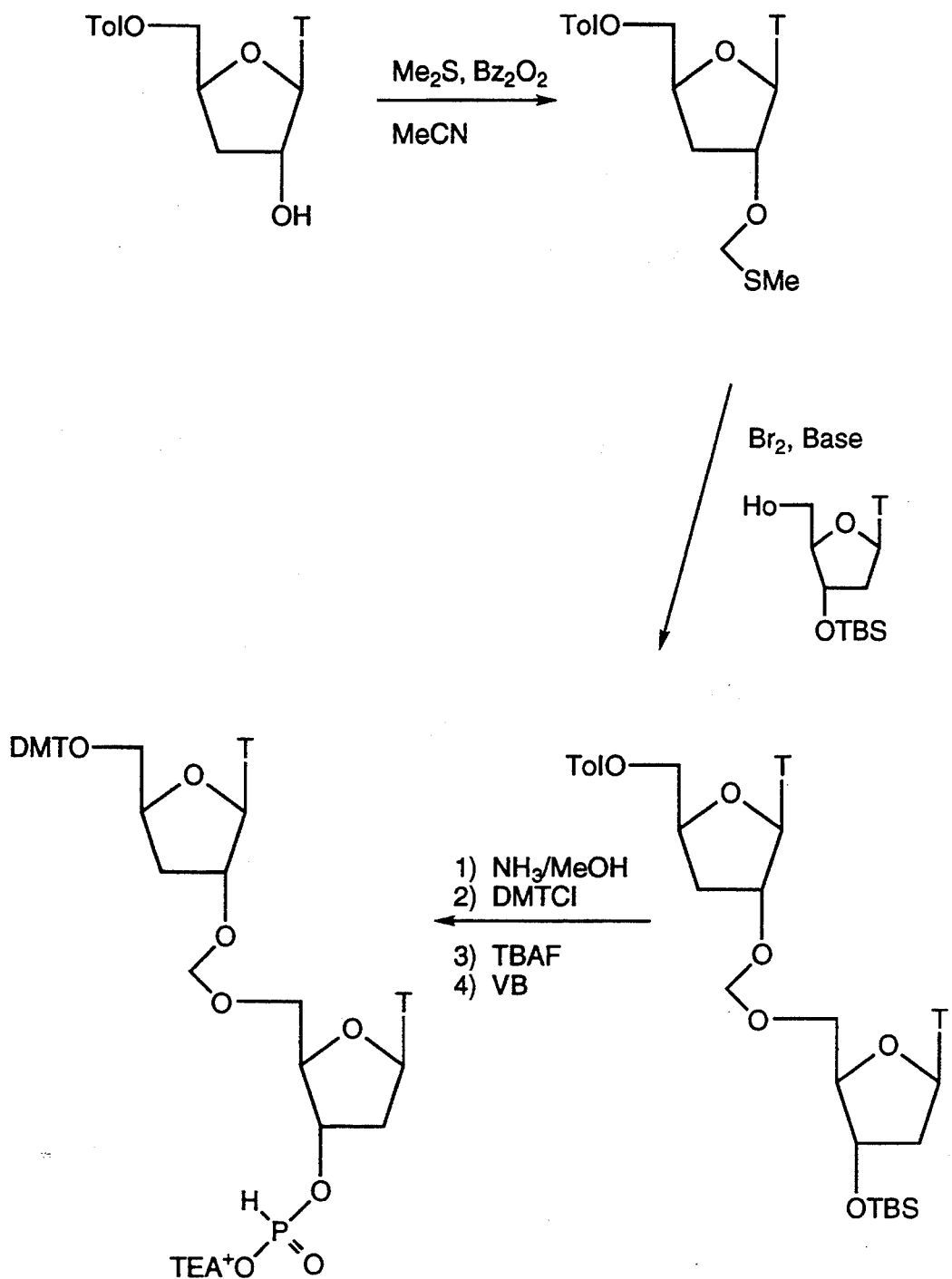
Figure 21:
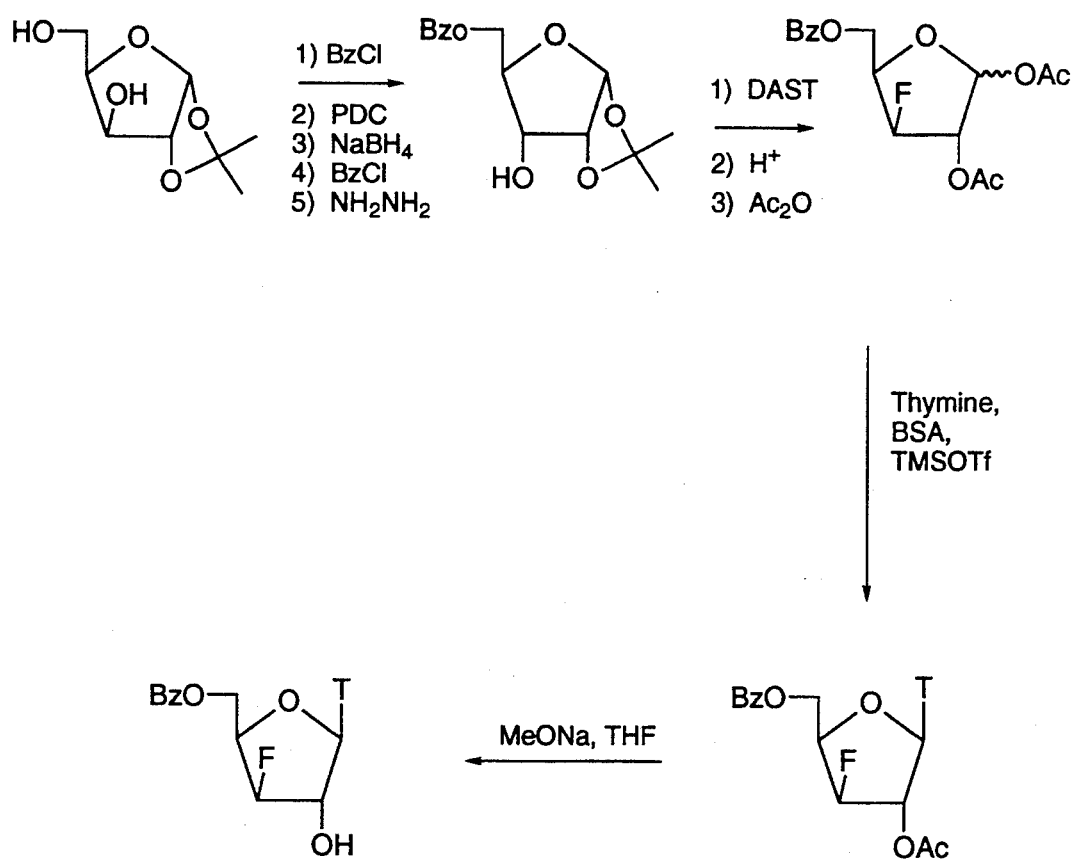
Figure 22:
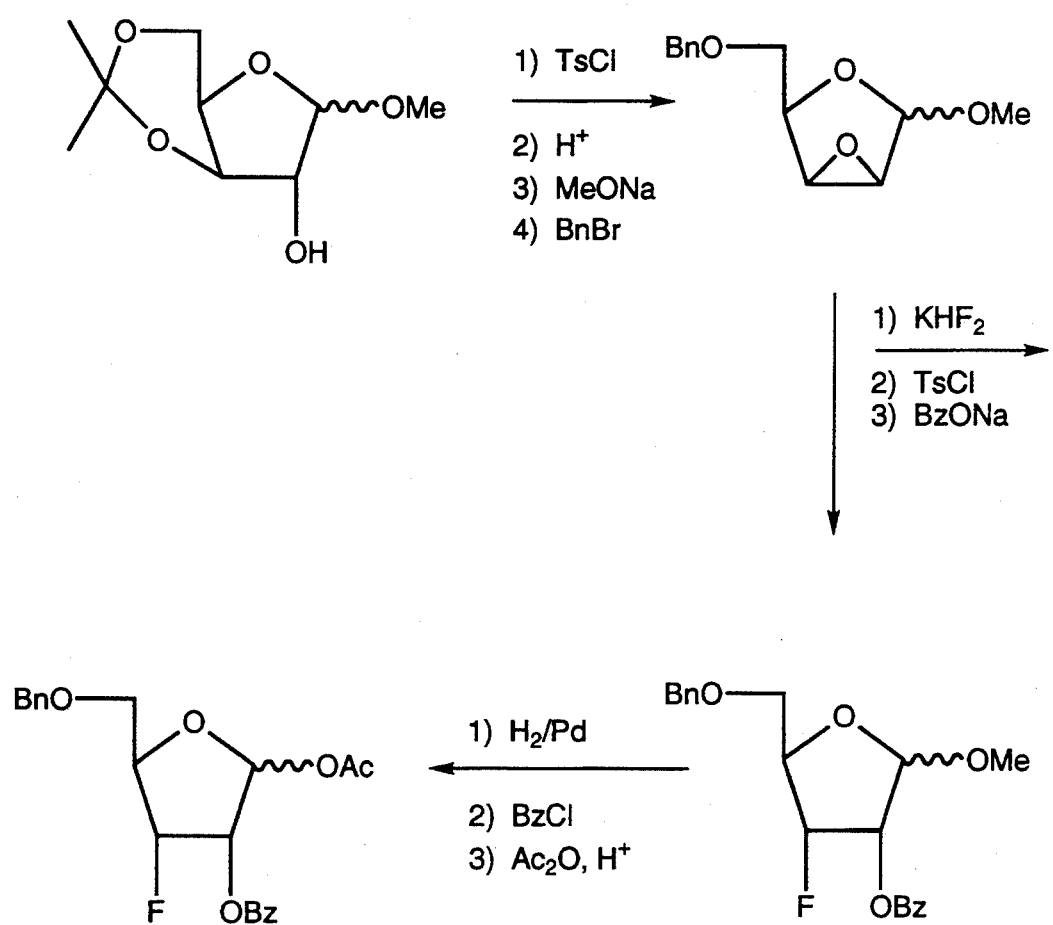
Figure 23:
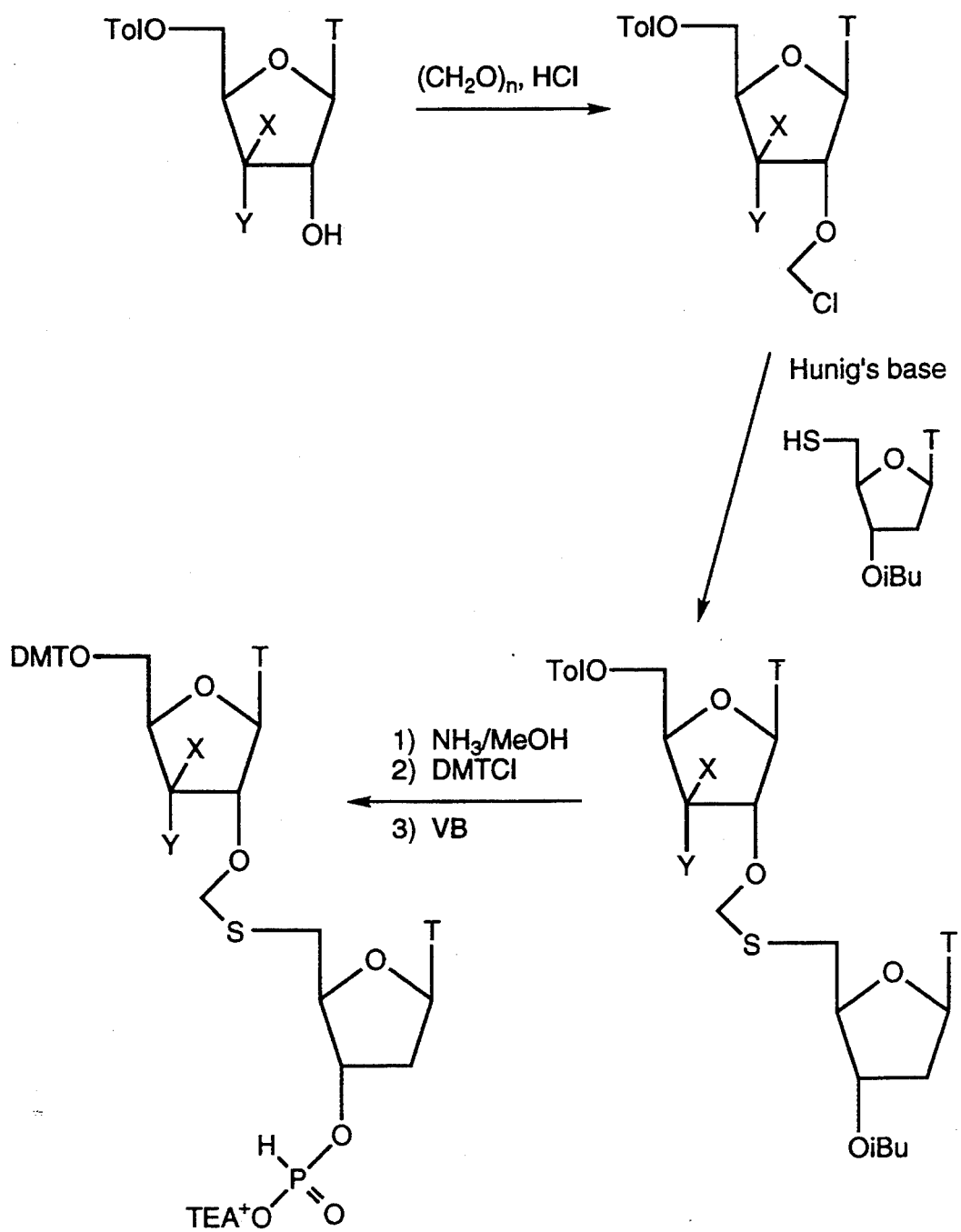
Figure 24:
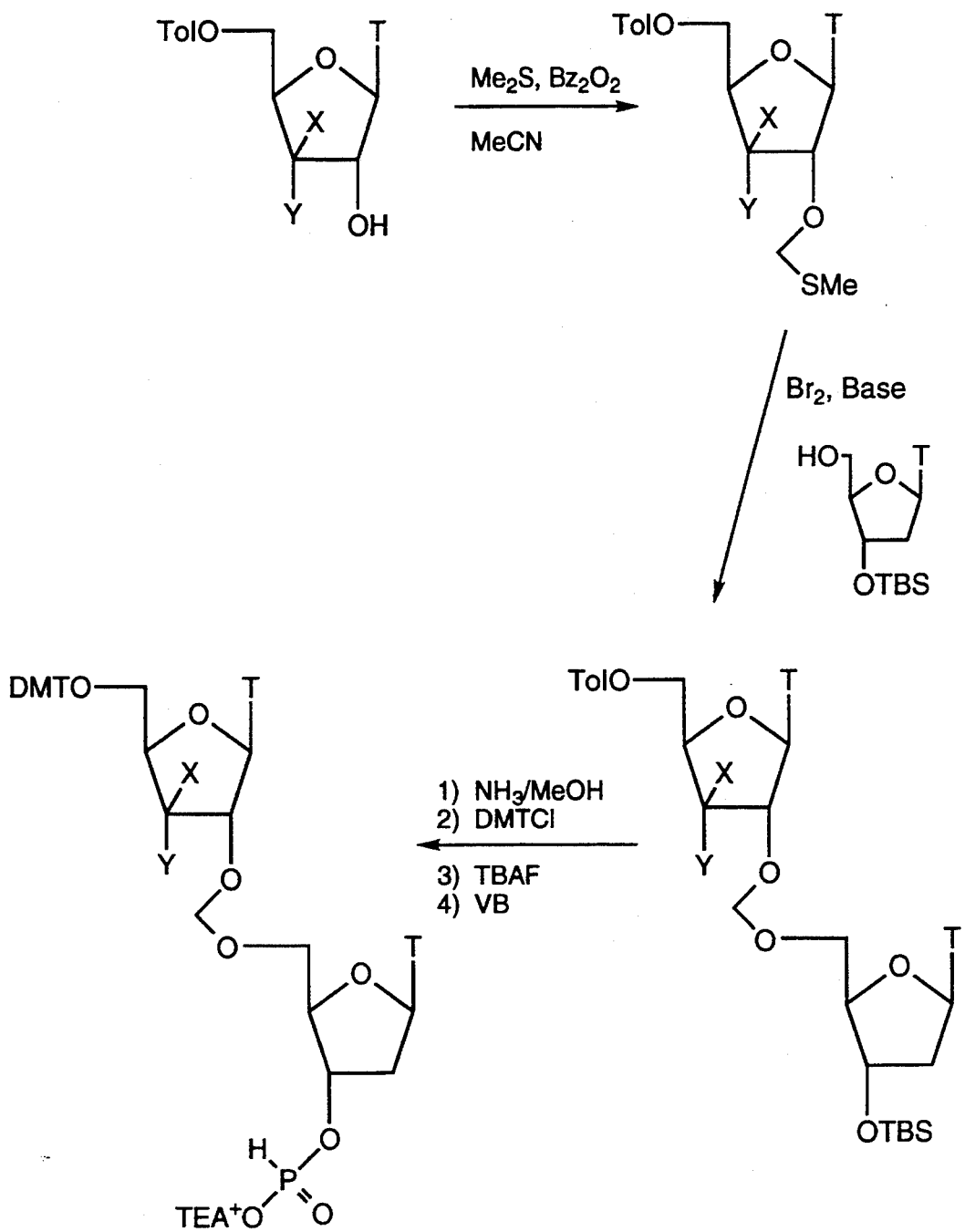

As can be seen from the variety of substitute linkages specifically listed in Table 1, noninvention substitute linkages can vary so as to contain one or more nitrogen, sulfur, and/or oxygen atoms in their structure. The positions of these atoms in the substitute linkage can vary from the '5'''end, to the "middle" to the '2'''end. A series of representative synthesis reaction schemes are set forth below which provide routes to various locations and combinations of nitrogen, oxygen, and sulfur atoms within the substitute linkages. For example, Scheme 1 shown in FIG. 1, shows the formation of a dimer containing a three atom long substitute linkage with a nitrogen at the 5' end of the 2' nucleomonomer. Scheme 2, depicted in FIG. 2, shows the formation of a three atom long substitute linkage with a nitrogen at the 2 ' end of the 5' nucleomonomer. Scheme 3, shown in FIG. 3, depicts the formation of a three atom long substitute linkage with a nitrogen in the middle. FIGS. 18 and 19 show the formation of several starting nucleomonomers for several linkages of the invention. FIG. 20 shows a scheme for synthesis of a 2',5'formacetal substitute linkage. FIGS. 21 and 22 show the synthesis of a xylosofluoro (Puech et al, *Tet Lett* (1989) 30:3171–3174) and ribofluoro (Mikhailopulo et al, *J Med Chem* (1991) 34:2195–2202) nucleomonomer and FIGS. 23 and 24 show the incorporation of these nucleomonomers into dimers linked via 5',2'thioformacetal and formacetal substitute linkages. These schemes can be modified as is known to those practicing in the area of oligonucleotide chemistry for synthesis of corresponding 3',5' linkages as described (US91/06855). Although protection of the bases is not always indicated in the synthesis schemes, such may be desireable and can be accomplished using reagents and techniques known in the art. See, e.g. Protective Groups in Organic Synthesis (Theodora W. Greene, John Wiley and Sons, 1981). Similarly, although the use of protective groups is shown in some cases, it is not always necessary to block the reactants in order to synthesize the exemplified invention oligomers. Turning to FIG. 1, the first two steps shown in Scheme 1 relate to the derivatization of thymine to a protected nucleoside. The third and subsequent steps in Scheme 1 are directed to the synthesis of the substitute linkage. The starting materials such as the material shown as compound 1 in Scheme 1 are 2'-deoxy-2'-(2-allyl) nucleosides. These allyl materials are analogous to the 3'-deoxy-3'-(2-propanyl) thymidyl derivatives described in Flandor, J. and Yam, S. Y., supra.

In step 1 of Scheme 1, the reactive 5'-hydroxyl in the nucleoside sugar is reacted with dimethoxytritylchloride (DMTCl) to protect it and yields compound 2. Other equivalent protecting groups may be used. In the next step, the 2'-allyl group of Compound 2 is oxidized with $OsO_4/NaIO_4$ to yield the aidehyde intermediate 4. The aidehyde 4 is then reacted with a 5-deoxy-5'-amino-3'-protected nucleoside, which can be selected from a range of known compounds and the resulting imine is reduced. This reductive alkylation reaction can be advantageously carried out using a suitable catalyst such as titanium isopropoxide and cyanoborohydride (see Mattson, R. J. et al, supra). This yields a protected dimer joined through a 2'—$CH_2$—$CH_2$—NH—5' substitute linkage. Compound 6 in Scheme 1 is representative. Thereafter, the 3'-hydroxyl protecting group is removed to yield compound 7. The amine group in the substitute linkage is protected, such as with an FMOC group to yield compound 8 and a phosphonate group is added to the 3'-hydroxyl with Van Boom's reagent (VB) (Marugg, J. E. et al, *Tet Letters* (1986) 27:2661–2664). This yields dimer 9 which has two nucleosides joined through a —$CH_2$—$CH_2$—N(FMOC)— substitute linkage, a free 3'-phosphonate group and a blocked 5'-position. This dimer can then be added into a growing oligomer using conventional chemistry. Alternatively, the resulting dimer or oligomer may be succinylated as a convenient linker for coupling to a solid support, such as controlled pore glass (CPG).

The coupled oligomer can be used as a starting material for standard oligonucleotide synthesis, as, for example, using H-phosphonate chemistry as described by Froehler, B., et al, *Nucleic Acids Res* (1986) 14:5399. This synthesis involves deprotection of the 5'-hydroxyl using dichloroacetic acid in methylene chloride and treatment with a 5'-DMT-protected base 3'-phosphonate in the presence of acetyl chloride/pyrimidine/acetonitrile, and repetition of this deprotection and linkage protocol for any desired number of times. Alternatively, the liberated 3'-OH can be linked via an ester linkage to a solid support analogous to standard oligonucleotide synthesis (Matteucci, M. et al, *J Am Chem Soc* (1981) 103:3185) for extension of oligonucleotide. The final product is removed from the solid support by standard procedures, such as treatment with iodine in a basic aqueous medium containing THF or other inert solvent, followed by treatment with ammonium hydroxide. Deprotection of the bases attached to the added nucleotides is also conducted by standard procedures. Similarly, the FMOC group protecting the nitrogen present in the substitute linkage can be removed conventionally and, if desired, replaced by other R groups as set forth herein. The substitute linkage can be included at any arbitrary position in an oligomer by substituting for a conventional monomer in the sequential synthesis, a protected dimer containing the substitute linkage which has been synthesized, for example, by the steps set forth in Scheme 1 shown in FIG. 1. Any DNA synthesis chemistry such as phosphoramidate or phosphonate chemistry can be used to link monomers or dimers in a manner analogous to that set forth above.

Turning to FIG. 2, a representative route (Scheme 2) is provided for generating a three atom long substitute linkage with a nitrogen at the 2' position is shown. In Step 1 the N3 group is reduced to an amine such as with hydrogen and a hydrogenitive catalyst to yield compound 12. Step 2 begins with an ester compound 13. This material is treated in Step 2 with base to hydrolyze the ester, and treated with acid to yield the free acid 14. The acid is then selectively reduced to the alcohol 15 using for example a borane reducing agent. The alcohol 15 is converted in Step 4 to the aidehyde 16 such as by using a carbodiimide and DMSO. Aidehyde 16 and amine 12 are then coupled in Step 5 and converted to phosphonate 18 in a manner analogous to that used in Scheme 1 by treatment with TBAF (Tetrabutyl ammonium fluoride), FMOC-NHS and Van Boom's reagent plus TEAB.

In Reaction Scheme 3 (shown in FIG. 3) the starting material is a 2'-alkyl substituted protected nucleoside such as 2. In Step 1 the alkyl double bond is isomerized by coupling the alkyl group to 19. Step 2 can be used to generate a 2'-aidehyde substituent present in compound 21. This aidehyde can then be coupled to the known amine 22 in Step 3 and converted to the phosphonate in Step 4 which are analogous to the steps described in Schemes 1 and 2.

In FIG. 4 a route for producing an oxygen- and nitrogen-containing substitute linkage is given. A free 2' hydroxyl is reacted in Step 1 with allyl iodide in the presence of sodium hydride to couple the allyl group to the free hydroxyl and yield compound 26. The allyl group in 26 is then oxidized to an aidehyde 28 which is reacted with amine-substituted nucleoside derivative 5 in Step 3 to give the two nucleosides coupled through a substitute linkage of the invention and yield "dimer 29" which is converted to the phosphonate form 30 using the methodology set out in Scheme 1.

Figure 5:
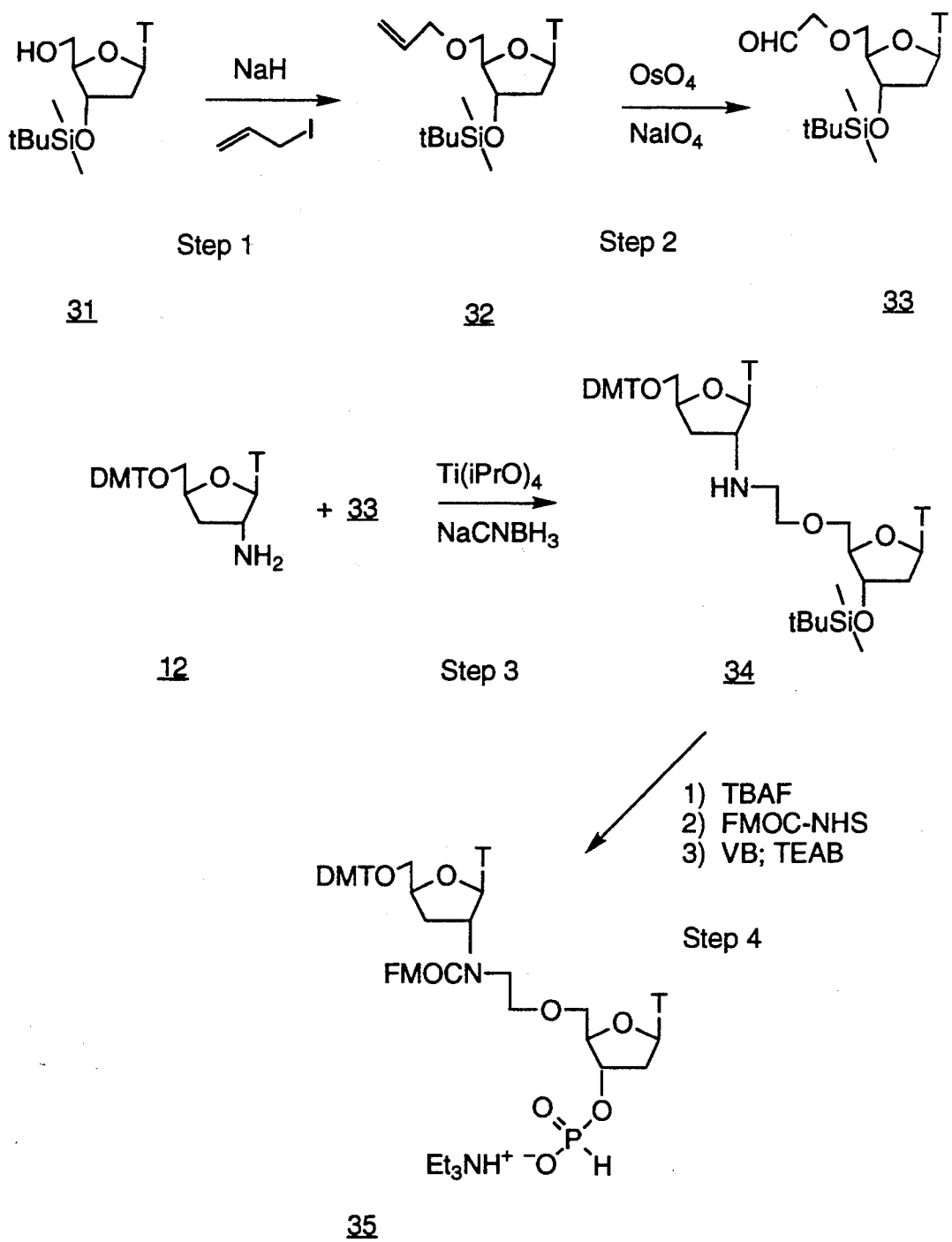

Scheme 5, shown in FIG. 5, is essentially the "reverse" of Scheme 4 in that the nitrogen is placed in the 2' position and the oxygen in the 5' position. Essentially the same reactions are conducted using different blocking and substitution patterns to achieve the reverse orientation.

Figure 6:
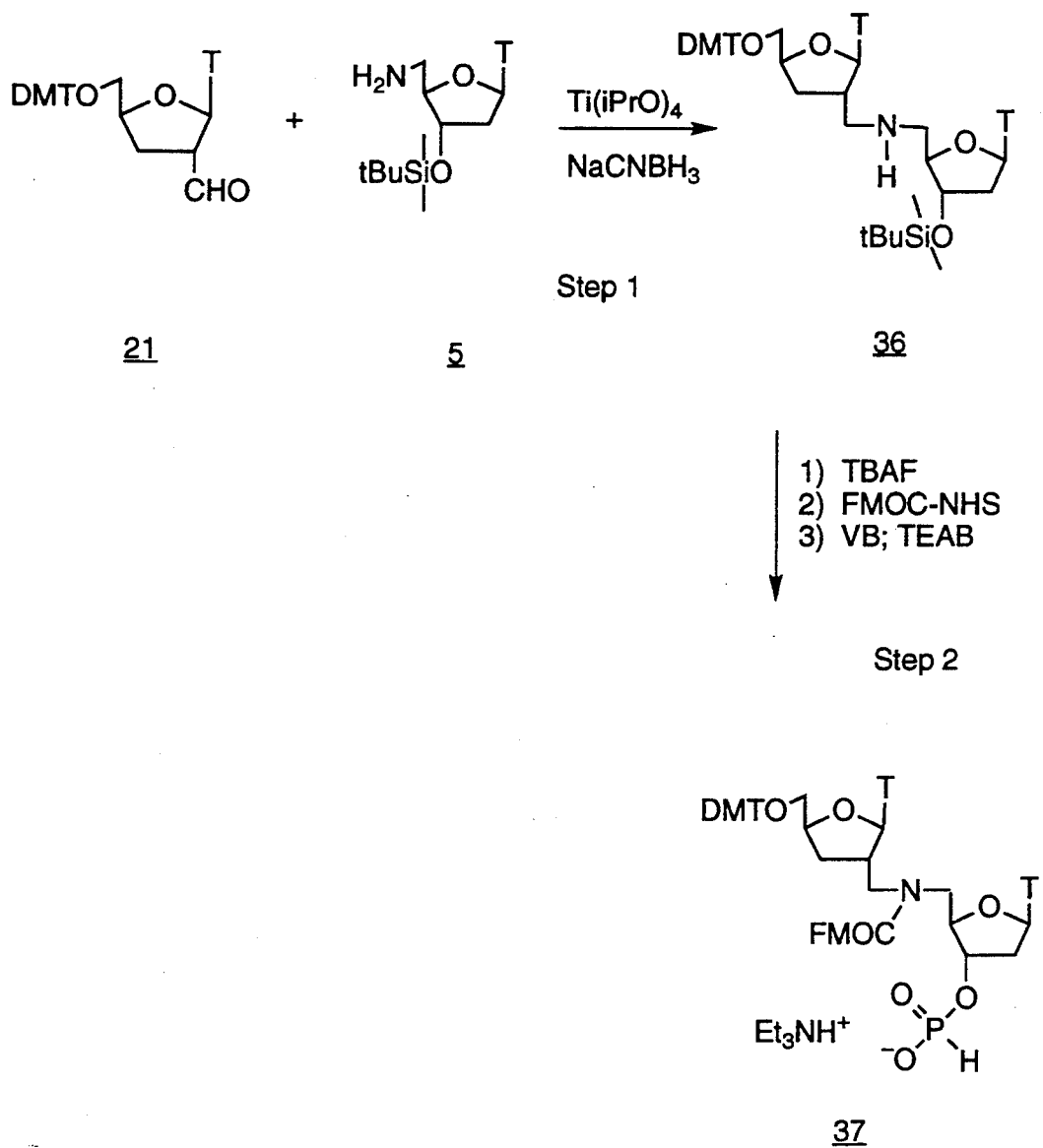

Scheme 6, shown in FIG. 6, provides a two atom long substitute linkage. It employs as representative nucleoside analog starting materials, aidehyde 21 (produced in Scheme 3) and amine 5 (noted as available in Scheme 1). These materials are coupled and converted to a phosphonate in Steps 1 and 2 which are analogous to Steps 5 and 6 of Scheme 2.

Figure 7:
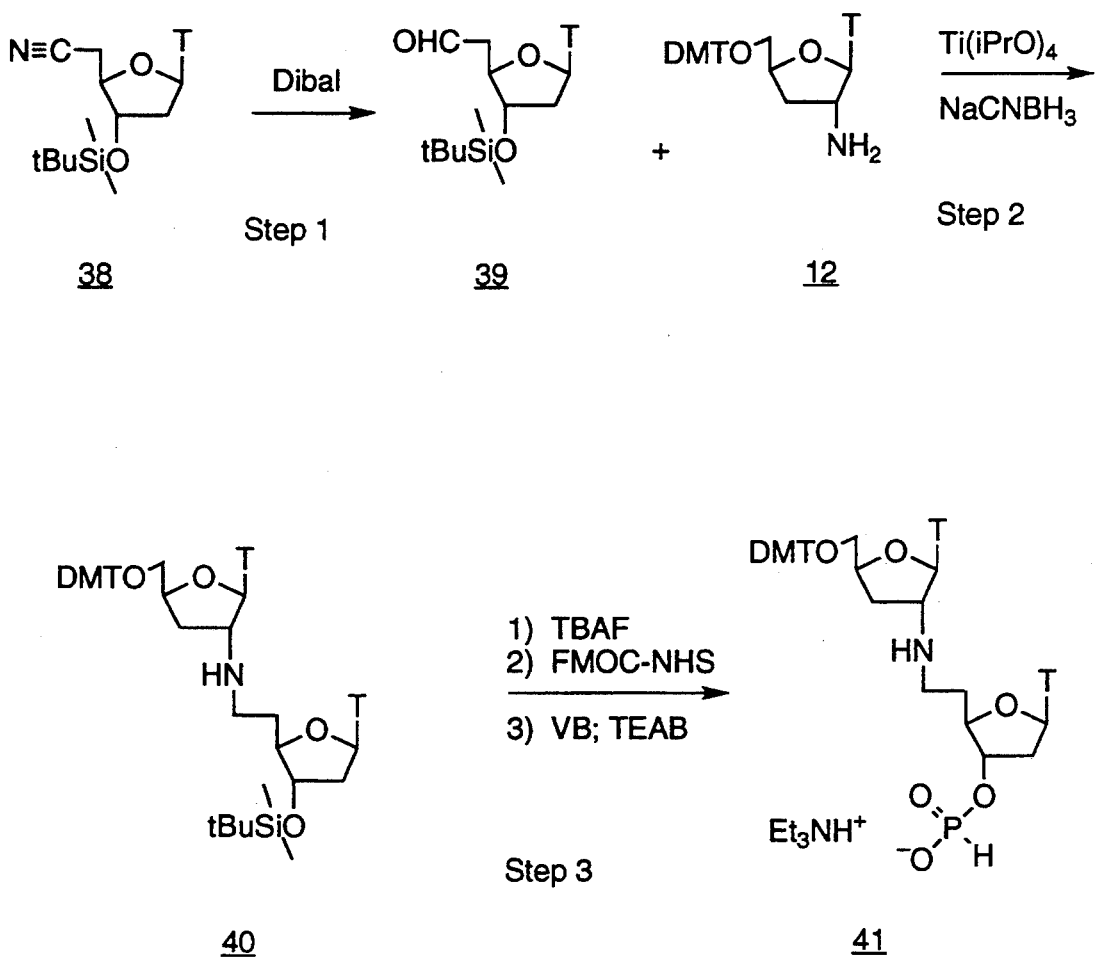

Scheme 7 shown in FIG. 7 also involves a 2 atom substitute linkage, this time with a nitrogen at the "5'"' end. This reaction sequence starts with the known 5' nitrile 38 (Meyer et al, *Agnew Chem* (1976) 88:512–513; Etzold et al, *Chem Commun* (1968) 7:422) which is converted to an aidehyde 39 in Step 1. This aidehyde then is coupled to amine 12 (previously prepared) in Step 2 and converted to a phosphonate in Step 3, again analogous to Steps 5 and 6 of Scheme 2.

Figure 8:
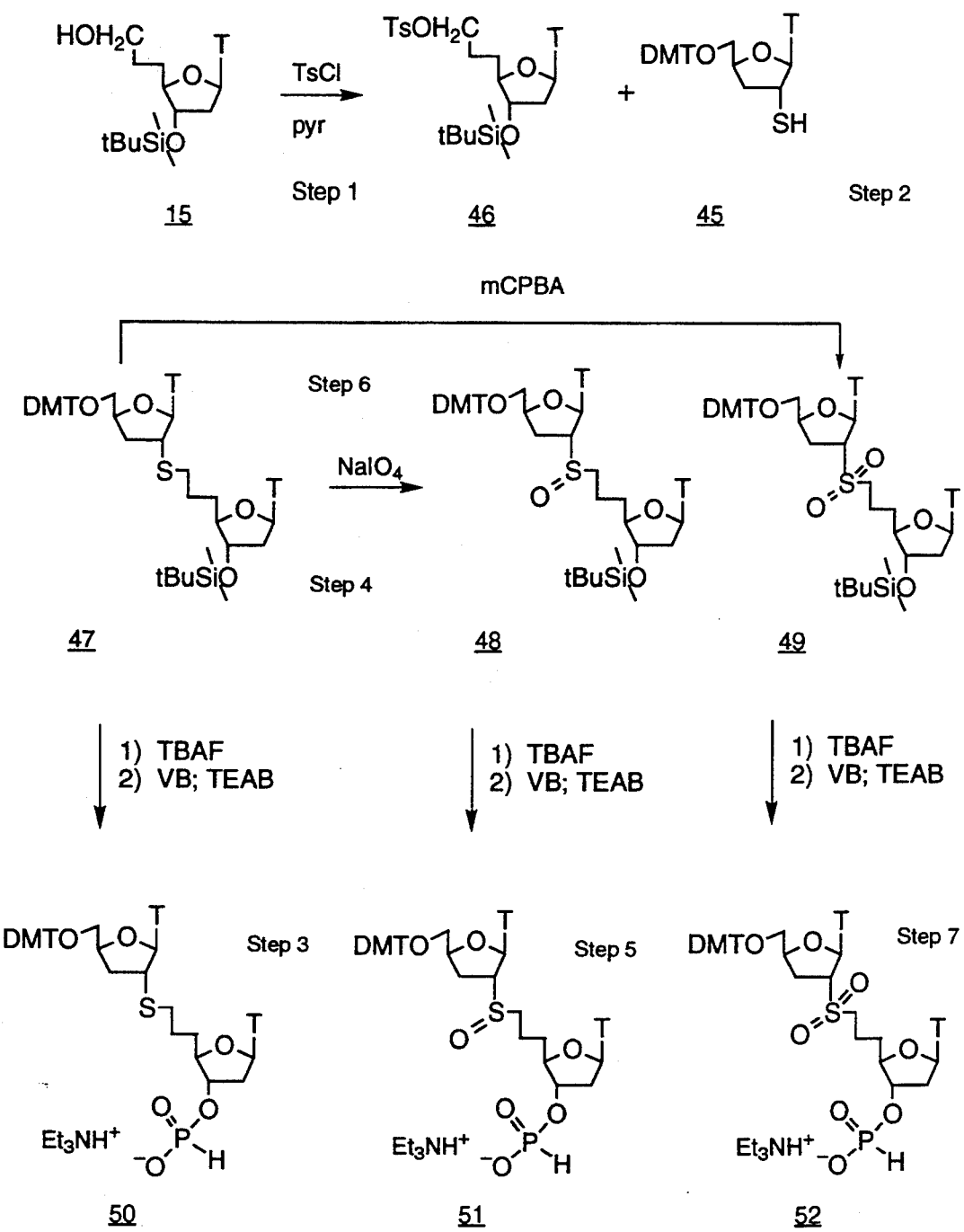

Scheme 8, shown in FIG. 8, provides a route to three atom long substitute linkages having sulfur in various oxidation states at the 2' end. The scheme begins with the thiol 45 which was synthesized as shown in FIG. 19. In Step 1 the alcohol group on compound 15 (produced in Scheme 2) is reacted with tosyl chloride. Tosylate 46 is then coupled with thiol 45 in Step 2 to yield sulfur-containing "dimer" 47. Dimer 47, having sulfur as -S- can be converted directly to a phosphonate as shown in Step 3. Alternatively the sulfur can be partially oxidized with NaIO$_4$ (Step 4) to —S(O)— or with an MCPBA (Step 6) to —S(O)(O)— and then converted to the respective phosphonates as shown in Steps 5 and 7.

In Scheme 9 several two atom long sulfur-containing substitute linkages are constructed. Aidehyde 39, prepared in Scheme 7 is reduced to alcohol 53 with a borohydride reducing agent. The alcohol is converted to a tosylate 54 which is then coupled to the thiol 45 from Scheme 8 in Step 3 to yield "dimer" 55. Dimer 55 is then converted to the phosphonate with or without oxidation in Steps 4, 5–6 and 7–8 respectively. Alternatively, alcohol 53 is converted to the corresponding bromide by reaction with triphenylphosphine and CBr$_4$ in DMF, followed by coupling with thiol 45 in step 3 using sodium trimethylsilanoate (1.0M) in THF. Conversion of 38 (Figure &) to 39 is followed by reduction of 39 to the alcohol 53 without purification of 39. Reactions analogous to conversion of 38 to 53 are preferably accomplished using t-butyldiphenylsilyl as the 3' protecting group instead of with the t-butyldimethylsilyl group shown.

Figure 10:
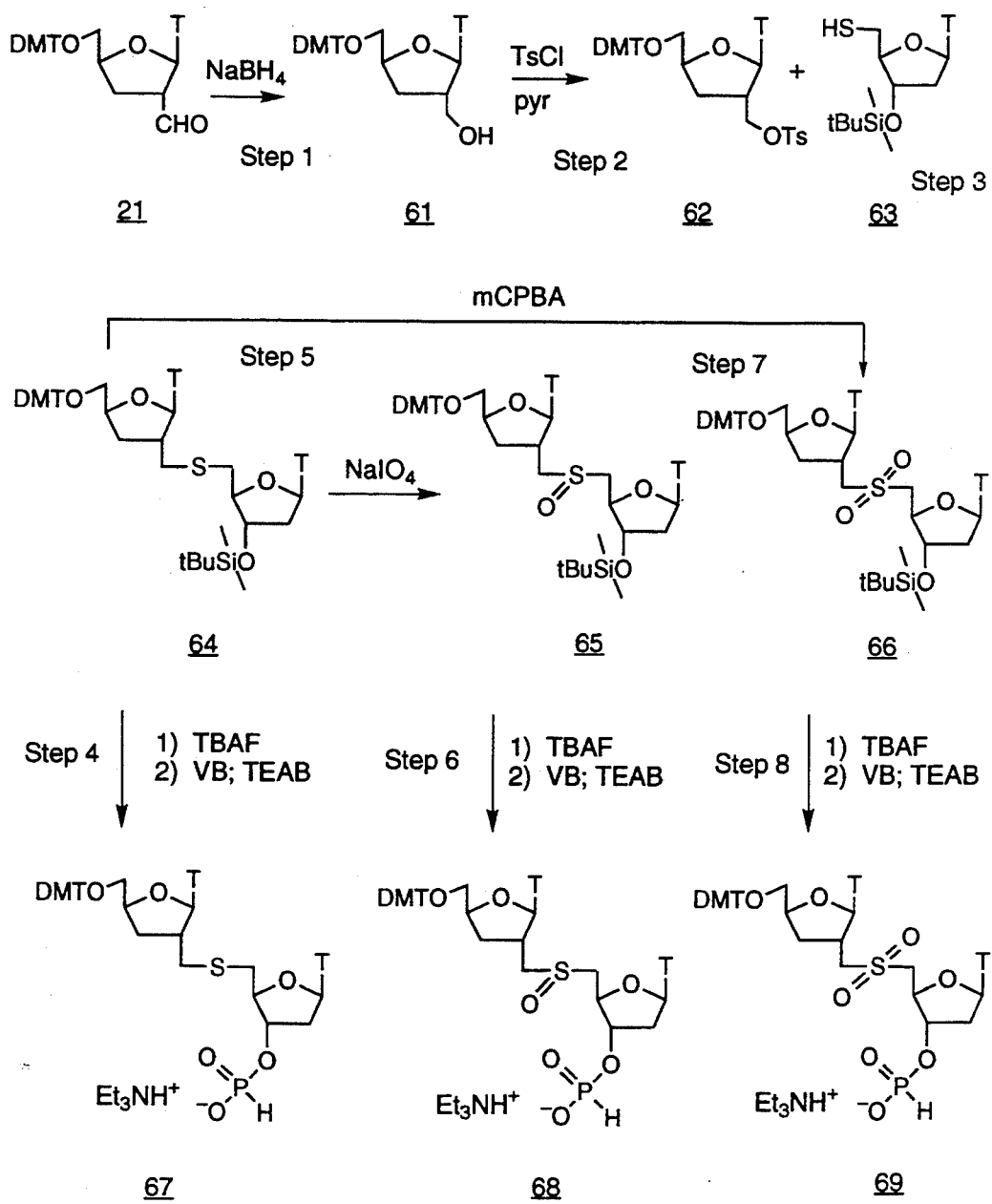
Figure 11:
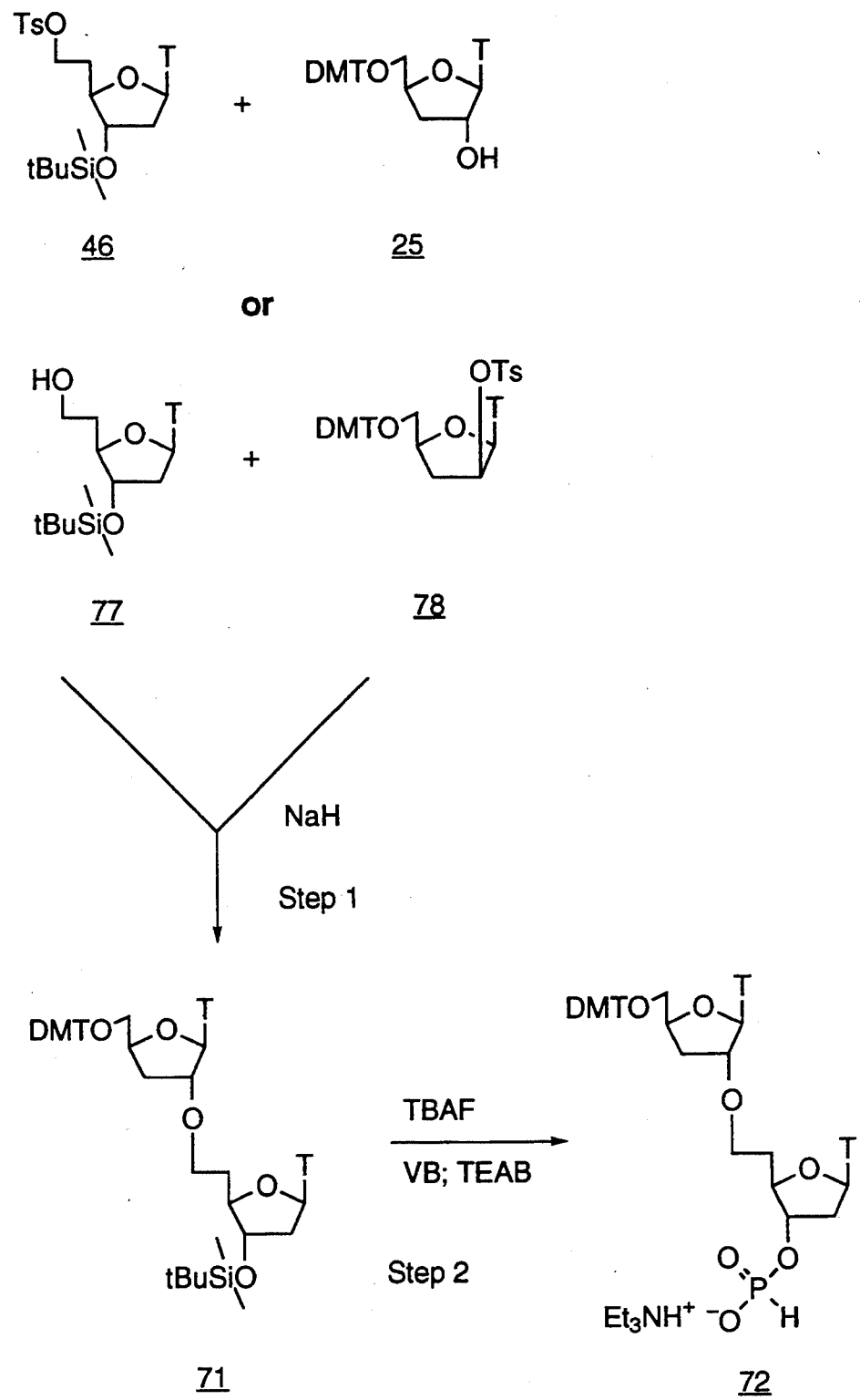
Figure 12:
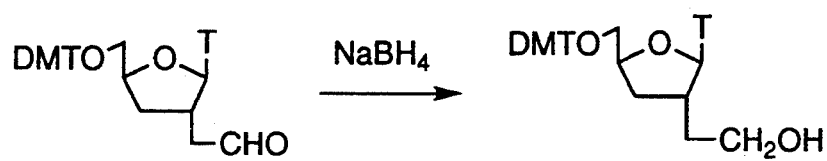
Figure 12:
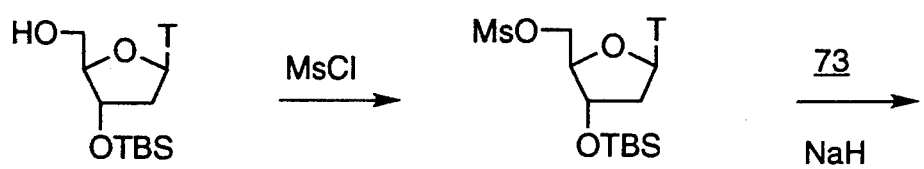
Figure 12:
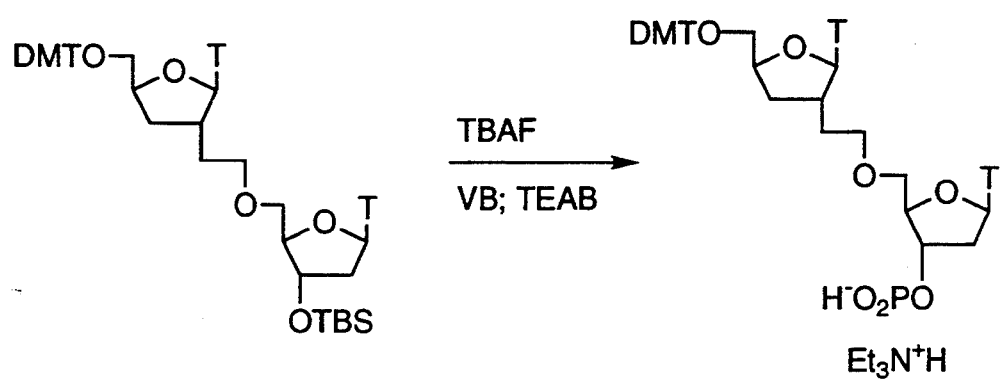

FIG. 10 shows Scheme 10 which is directly analogous to Schemes 8 and 9 just described with variation in the position of the aidehyde group and thiol group. Again, this scheme gives rise to 3 families of materials 67, 68 and 69 which differ from one another in terms of sulfur oxidation state.

Schemes 11 and 12 are representative routes to nucleomonomers linked with oxygen present at the 2' and 5' ends of the linking group. In Scheme 11, two routes are shown. In one a "5'"' tosylate 46 is reacted with a "2'"' alcohol 25 to yield dimer 71 which is converted to a phosphonate to yield 72. Alternatively a 2' tosylate 78 can be reacted with a 5' alcohol 77 to yield 71.

In Scheme 12, 2' aidehyde 4 is reduced to 2' alcohol 73 which is coupled to 5' mesylate 74 to give oxygen-containing linked material 75 which is converted to phosphonate 76.

Figure 13:
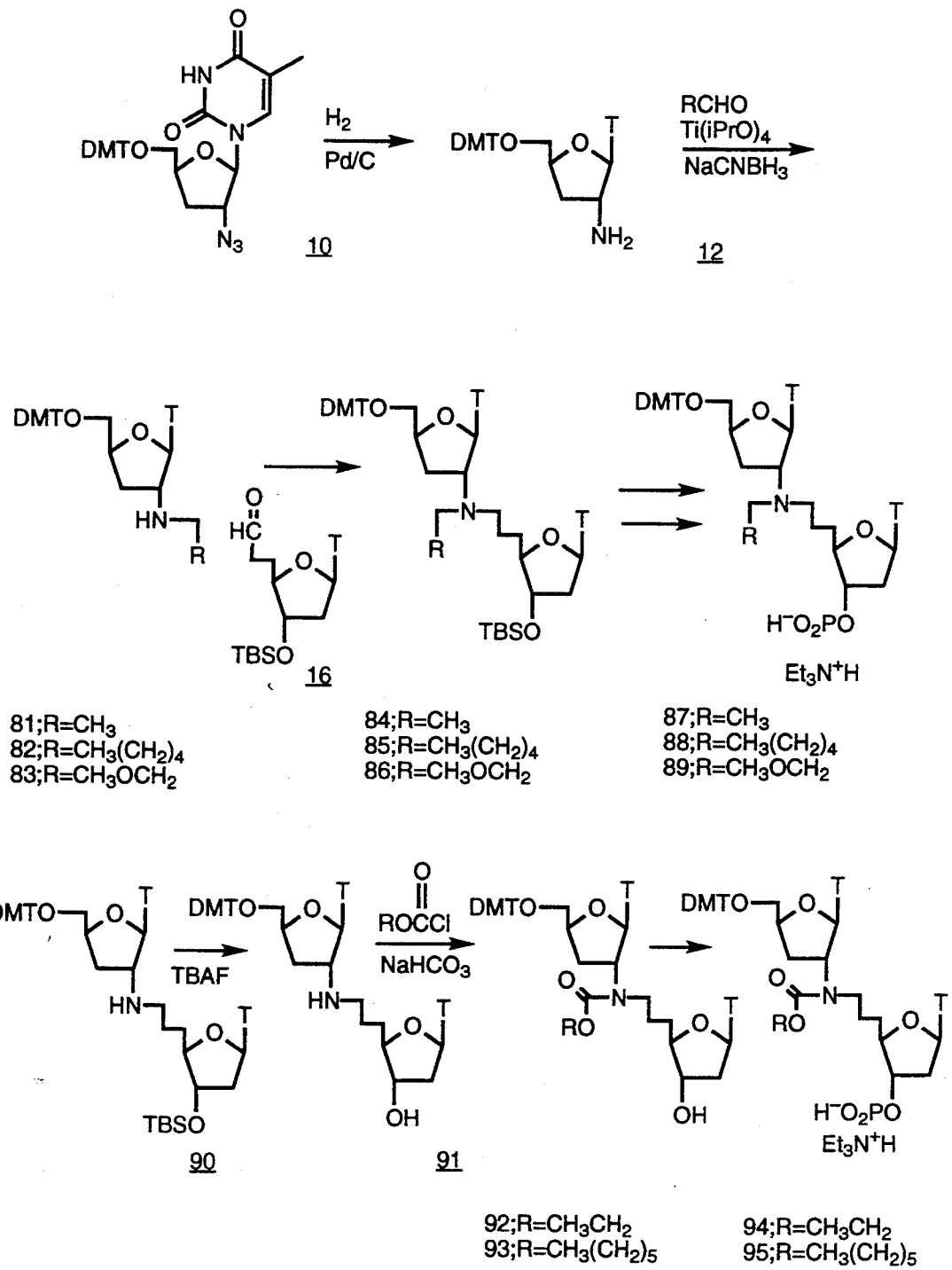

FIG. 13, Scheme 13, shows the synthesis of alkyl derivatives of a 2' amine of a three atom long substitute linkage. Azide 10 is hydrogenated to deliver the amine 12. Amines 81, 82 and 83 are treated with acetaldehyde toluene, and titanium isopropoxide and the products coupled with aidehyde 16, as described for amine 12, to yield dimers 84–86 which are in turn converted to the corresponding phosphonates 87–89. Acylated derivatives of the 2' amine begin with dimer 90, which is prepared as explained for compound 17. The products are ultimately converted to phosphonates as described further below.

The synthesis of an aminal-containing substitute linkage (FIG. 14, Scheme 14) begins with amine 12, which is acylated to yield carbamate 99, which is alkylated to produce thioaminal 100 and is ultimately converted to the corresponding phosphonate.

Figure 15:
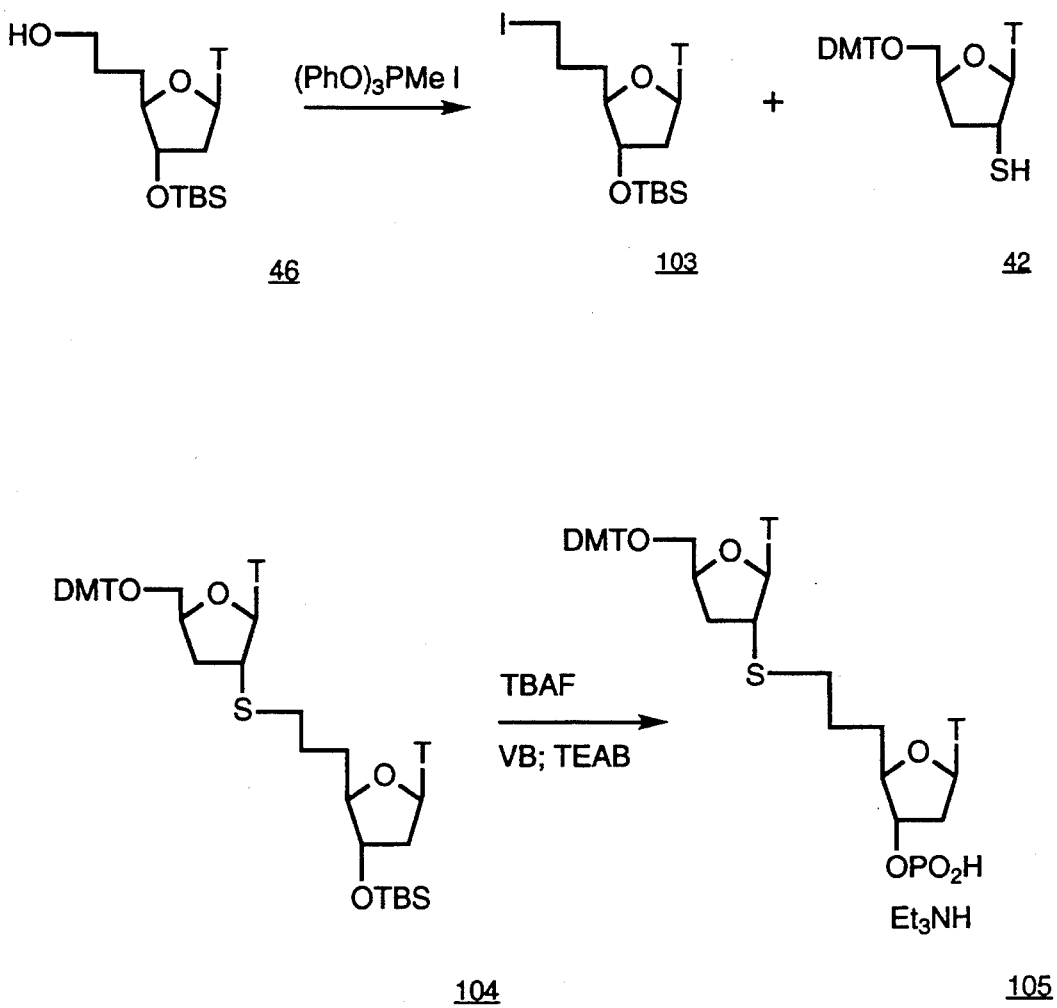

FIG. 15, Scheme 15, shows the preparation of a three atom long substitute linkage with a 2' sulfur. Alcohol 46 (in DMF and pyridine) is reacted within methyltriphenoxyphosphonium iodide. The product is saturated with sodium thiosulfate to yield iodide 103. Thiol 42 and acetonitrile are combined with acetamide and DMF, and iodide added, to ultimately yield dimer 104 which is converted to a phosphonate 105 as described for compound 18. The following examples are intended to illustrate but not to limit the invention.

EXPERIMENTAL

Example 1.

The compounds of this example are shown in Scheme 1, shown in FIG. 1. To a flask containing compound 1 (which may be produced using Scheme 18 as shown in FIG. 18) is added pyridine and the solution is evaporated to dryness. Pyridine is added again followed by DMTCl; the solution is stirred for 18 hours and poured in 10% aq sodium bicarbonate solution. The crude product is extracted with CHCl$_3$, dried (Na$_2$SO$_4$), stripped to dryness, and chromatographed on silica gel (5% MeOH/MC) (methanol/methylene chloride) to yield the product 2. To a solution of 2 in dioxane and 1% aqueous sodium bicarbonate is added osmium tetroxide (2.5 wt % solution in t-butyl alcohol), and the solution stirred for 5 minutes. Sodium periodate is added in four portions, and the mixture stirred. The solution is poured into 10% aqueous saturated bicarbonate and the crude product is extracted with chloroform; dried (Na$_2$SO$_4$); and concentrated. The resulting oil is taken up in methylene chloride; filtered through celite and concentrated. To this aidehyde is added, 5'-amino, 3-(O-t-butyldimethylsilyl)thymidine, toluene, and titanium tetraisopropoxide. After stirring for 1 hour, ethanol (20 ml abs) and sodium cyanoborohydride are added and the reaction stirred. The solution is poured into 10% aq sodium bicarbonate solution and the crude product extracted with chloroform; dried (Na$_2$SO$_4$); stripped to dryness, and chromatographed on silica (1% Et$_3$N/5 to 10% methanol/MC) to yield the product 6. Compound 6 is dissolved in THF and tetrabutylammonium fluoride is added. The reaction solution is stirred, concentrated and applied to a silica gel column and chromatographed (1% Et$_3$N/5 to 10 to 15% MeOH/MC) to yield the product 7. To a solution of compound 7 in acetonitrile and methanol is added N-(9-Fluorenylmethoxycarbonyloxy) succinimide, and the solution stirred. The crude product is concentrated to dryness; toluene is then added and the solution is again evaporated to dryness to deliver the product 8. Compound 8 is dried by azeotropic distillation with pyridine. To a solution of 8 in pyridine and methylene chloride (MC) at 0° C. is added a solution of 2-chloro-4H-1,3,2-benzodioxaphosphorin-4-one (PA; 1M in MC). The solution is stirred and quenched with pH 7.5 triethyl ammonium bicarbonate (TEAB). The crude product is extracted with 4:1MC/n-butanol, dried (Na$_2$SO$_4$), and diluted with acetonitrile. The solution is concentrated and chromatographed on silica gel (1% pyr/O to 20% H$_2$O/acetonitrile). The product-containing fractions are concentrated, diluted with toluene and concentrated again. The product is then dissolved in 3:1MC/n-butanol and back extracted with pH 7.5 triethylammonium bicarbonate. The organic layer is dried (Na$_2$SO$_4$), diluted with acetonitrile, and concentrated to afford the final product 9. The FMOC group can be substituted using conventional techniques.

Example 2.

The compounds used and generated in this example are shown in Scheme 2, FIG. 2. A mixture of compound 10 obtained as shown in FIG. 19, Scheme 19, M 10% palladium on carbon, ethyl acetate, and methanol is hydrogenated at atmospheric pressure. The reaction mixture is filtered through celite, and the solvent is evaporated. The crude product is chromatographed on silica gel (0.5% TEA/5% MeOH/MC) to yield the product 12.

Compound 13 is dissolved in dioxane and water and treated with lithium hydroxide. The solution is poured into ice cold 0.1M H$_3$PO$_4$ and chloroform. The crude product is extracted with chloroform, dried over Na$_2$SO$_4$, concentrated, and chromatographed on silica gel (5% methanol/MC) to yield the carboxylic acid 14.

To a solution of carboxylic acid 14 in tetrahydrofuran at 0° C. is added BH$_3$-THF (1.0M in THF) in three portions. The mixture is slowly poured into ice cold aqueous sodium bicarbonate. The product is extracted with chloroform, dried over sodium sulfate, and concentrated to provide alcohol 15. A solution of 15 in DMSO is treated with N,N'-dicyclohexyl carbodiimide (DCC) and dichloroacetic acid, and the mixture stirred. The reaction mixture is poured into 5% aqueous bicarbonate, and the crude product extracted with chloroform, dried over sodium sulfate, concentrated, and chromatographed on silica gel (5% MeOH/MC) to afford the aidehyde 16.

The aidehyde 16 and amine 12 may be coupled and then converted into the phosphonate 18 in analogous fashion as described for compound 6 (Example 1). Following synthesis, the FMOC group can be replaced using conventional methods.

Example 3.

The compounds used and generated in this example are shown in Scheme 3, FIG. 3.

Preparation of 20: To a dry (azeotroped from pyridine at reduced pressure) sample of compound 2 is added dry CHCl$_3$ (ethanol-free) and stirred at room temperature until a solution results. To this solution is added 4-methyl-1,2,4-triazoline-3,5-dione. The resulting red solution should be protected from light and allowed to stir at room temperature overnight. More 4-methyl-1,2,4-triazoline-3,5-dione is added, and the reaction mixture is protected from the light and allowed to stir at room temperature overnight. The reaction mixture is diluted with CHCl$_3$ and the organic phase washed with saturated aqueous NaHCO$_3$, separated, and dried over Na$_2$SO$_4$. Removal of solvents affords a dark yellow oil, which is purified by column chromatography with Baker, Inc. silica gel, using a step gradient of 4%-20% isopropyl alcohol in CH$_2$Cl$_2$ as eluent. This will afford a clear oil, whose $^2$H NMR spectral properties are consistent with the structure of 20. Compound 20 is oxidized to 21. Compound 21 is coupled with amine 22 and may be subsequently converted into the phosphonate 24 in a similar manner to that described for compound 2. The FMOC group may be substituted using conventional methods.

Example 4.

The compounds used and generated in this example are shown in Scheme 4, FIG. 4.

To a solution of 25 in THF is added NaH (60% dispersion in oil), and the solution stirred. Allyl iodide is added, and the solution stirred for an additional period. The reaction mixture is poured in 5% aqueous bicarbonate, and the crude product is extracted with MC, washed with saturated brine, dried over sodium sulfate, and concentrated to deliver the product 26 as a crisp yellow foam.

Compound 26 is converted into aidehyde 28 in the manner previously described for compound 2. Aidehyde 28 is coupled with compound 5 and subsequently converted to the phosphonate 30 as described above. The FMOC group may be substituted using conventional methods.

Example 5.

Preparation of 5'- TCTCme(CH$_2$—CH$_2$NH)T-Cme(CH$_2$—CH$_2$—NH)TCme(CH$_2$—CH$_2$—NH)T-Cme(CH$_2$—CH$_2$—NH)TTTT—2'(SEQID No: 1).

The oligomer of this example is synthesized using the conventional techniques described by Froehler et al, *Nucleic Acids Res* (1986) 14:5399, but with the incorporation of the Cme(CH$_2$—CH$_2$-NFMOC)T dimer synthon. This dimer is constructed using the technique described in Example 1. The oligomers resulting from the synthesis may be deblocked with concentrated ammonia and gel purified using conventional techniques.

Example 6.

Preparation of 5'-TCTCme(O—CH$_2$—CH$_2$—NH)T-Cme(O—CH$_2$CH$_2$—NH)TCme(O—CH$_2$—CH$_2$—NH)TCme(O—CH$_2$—CH$_2$—NH)TTTF—2'(SEQID No:2).

The oligomer of this example is synthesized as in Example 6, using the conventional techniques described by Froehler et al, *Nucleic Acids Res* (1986) 14:5399, but with the incorporation of the Cme(O—CH$_2$—CH$_2$—NFMOC)T dimer synthon. This dimer is constructed using the technique described in Example 4. The oligomer resulting from the synthesis is deblocked with concentrated ammonia and gel purified using conventional techniques.

Example 7.

Preparation of 5'-TCTCTC(CH$_2$—CH$_2$—O)TC(CH$_2$—CH$_2$—O) TCTTTT—2'(SEQ ID No:3).

The oligomer prepared in this example consisted of conventional nucleotides as well as modified internucleoside linkages wherein the C preceding each of the modified linkers is a hydroxyethyl morpholino cytidine. This oligomer is synthesized as in Example 6, using the conventional techniques described by Froehler, B. C. et al, *Nucleic Acids Res* (1986) 14:5399, but with the incorporation of the morpholine C(CH$_2$—CH$_2$—O)T dimer synthon. This dimer is constructed using the technique described in Example 5. The oligomers resulting from the synthesis may be deblocked with concentrated ammonia and gel purified using conventional techniques.

Example 8.

Preparation of T (NR—Ctt2—CH$_2$) T. The preparation of alkyl derivatives of the 2' amine, as shown in Scheme 13, FIG. 13 begins with azide 10. Compound 10 in methanol with 10% palladium on carbon is hydrogenated. The catalyst may be removed by filtration and the solvent removed by rotary evaporation to deliver the amine 12. To a solution of amine 12, acetaldehyde and toluene is added titanium isopropoxide and the solution stirred. At this point absolute ethanol (25 mmol) and sodium cyanoborohydride may be added. The mixture is subsequently stirred and stripped to dryness. The crude product is chromatographed on silica gel (1% Et$_3$N/3 to 5 to 8% 2-propanol/MC) to deliver the product as a white foam. In a similar manner, amines 82 and 83 may be prepared. Compounds 81-83 are then coupled with aldehyde 16 as described for amine 12 to deliver dimers 84-86, which may then converted to the corresponding phosphonates 87-89 as described for compound 18. The preparation of acylated derivatives of the 2' amine may begin with the dimer 90, which is prepared as described for compound 17. Dimer 90 is deprotected with tetrabutylammonium fluoride as described for compound 7 to yield dimer 91. To a solution of amine 91, ethyl acetate and 5% aqueous sodium bicarbonate is added ethyl chloroformate. The organic layer is separated, dried over sodium sulfate, and concentrated. The crude product is chromatographed on silica gel (3 to 5 to 10 to 15% 2-propanol/MC) to yield the product 92. Likewise, carbamate 93 is prepared. Compounds 92 and 93 are subsequently converted to the phosphonates 94 and 95 as described above.

Example 9.

Figure 14:
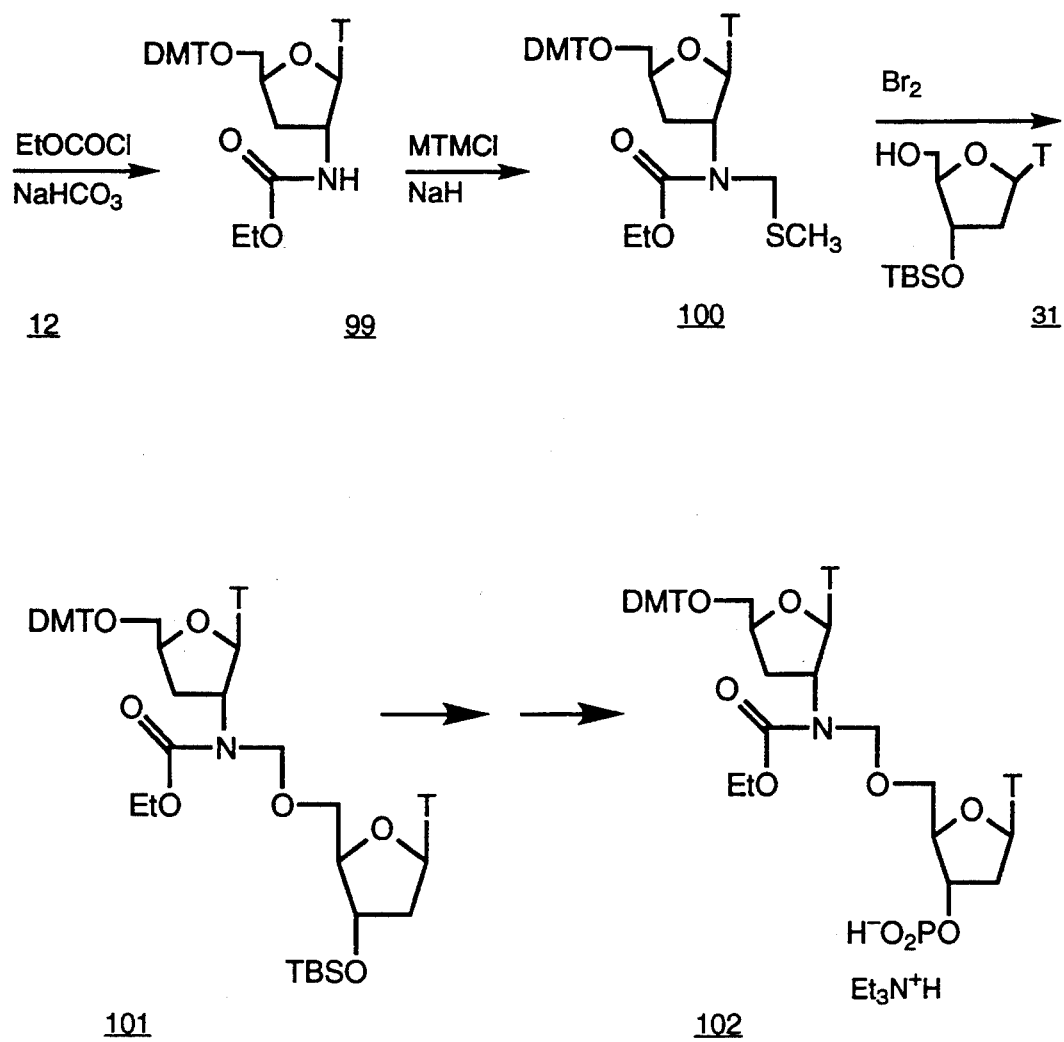

As is shown in Scheme 14, shown in FIG. 14, the aminal derivative 101 is prepared from amine 12, which is acylated with ethyl chloroformate to give carbamate 99. The carbamate 99 is alkylated with chloromethyl methylsulfide in the presence of sodium hydride to afford thioaminal 100. Compound 100 is activated with bromine in the presence of alcohol 31 to deliver dimer 101, which is then converted to the corresponding phosphonate 102 using the method described above.

Example 10.

The compounds of this example are shown in Scheme 15, FIG. 15. To a solution of alcohol 46 in DMF and pyridine is added methylthiophenoxyphosphonium iodide, and the reaction stirred. The reaction is quenched with methanol and the solvents removed on the rotary evaporator. The crude product is dissolved in methylene chloride is extracted with aqueous saturated sodium thiosulfate and aqueous saturated sodium bicarbonate; dried; concentrated; and chromatographed on silica gel to deliver the iodide 103. To a solution of thiol 42 (which may be produced using Scheme 18 in FIG. 18) and acetonitrile is added bis(trimethylsilyl) acetamide. The solvent may be evaporated; DMF and iodide 103 are added. The reaction is stirred and then quenched with aqueous saturated sodium bicarbonate. The crude product is extracted with methylene chloride; dried; concentrated; and chromatographed on silica gel to deliver dimer 104. Dimer 104 is converted to the phosphonate 105 as described above.

Example 11.

Figure 16:
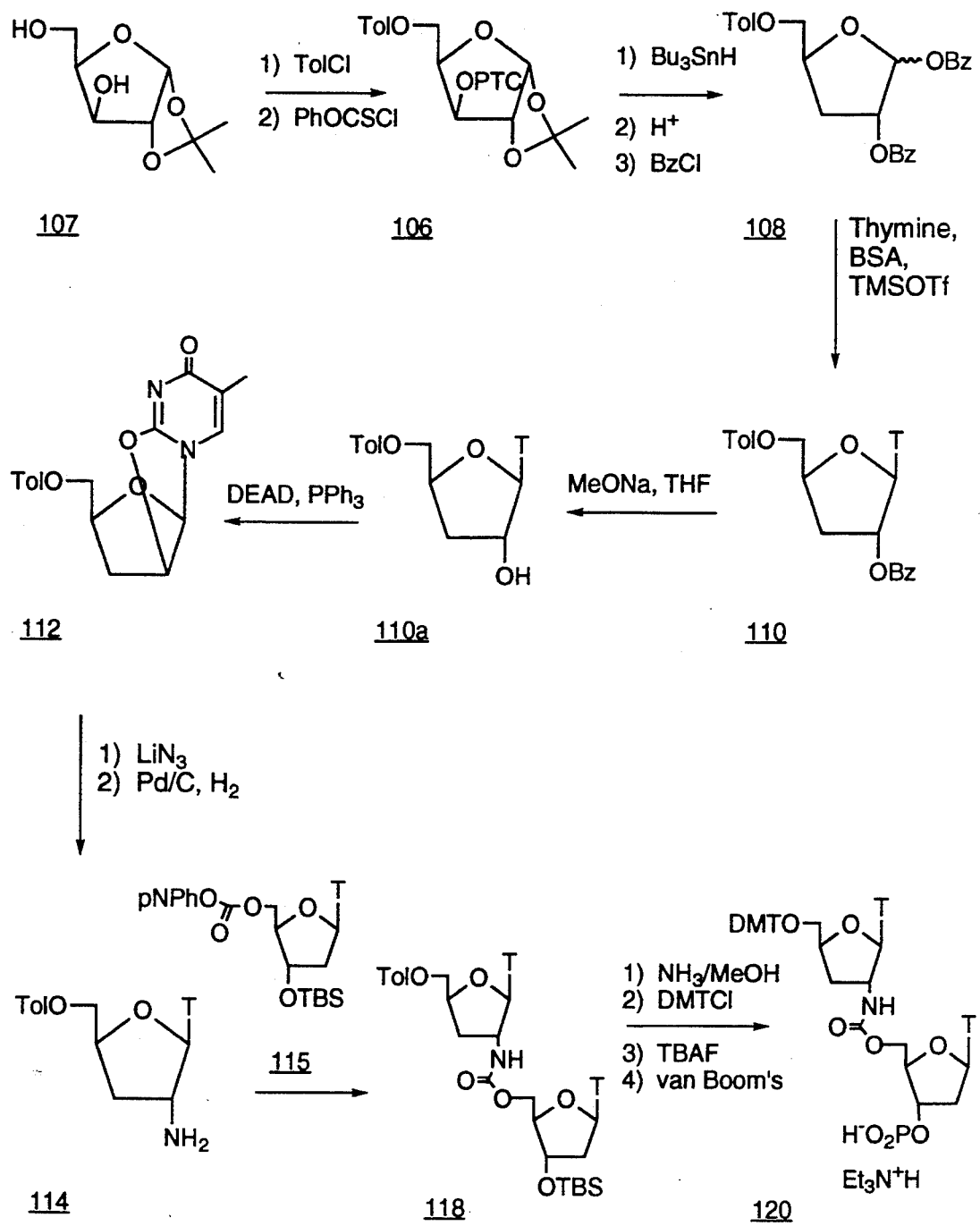

Preparation of Compound 120. This Example shows the preparation of Compound 120. The synthesis is found in FIG. 16. Compound 107 (Aldrich) was treated with toluyl-chloride in pyridine/CH$_2$Cl$_2$ followed by an aqueous work-up. The resulting syrup was crystallized from ether/hexane to yield white needles (89%). This 5-toluyl compound was then treated with phenoxythionocarbonyl chloride and DMAP in acetonitrile followed by an aqueous work-up to yield a tan solid (106).

Compound 106 was treated with tributyltin hydride and AIBN in toluene at 80° C. for 4 hours. The solvent was removed in vacuo and the resulting oil subjected to column chromatography and eluted with 15% EtOAc/hexane to yield a clear, colorless syrup. This syrup was dissolved in dioxane/1 N HCl and heated at 65° C. for 1 hour. The solvent was cooled and neutralized by addition of saturated aqueous NaHCO$_3$ (pH=6). The solution was then reduced in vacuo until a two phase solution was observed. The solution was diluted with EtOAc and washed with saturated aqueous NaHCO$_3$ and brine. The organic phase was decanted, dried, and reduced to a yellow syrup. This syrup was dissolved in pyridine/CH$_2$Cl$_2$ and treated with benzoyl chloride for 12 hours. The solvent was removed and the residue subjected to an aqueous work-up. The resulting syrup was subjected to column chromatography and eluted with 15% EtOAc/hexane. Thymine was silylated in acetonitrile with BSA at 70° C. and treated with a solution of compound 108 followed by TMSOTf. The solution was stirred for 1 hour, cooled, and subjected to an aqueous work-up. The resulting white foam was subjected to column chromatography and eluted with 55% EtOAc/hexane.

Compound 110 was dissolved in anhydrous THF and treated with MeONa followed by neutralization and an aqueous work-up. The resulting white foam was crystallized from Et$_2$O to yield a white powder.

Compound 110a was dissolved in THF and treated with PPh$_3$ and DEAD at 0° C. for 30 minutes. The solvent was removed and the resultant oil subjected to column chromatography and eluted with 7% MeOH/CH$_2$Cl$_2$.

Compound 112 was dissolved in DMF and treated with LiN$_3$ and NH$_4$Cl at 100° C. for 8 hours. The solution was cooled and the solvent removed and the residue subjected to an aqueous work-up. The resultant foam was dissolved in EtOH and treated with 10% Pd/C. The suspension was then hydrogenated at 60 psi H$_2$ for 12 hours. The suspension was filtered and the filtrate reduced to a white foam.

Compound 114 was dissolved in DMF and compound 115 and TEA were added. This solution was stirred at room temperature for 90 minutes. The solvent was removed and the residue subjected to column chromatography and eluted with 4% MeOH/CH$_2$Cl$_2$.

Compound 118 was dissolved in MeOH/NH$_3$ and the sealed flask was heated at 70° C. for 12 hours. The solvent was removed and the residual foam was crystallized from Et$_2$O to yield a white powder. This powder was dissolved in pyridine and treated with DMTCL for 3 hours. The solvent was removed and the residue subjected to an aqueous work-up. The residual oil was subjected to column chromatography and eluted with 3% MeOH/CH$_2$Cl$_2$. The resultant white foam was dissolved in THF and treated with Bu4NF for 1 hour and the solvent was removed in vacuo. The resultant white foam was subjected to column chromatography and eluted with 8% MeOH/CH$_2$Cl$_2$ to yield a white powder. This powder was dissolved in pyridine/CH$_2$Cl$_2$ and cooled to 0° C. and treated with van Boom's reagent for 30 minutes. The solution was neutralized with TEAB (1N, pH=7) and extracted with CH$_2$Cl$_2$ and reduced to a white foam. This foam was subjected to column chromatography and eluted with 12% MeOH/CH$_2$Cl$_2$/0.5%TEA to recover compound 120.

Example 12.

Figure 17:
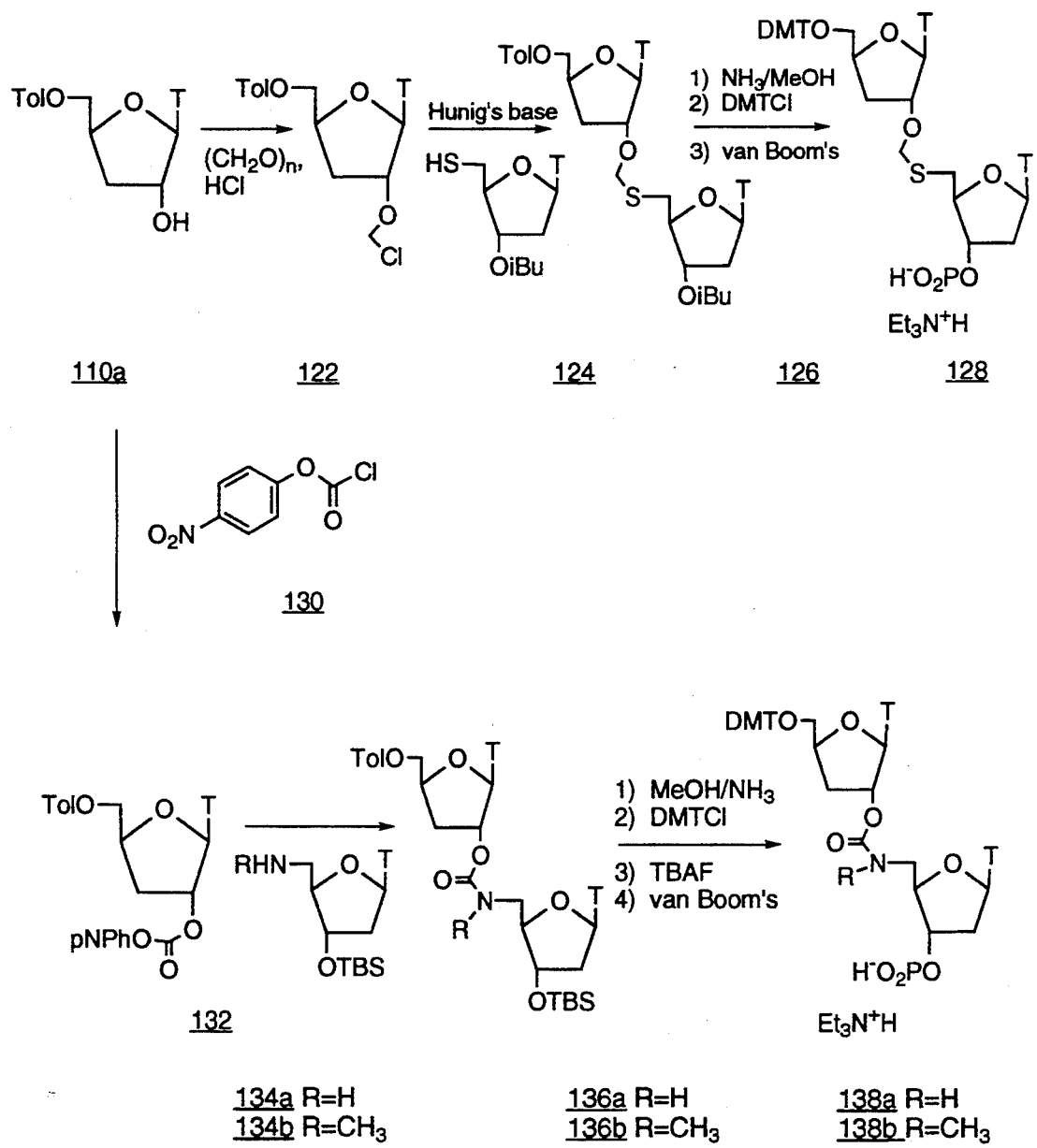

Preparation of Compounds 128, 138a, 138b. This Example, depicted in FIG. 17, shows two synthesis reactions for the preparation either of 5',2' carbamate or 5',2' methyl carbamate linkages.

Compound 110a (prepared using the procedure shown in FIG. 16) was dissolved in CH$_2$Cl$_2$ and cooled to 0° C. Paraformaldehyde was added and HCl (anhydrous) was passed through the suspension until a solution resulted. The flask was sealed and stored at 5° C. for 16 hours. After this time the solvent was removed to yield a white foam (compound 122) that was used without further purification in the following steps.

Compound 122 and compound 124 were dissolved in CH$_2$Cl$_2$ and Hunig's base was added. The resulting solution was stirred at room temperature for 3 hours. The solution was diluted with CH$_2$Cl$_2$ and subjected to an aqueous work-up. The resultant foam was subjected to column chromatography and eluted with 4% iPr/CH$_2$Cl$_2$ to yield a white foam containing compound 126.

Compound 126 was dissolved in MeOH and treated with MeONa (trace) at 50° C. for 1 hour. The solvent was removed and the solid subjected to column chromatography and eluted with 10%MeOH/CH$_2$Cl$_2$ to yield a white foam. This foam was dissolved in pyridine and treated with DMTCl and stirred at room temperature for 2 hours. The solvent was then removed and the residue treated to an aqueous work-up and the residual foam subjected to column chromatography and eluted with 6% MeOH/CH$_2$Cl$_2$ to yield a white foam. This foam was dissolved in pyridine/CH$_2$Cl$_2$ and cooled to 0° C. and treated with van Boom's reagent and stirred for 30 minutes. The solution was neutralized with TEAB (1N, pH=7) and extracted. The resulting white foam was subjected to column chromatography and eluted with 12% MeOH/0.5% TEA/CH$_2$Cl$_2$ to yield a white foam (compound 128).

In the other synthesis route depicted in FIG. 17, compound 110a was dissolved in pyridine and treated with p-nitrophenylchlorocarbonate and stirred at room temperature for 12 hours. The solvent was removed and the resulting foam subjected to column chromatography and eluted with 50%EtOAc/hexane to yield a white foam (compound 132).

Compound 132 was dissolved in DMF and treated with compound 134a and TEA. The solution was stirred at room temperature for 24 hours. The solvent was removed and the resulting yellow syrup subjected to column chromatography and eluted with 4% MeOH/CH$_2$Cl$_2$ to yield a white foam.

Compound 136b was prepared using the procedure described for compound 134a except that compound 134b was used as the reactant.

Compound 136a was dissolved in MeOH/NH$_3$ and heated in a sealed flask at 65° C. for 16 hours. The solvent was removed and the resulting white foam was crystallized from Et$_2$O to yield a white powder. This powder was dissolved in pyridine and treated with DMTCl and stirred at room temperature for 3 hours. The solvent was removed and the residue treated to an aqueous work-up and subjected to column chromatography and eluted with 4% MeOH/CH$_2$Cl$_2$ to yield a white foam. This foam was dissolved in THF and treated with TBAF and stirred at room temperature for 45 minutes. The solution was diluted with EtOAc and subjected to an aqueous work-up. The resulting white foam was then crystallized from Et$_2$O to yield a white powder. This powder was dissolved in pyridine/CH$_2$Cl$_2$ and cooled to 0° C. and treated with van Booms reagent and stirred for 30 minutes. The solution was neutralized with TEAB (1N, pH=7) and extracted. The resulting white foam was subjected to column chromatography and eluted with 12% MeOH/0.5-%TEA/CH$_2$Cl$_2$ to yield a white foam containing compound 138a.

Compound 136b was used in the same fashion as described just above in the preparation of compound 138a to yield compound 138b.

Example 13.

RNA and DNA duplex and DNA-triplex experiments utilizing certain desirable substitute linkages of this invention were conducted to determine those linkages' effect on the Tm values of the resulting oligomers. These experiments were carried out in a buffered solution (140 mM KCl, 5 mM Na$_2$HPO$_4$, and 1 mM MgCl$_2$) at pH=6.6 (except for the 2',5'-carbamate which was buffered at pH=7.0) according to the following protocol: 0.15 ODs of the target RNA/DNA was combined with 0.1 OD of the oligomer being assayed in a sterile eppendorf tube and dried. To this mixture was added 300 of Tm buffer and the solution was stirred. Tm values were then determined by a first derivative plot of absorbance versus temperature. Thermal denaturation analysis was carried out with a heating rate of 0.25° C./min and absorbance was monitored at 260 nm. The test oligomers that were synthesized for analysis were of the following sequence: 5'-TCmTCmTCmTCmTCmT*TT*TT-3' (SEQID No:4) where T=thymidine, Cm=5-methyl -2'-deoxycytidine, and T*T=a thymidine-thymidine dimer with an experimental linkage of the structure detailed in Table 2 below. All other linkages were phosphodiester.

Target Duplex Sequence (DNA)

5' AGAGAGAGAGAAAAA (3'SEQID No.:5) target strand

3' TCTCTCTCTCTTTTT 5' (SEQID No. 6) complement of target

Single Stranded Target (DNA or RNA)
5' AAAAAGAGAGAGAGA 3' (SEQ ID No: 7)
(T=U for RNA)

The linkage designated 5',2' thioformacetal has sulfur linked to the 5' carbon and the linkage designated 2',5' thioformacetal has sulfur linked to the 2' carbon. Similarly, the linkages designated 5',2' carbamate and 5',2' methyl carbamate have nitrogen linked to the 5' carbon atom (e.g. compounds 138a and 138b) and the 2',5' carbamate linkage has nitrogen linked to the 2' carbon atom (e.g. compound 120).

TABLE 2

| Compound | DNA-duplex | | DNA-RNA duplex | | DNA-triplex | |
|---|---|---|---|---|---|---|
| | Tm | °C./subst | Tm | °C./subst | Tm | °C./subst |
| control | 49 | — | 62.5 | — | 29.8** | — |
| 1* | 53.5 | +2.2 | 61.0 | −0.8 | 26.5** | −1.7 |
| control | 49 | — | 62.0 | — | 39.1 | — |
| 2 | 53.0 | +2.0 | 60.5 | −0.8 | 45.1 | +3.0 |
| 3 | 53.0 | +2.0 | 61.0 | −0.5 | 45.3 | +3.1 |
| control | 49.5 | — | 61.5 | — | 39.1 | — |
| 4 | 53.0 | +1.8 | 58.5 | −1.5 | 39.0 | 0 |
| control | 49.5 | — | 61.5 | — | | |
| 5 | 48.5 | −0.5 | 61.0 | −0.25 | | |
| control | 49.5 | — | 62.5 | — | 40.4 | |
| 6 | 48.5 | −0.5 | 61.5 | −0.5 | 40.4 | 0 |

*linkage type: 1 = 2',5' carbamate; 2 = 5',2' carbamate; 3 = 5',2' methyl carbamate; 4 = 5',2' thioformacetal; 5 = 2',5' thioformacetal; 6 = 2',5' formacetal.
**pH 7.0

Example 14.

Figure 9:
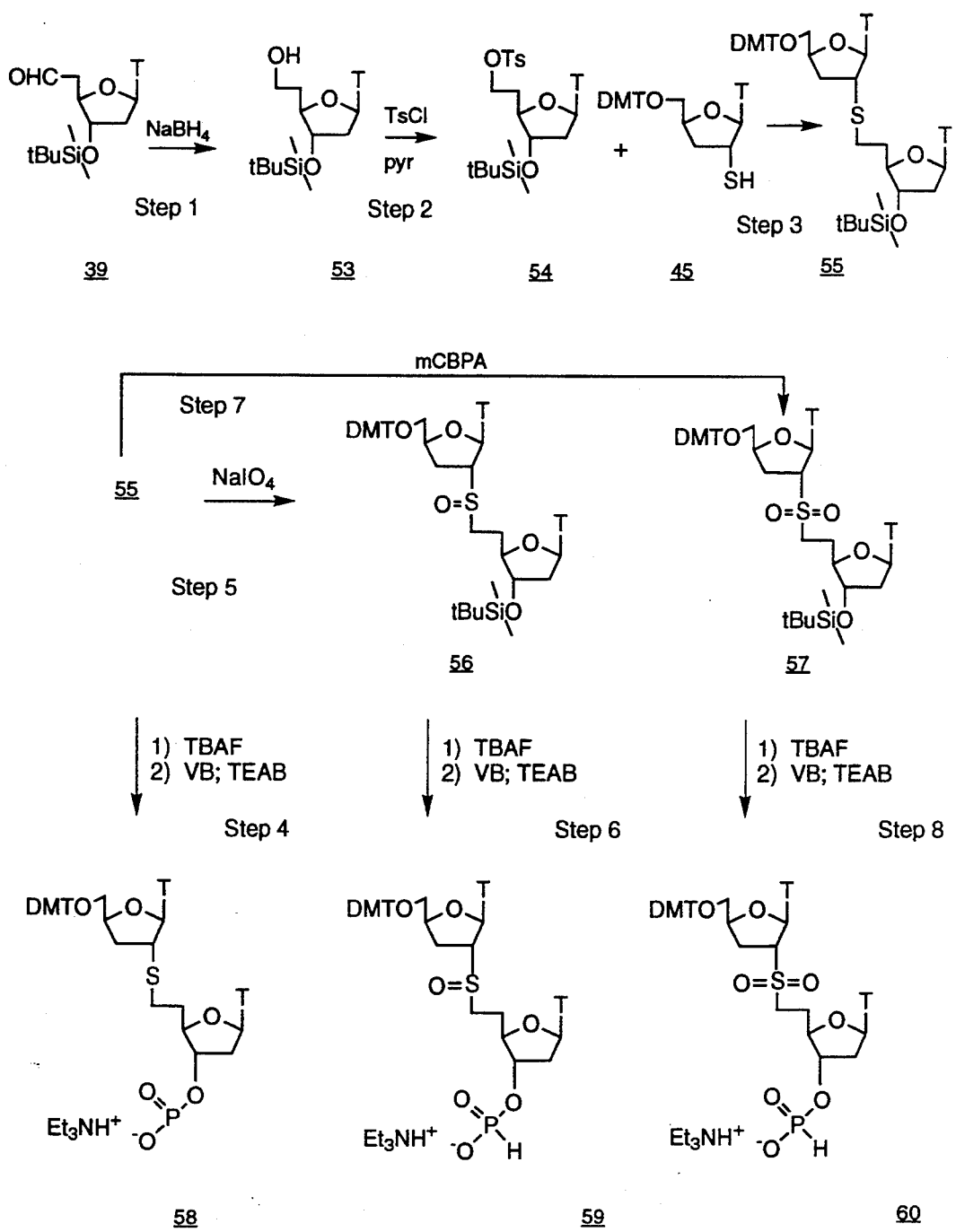

The dimer, 55, shown in FIG. 9 having a two atom long sulfur-containing linkage was synthesized as follows. The nitrile 38 was synthesized by adding to a solution of 3'-silylthymidine (2.33 g, 5.0 mmol) in DMF (25 mL), methyltriphenoxyphosphonium iodide (2.92 g, 6.5 mmol). The solution was then stirred for 18 h. Sodium cyanide (490 mg, 100 mmol) was added and the solution was stirred for 18 h. Methanol was added, and the solution was concentrated. The solution was partitioned between ethyl acetate (EtOAc) (100 mL) and Satd. NaHCO₃ (100 mL) and the crude product was washed with aqueous thiosulfate (100 mL), dried, concentrated, and chromatographed (EtOAc:hexane 4:6) to deliver the product 38 (1.14 g, 49%).

The aldehyde, 39, was synthesized as follows. To a solution of nitrile (1.14 g, 2.45 mmol) in toluene at −78° C., was added diisobutyl aluminum hydride (Dibal) (1.5M, 7.5 mL), and the solution was stirred for 30 min. Ethanol (2 mL) was added, followed by sodium fluoride (3.0 g), and water (2 mL). The mixture was filtered through celite, and the crude product was extracted with EtOAc (100 mL), dried, concentrated, and chromatographed (EtOAc:Hexane 4:6) to yield the product (625 mg).

53. 0.49 g (1 mmole) of aldehyde 39 was treated with NaBH₄ (38 mg, 1 mmole) in 5 mL of EtOH at rt. for 1 h. After removal of EtOH, the residue was extracted with EtOAc and washed with 1M citric acid. The organic layer was washed then with water, dried over Na₂SO₄, evaporated and finally purified by flash chromatography in methanol/methylene chloride (0:1001:99) to obtain 0.43 g (88%) of 53.

54. 0.4 g (0.8 mmole) of 53 was dissolved in 5 mL of dry DMF. At rt. 0.42 g (1.6 mmole) of triphenylphosphine and 0.53 g (1.6 mmole) of carbon tetrabromide were added into the reaction mixture. Two hours later TLC show completion of the reaction. The mixture was evaporated to dryness and extracted with EtOAc/water. The organic layer was dried over Na₂SO₄ and purified after concentration by flash chromatography in hexane/EtOAc (10:11:1) to yield 0.34 g (76%) of 54.

Thymidine-thymidine 2'-S-thioether (55). A solution of 0.14 g (0.25 mmole) of 54 was syringed to a 0° C. solution of 2'-mercapto-5'-O-DMT-2',3'dideoxythymidine (45) and 0.5 mL of sodium trimethylsilanolate (1M solution in THF) in methylene chloride (5.0 mL) under nitrogen. After stirring for 1 h, the reaction was added 10 mL of methylene chloride and quenched with water. The organic layer was separated, dried (Na₂SO₄), concentrated, and purified by flash chromatography in methanol/methylene chloride (0:100–5:95) to yield 0.13 g (51%) of T*T dimer 55.

Example 15.

The formacetal linkage shown in FIG. 20 was synthesized as follows. 5'-Toluyl-2'-methylthiomethylthymidine (2' MTMT): 5'-Toluylthymidine (0.12 g, 0.33 mmol) was dissolved in MeCN (4 mL) and Me₂S (0.24 mL, 3.3 mmol) was added and the solution was cooled to 0° C. Bz₂O₂ (0.32 g, 1.3 mmol) was added and the resulting solution was allowed to warm to 20° C. and stirred for 15 hours. Methanol was added and the solvent was removed in vacuo. The residue was dissolved in CH₂Cl₂ and washed with NaHCO₃ (sat) and brine. The organic layer was decanted, dried over Na₂SO₄, filtered, and reduced and the residue purified by column chromatography to yield a white foam.

T-T formacetal dimer: 2' MTMT (0.34 g, 0.81 mmol) and 3'-TBSthymidine (0.58 g, 1.63 mmol) were dissolved in benzene/CH₂Cl₂ (1/1, 10 mL) and stirred with 4A molecular sieves for 2 hours. The solution was then cooled to −10° C. and Br₂ (0.12 g, 0.77 mmol, in 0.5 mL CH₂Cl₂) was added and the solution allowed to warm to RT and stirred for 16 hours. The solution was then diluted with EtOAc and washed with NaHCO₃, H₂O, and brine.

Organic layer decanted, dried over Na₂SO₄, filtered, and reduced to a foam. The foam was dissolved in NH₃/MeOH (10 mL) and heated at 60° C. for 12 hours. The solvent was removed and the residue was subjected to column chromatography and eluted with MeOH/CH₂Cl₂ (2-3-4-6% of MeOH) to yield a whited foam; yield=0.12 g (26%). 5-DMT-3'-TBS t-t formacetal dimer: The 5'-OH dimer (0.12 g, 0.13 mmol) was protected as described previously except the product was purified by column chromatography and eluted with MeOH/CH₂Cl₂ (1-2-3-4% MeOH) to yield a white foam; yield=0.15 g (83%). 5'-DMT-T-T formacetal dimer-H-Phosphonate: 5'-DMT-3'-TBS T-T dimer was desilated as described before with TBAF but was purified by crystallization from Et₂O to yield a white powder; yield=0.08 g (80%). The H-phosphonate was prepared as described before but the compound was purified by column chromatography and was eluted with MeOH/CH₂Cl₂/TEA (5-10-15% MeOH/0.5% TEA) to yield a white foam; yield=0.062 g (74%).

Example 16.

The 2',5' thioformacetal linkage shown in FIG. 25 was synthesized as follows. 3'-Deoxy-5'-O-DMT-2'-O-methanesulfonyl-β-Darabinosylthymine. 2.18 g (4.0 mmole) of 3'-Deoxy-5'-O-DMT-β-Darabinosylthymine (Webb et al, *J Med Chem* (1988) 31:1475) was dissolved in 20 mL of dry pyridine. At 0° C., 0.5 mL of methane sulfonyl chloride (1.5 eq) was added into the solution, dropwise. After 2 h the reaction mixture was poured into ice water, the precipitate collected, then dissolved in methylene chloride, washed with water, dried over Na₂SO₄, and evaporated to dryness. The residue was purified on silica gel column in methanol/methylene chloride (0:100–2:98) to yield 2.2 (90%) of 3'-Deoxy-5'-O-DMT-2'-O-methanesulfonyl-βD-arabinosylthymine.

2'-S-Acetyl-2',3'-dideoxy-5'-O-DMT-thymidine. 3'-Deoxy-5'-O-DMT-2'-O-methanesulfonyl-βD-arabinosyl thymine (0.31 g, 0.5 mmole) was heated with potassium thioacetate (0.3 g, 5.2 mmole) in 5 mL of dry DMF for 2 h. The reaction mixture was evaporated to dryness. The residue was then dissolved in 20 mL of methylene chloride and washed with 20 mL 10% sodium bicarbonate solution and with 20 mL of water. The organic phase was dried over Na₂SO₄ and evaporated to dryness. The residue was purified on silica gel column in methanol/methylene chloride (0:100–2:98) to yield 0.24 (79%) of 2'-S-acetyl-2',3'-di deoxy-5'-O-DMT-thymidine.

2'-Mercapto-2',3'-dideoxy-5'-O-DMT-thymidine. 2'-S-acetyl-2',3'-dideoxy-5'-O-DMT-thymidine was treated with saturated ammonia in cold methanol for 30 min. Then the mixture was evaporated under reduced pressure with the exclusion of oxygen. Proton NMR shows 95% conversion to 2'-Mercapto product. The residue was used for the next step without further purification.

3'-O-Isobutyrylthymidine. To a solution of 5'-O-DMT-Thymidine (5.44 g, 10.0 mmol) in pyridine (30 mL) was added isobutyric anhydride (3.3 mL, 20.0 mmol) dropwise and the mixture was stirred at 20° C. for 18 h. The reaction was quenched with methanol (2.5 mL) and concentrated in vacuo. The crude product was extracted with methylene chloride (30.0 mL), washed with saturated aqueous sodium bicarbonate (30.0 mL), dried over Na₂SO₄ and concentrated. The residual oil was dissolved in 25% ethanol/methylene chloride (100 mL) and treated with p-toluenesulfonic acid (2.85 g, 15 mmol) at 0° C. After 0.5 h, the orange-red solution was quenched with saturated aqueous sodium bicarbonate (300 mL), and the organic layer was dried (Na₂SO₄) and concentrated. The crude product was dissolved in ethylacetate (25 mL) and precipitated by addition of hexane (250 mL) and cooled to −10° C. for 18 h. The mixture was filtered, and the precipitate was dried under high cacuum to afford 3'-O-isobutyrylthymidine (62%).

Thymidine-thymidine (2',5') thioformacetal. Into a solution of 3'-O-isobutyrylthymidine (0.312 g, 1.0 mmol), paraformaldehyde (45 mg, 1.5 mmol) and methylene chloride (10.0 mL) at 0° C. was bubbled anhydrous hydrogen chloride for 10 min, and the solution was held at 0° C. for 2 h. The solution was thoroughly dried (Na₂SO₄), and the solvent was evaporated to afford the chloromethyl ether. This chloromethyl ether was dissolved in methylene chloride (5.0 mL) and added dropwise to a 0° C. solution of 2'-mercapto-5'-O-DMT-2',3'-dideoxythymidine (prepared from 0.6, 1.0 mmol of correspondent thioacetate) and diisopropylethylamine (DIPEA, 0.5 mL) in methylene chloride (5.0 mL). After stirring for 1 h, the reaction was quenched with saturated aqueous sodium bicarbonate (10.0 mL). The organic layer was separated, dried (Na₂SO₄), concentrated, and purified by flash chromatography in methanol/methylene chloride (0:100–5:95) to yield 0.27 (65%) T*T dimer. The resulting product was treated with sodium methoxide (0.20 g, 3.64 mmol) in methanol (20 mL) for 1 h. The reaction was quenched with acetic acid (1M solution) and concentrated. The crude product was extracted with methylene chloride, dried (Na₂SO₄) and purified by flash chromatography in methanol/methylene chloride (1:99–7:93) to deliver the product (0.17 g, 70%).

H-Phosphonate of T*T dimer. To a solution of PA (1.0M in methylene chloride, 0.4 mmole), methylene chloride (5 mL), and pyridine (0.76 g, 0.8 mmole) at 0° C. was added the T*T dimer (0.16 g, 0.20 mmole) in methylene chloride (2 mL). The reaction mixture was stirred at RT for 15 min, diluted with methylene chloride (10 mL), and quenched with TEAB (1M aqueous solution, 10 mL). The organic phase was dried (Na₂SO₄) and evaporated. Subsequent purification by flash chromatography in TEA/methanol/methylene chloride (0.5:2:97.5–0.5:5:94.5) delivered 0.14 g (72%).

Example 17.

Reduction of thymidine α,β-unsatured aidehyde (TUA) to thymidine allyl alcohol (TAA). 0.5 g (1.0 mmole) of TUA (Montgomery et al, *J Org Chem* (1981) 46:594; U.S. Pat. No. 4,822,316) was treated with NaBH₄ (38 mg, 1.0 mmole) and 0.16 mL (1.0 mmole) of triethylsilane in 5 mL of THF at rt. for 1 h. After removal of THF the residue was extracted with EtOAc and washed with 1M citric acid. The organic layer was washed then with water dried over Na₂SO₄, evaporated with finally purified by flash chromatography in methanol/methylene chloride (0:100–1:99) to obtain 0.46 g (91%) of TAA.

Bromination of allyl alcohol TAA. 0.5 g (1.0 mmole) of TAA was dissolved in 5 mL of dry DMF. At 20° C. 0.53 g (2.0 mmole) of triphenylphosphine and 0.66 g (1.6 mmole) of carbon tetrabromide were added into the reaction mixture. Two hours later the reaction was shown to be complete by TLC. The mixture was evaporated to dryness and extracted with EtOAc/water. The organic layer was dried over Na₂SO₄ and purified after concentration by flash chromatography in hexane/EtOAc (1:1–1:4) to yield 0.45 g (81%) of thymidine allyl bromide (TAB).

Thymidine-thymidine 2'S allylsulfide (TTAS-Si). A solution of 0.57 g (1.0 mmole) of TAB was synringed to a 0° C. solution of 2'-mercapto-5'-O-DMT-2',3'-dideoxythymidine (prepared from 0.6 g, 1.0 mmole of correspondent thioacetate) and 0.35 mL (2 eq.) of diisopropyl ethyl amine (DIPEA) in methylene chloride (5.0 mL) under nitrogen. After sitrring overnight, the reaction was added 10 mL of methylene chloride and quenched with water. The organic layer was separated, dried (Na₂SO₄), concentrated, and purified by flash chromatography in methanol/methylene chloride (0:100 –3:97) to yield 0.75 g (72%) of T*T dimer TTAS-Si.

Desilylation on the 3'-position of T*T dimer —(TTAS-Si). TTAS-Si (0.63 g, 0.6 mmole) was dissolved in 5 mL of THF and treated with 1 mL of 1M TBAF/THF for 1 h. The reaction was concentrated. The crude product was extracted with methylene chloride, dried (Na₂SO₄) and purified by flash chromatography in methanol/methylene chloride (1:99–7:93) to deliver the product (TTAS) (0.31 g, 63%).

H-phosphonate of T*T dimer. To a solution of PA (1.0M in methylene chloride, 0.4 mmole), methylene chloride (5 mL), and pyridine (0.76 g, 0.8 mmole) at 0° C. was added to T*T dimer (TEAS) (0.16 g, 0.20 mmole) in methylene chloride (2 mL). The reaction mixture was stirred at rt for 15 min., diluted with methylene chloride (10 mL), and quenched with TEAB (1M aqueous solution, 10 mL). The organic phase was dried (Na₂SO₄) and evaporated. Subsequent purification by flash chromatography in TEA/methanol/methylene chloride (0.5:2:97.5–0.5:5:94.5) and then in TEA/H₂O/acetonitrile (0.5:2:97.5–0.5:5:94.5) delivered 0.14 g (69%). t )

Example 18.

3',5' Allylether and 3',5' allylsulfide substitute linkages were synthesized as follows. The 5'-hydroxyl group of 3'-t-butyldiphenylsilylthymidine was oxidized and homologated to give the unsaturated aidehyde (Montgomery et al, *J Org Chem* (1981) 46:594) as shown in FIG. 30–1. Reduction of the aidehyde gave the allylic alcohol which was then converted to the allyl bromide as shown. The allyl bromide was then added to 5'-O-DMT-thymidine pretreated with 5 equivalents of NaH in THF at 0° C. for $X^2=O$ to yield the dimer shown in FIG. 30–2.

For $X^2=S$, the allyl bromide was coupled to 5'-O-DMT-thymidime using methylene chloride and DIPEA as a basic agent. Both dimers were desilylated by TBAF in THF to yield a derivative having a free 3-hydroxyl, followed by reaction with 2-chloro-4-H-1,3,2-benzodioxa-phosphorin-4-one (PA) in methylene chloride/pyridine to yield the 3'-H-phosphonate as shown in FIG. 30–3.

Conversion of the 3',5'-allylether linked dimer to the saturated propylether derivative (3'—O—CH₂—CH₂—5') was accomplished by low pressure hydrogenation with H₂/Pd/C. Synthesis of a saturated 3',5' propyl sulfide linked dimer (3'—S—CH₂—CH₂—5') was accomplished as shown in FIG. 30–4. The monomers shown were coupled using sodium trimethylsilanoate (TMSONa) in THF. Dimers containing other bases, such as bases of structure IX, cytosine, 5-(1-propynyl)uracil, 5-(1-propynyl)cytosine, 7-deaza-7-(1-propynyl)adenine, 7-deaza-7-(1-propynyl)guanine, adenine or guanine, are synthesized in a similar fashion. For synthesis of oligomers containing allyl ether linkages, bases containing an exocyclic amine are preferably protected using a group stable to NaH such as diisobutylformamidine. For synthesis of oligomers containing allyl sulfide linkages, bases are optionally protected using standard protected bases such as N⁴-benzoylcytosine, N⁴-benzoyl-5-(1-propynyl)cytosine, N⁶-benzoyladenine, N²-isobutyrylguanine and the like.

Example 19.

The H-phosphonate dimers of Example 18 were incorporated into oligomers and tested for binding to single stranded DNA or single stranded RNA target oligomers. All linkages and substitute linkages were 3',5' and all residues designated "C" were 5-methyl-cytosine.

| Linkage type | Sequence |
| --- | --- |
| target | 3' AGA GAG AGA GAA AAA 5' (SEQ ID NO: 8) |
| phosphodiester | 5' TCT CTC TCT CTT TTT 3' (SEQ ID NO: 9) |
| 3'-allyl ether | 5' TCT CTC TCT CT#T T#TT 3' (SEQ ID NO: 10) |
| 3'-allyl sulfide | 5' TCT CTC TCT CT#T T#TT 3' (SEQ ID NO: 11) |
| 3'-propylether | 5' TCT CTC TCT CT#T T#TT 3' (SEQ ID NO: 12) |
| 3'-propyl sulfide | 5' TCT CTC TCT CT#T T#TT 3' (SEQ ID NO: 13) |

-substitute linkage of the indicated type replaced the phosphodiester linkage at the position shown, all other linkages were phosphodiester linkages.

The following Tm (° C.) results were obtained.

| oligomer | target oligomer | |
| --- | --- | --- |
|  | ssRNA(ΔTm/sub.) | DNA(ΔTm/sub.) |
| phosphodiester | 62.5 | 55.5 |
| 3'-allylether | 60.5 (−1.0) | 49.0 (−3.25) |
| 3'-allylsulfide | 59.5 (−1.50) | 49.5 (−3.0) |
| 3'-propylether | 58.5 (−2.0) | 49.0 (−3.25) |
| 3'-propyl sulfide | 59.0 (−1.75) | 49.0 (−3.25) |

Example 20.

The ability of oligomers containing bases of formula IX to form high melting duplexes is shown in the following data. The polycyclic cytidine derivatives of formula IX were incorporated into two test 15-mer oligonucleotides by conventional phosphodiester chemistry. The test sequence is complementary to the sequence of "compound 26" RNA described in Jones et al., *J Org Chem* op cit. In one test oligonucleotide ("homo-3"), 3 of the designated polycycles were inserted into the olignucleotide in tandem, i.e., as XXX (the C triplet in the test oligo). In the other "alt-3"), the 3 polycycles were not adjacent but instead were separated by from 1 to 5 bases (the nonadjacent cytidine bases in the test oligo). The remainder of the bases were C and T as deduced from the reference sequence. A comparison oligonucleotide containing a 5-propyne deoxy C triplet (analogous to the homo-3 oligonucleotide containing the bases of this invention, "5-Propyne dC (homoC)") was prepared and tested in the same assay system. ΔTm was calculated against the Tm of a control oligonucleotide containing the same sequence, but with 5-methyl deoxy C in place of the cytidine bases of the test oligonucleotides. The structures of the test polycycles are shown below, as are their designations (e.g., "benzene tricyclic C") for the Tm's shown in the Table 3 below ("dR" is deoxyribose).

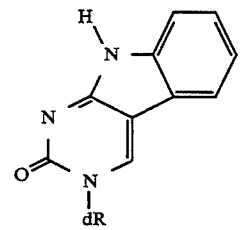

Benzene Tricyclic Cytidine

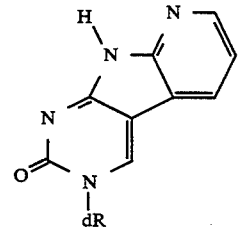

2-Pyridine Tricyclic Cytidine

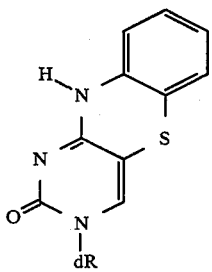

Phenothiazine Tricyclic Cytidine

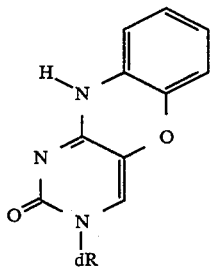

Phenoxazine Tricyclic Cytidine

TABLE 3

Tricyclic Cytidine Derivatives for Enhanced RNA Affinity

| Cytidine Modification | Δ Tm RNA (°C.) | Δ Tm Substitution (°C.) |
|---|---|---|
| 5-Propyne dC (homo-3) | +8.0 | +2.7 |
| Benzene Tricyclic dC (homo-3) | +8.0 | +2.7 |
| Benzene Tricyclic dC (alt-3) | 0.0 | 0.0 |
| 2-Pyridine Tricyclic dC (homo-3) | +7.5 | +2.5 |
| 2-Pyridine Tricyclic cD (alt-3) | 0.0 | 0.0 |
| Phenathiazine Tricyclic dC (homo-3) | +13.0 | +4.3 |
| Phenathiazine Tricyclic dC (alt-3) | +4.5 | +1.5 |
| Phenoxazine Tricyclic dC (homo-3) | +15.0 | +5.0 |
| Phenoxazine di-methyl Tricyclic dC (homo-3)* | +17.5 | +5.8 |
| Phenoxazine Tricyclic dC (alt-3) | +6.5 | +2.2 |

Tm for the tabulated oligonucleotides is obtained by adding 62.5° C. to the Δ Tm figure.
*Example G.3.

This data demonstrates the enhancement in melting point afforded by the oligonucleotides of this invention, particularly those having tandem arrangements of the novel bases. In general, such tandem arrangements will contain from 2 to about 10 polycyclic bases, which can be the same or different polycycles but generally are the same polycycle. They also optionally are copolymerized with purine or pyrimidine bases containing known alkynyl substitutions (PCT 92/10115 and U.S. Ser. No. 08/050,698), in particular pyrimidine bases substituted at the 5 position with a carbon atom which is bonded to another atom by a Pi bond.

Figure 35:
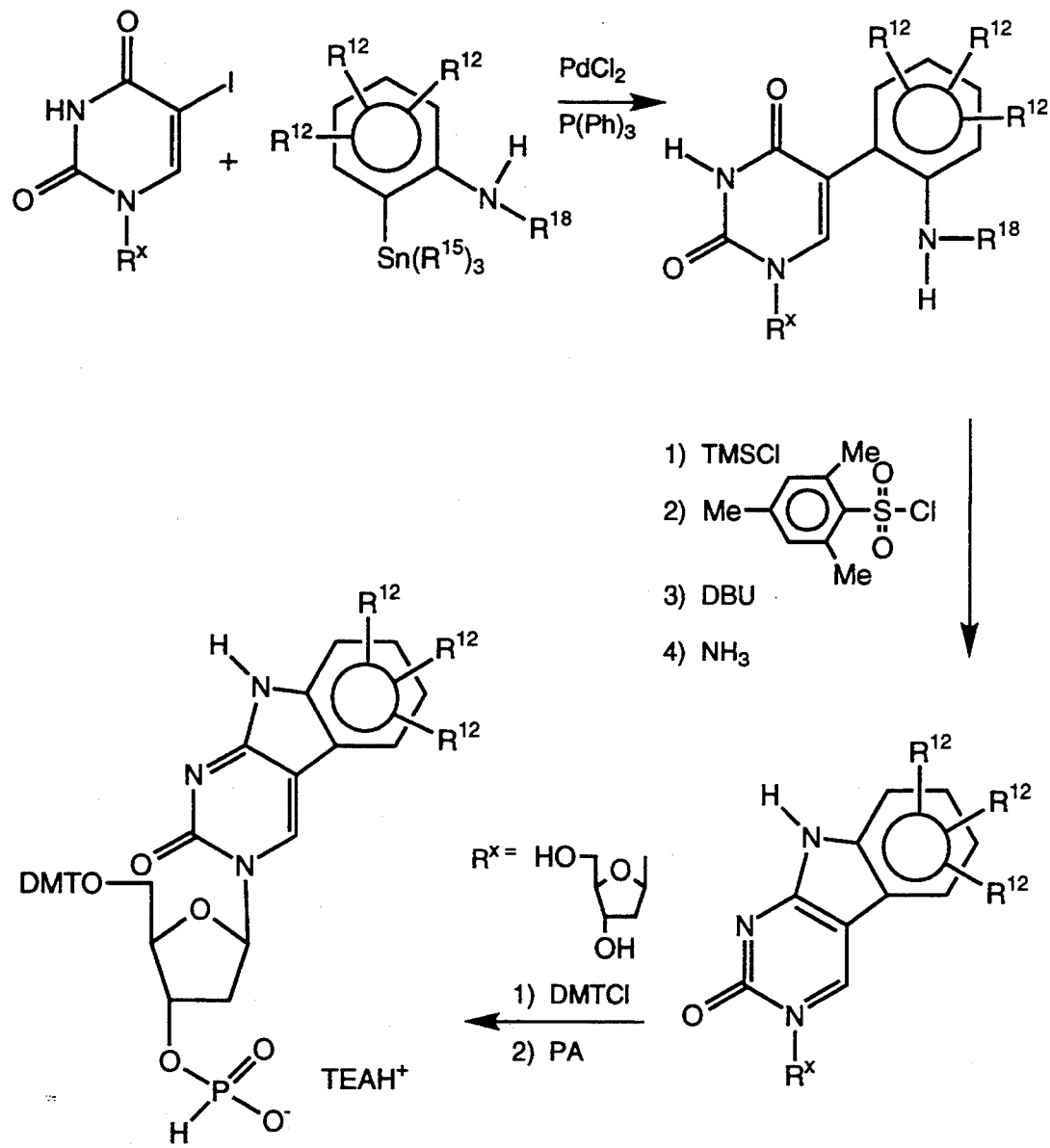

EXAMPLE 21 Representative Application of the Scheme of FIG. 35

A. 5-(2-N-tert-butoxycarbonyl aniline) 5'-dimethoxytrityl-2'-deoxyuridine (DMT-AU).

The synthesis of N-(tert-butoxycarbonyl)-2-(trimethylstannyl) aniline (BocSnA) was as reported in Salituro et al, J. Org Chem (1988) 53:6138–6139.

1.5 g of 5-iodo-2'-deoxyuridine, 5 g of BocSnA and 50 mg of palladium dichloride bistriphenyl phosphine were dissolved in 5 ml DMF and sealed under $N_2$. The reaction was heated for 16 h at 50° C. The reaction was cooled, diluted with EtOH, 1 ml of triethylamine was added and filtered through Celite. The clear solution was then concentrated under reduced pressure and flash chromatographed on silica gel with a gradient of methanol in methylene chloride (0%–10%). Upon concentration the nucleoside was rendered anhydrous by pyridine addition and evaporation which was subsequently reacted with 880 mg of dimethoxytrityl chloride in 10 ml of pyridine for 1 h at 20° C. The reaction was quenched with methanol and partitioned into methylene chloride and $H_2O$. The organic phase was concentrated under reduced pressure and purified by flash chromatography on silica gel eluting with a gradient of isopropanol in methylene chloride (0%–4%). The yield was 720 mg of DMT-AU.

B. Dimethoxytrityl benzopyrimidine polycyclic nucleoside 700 mg of DMT-AU was treated with 3 ml of trimethylsilyldimethyl amine in 3 ml $CH_3CN$ for 2 h at 20° C. followed by evaporation at reduced pressures redissolving in $CH_3CN$ and reevaporation 2 times. The residue was then dissolved in 7 ml $CH_3CN$ and 0.67 ml of triethylamine, 11 mg of 4-dimethylaminopyridine and 420 mg of mesitylenesulfonylchloride were added under $N_2$ and stirred for 4 h at 20° C. 0.72 ml of 1,8 diazabicyclo [5.4.0] undec-7-ene was added and stirred 30' at 20° C. followed by 0.015 ml of $H_2O$ and stirring for 1 h. Workup consisted of partitioning between methylene chloride and 0.5 M aqueous dibasic sodium phosphate. Evaporation under reduced pressure of the organic phase followed by silica gel chromatography using an isopropanol gradient in methylene chloride (0%–5%) yielded 300 mg of tricyclic nucleoside. The nucleoside was converted into its 3' hydrogen phosphonate derivative and incorporated into oligonucleotides by standard procedures (see Jones et al, J Org Chem (1993) 58:2983–2991).

Figure 36:
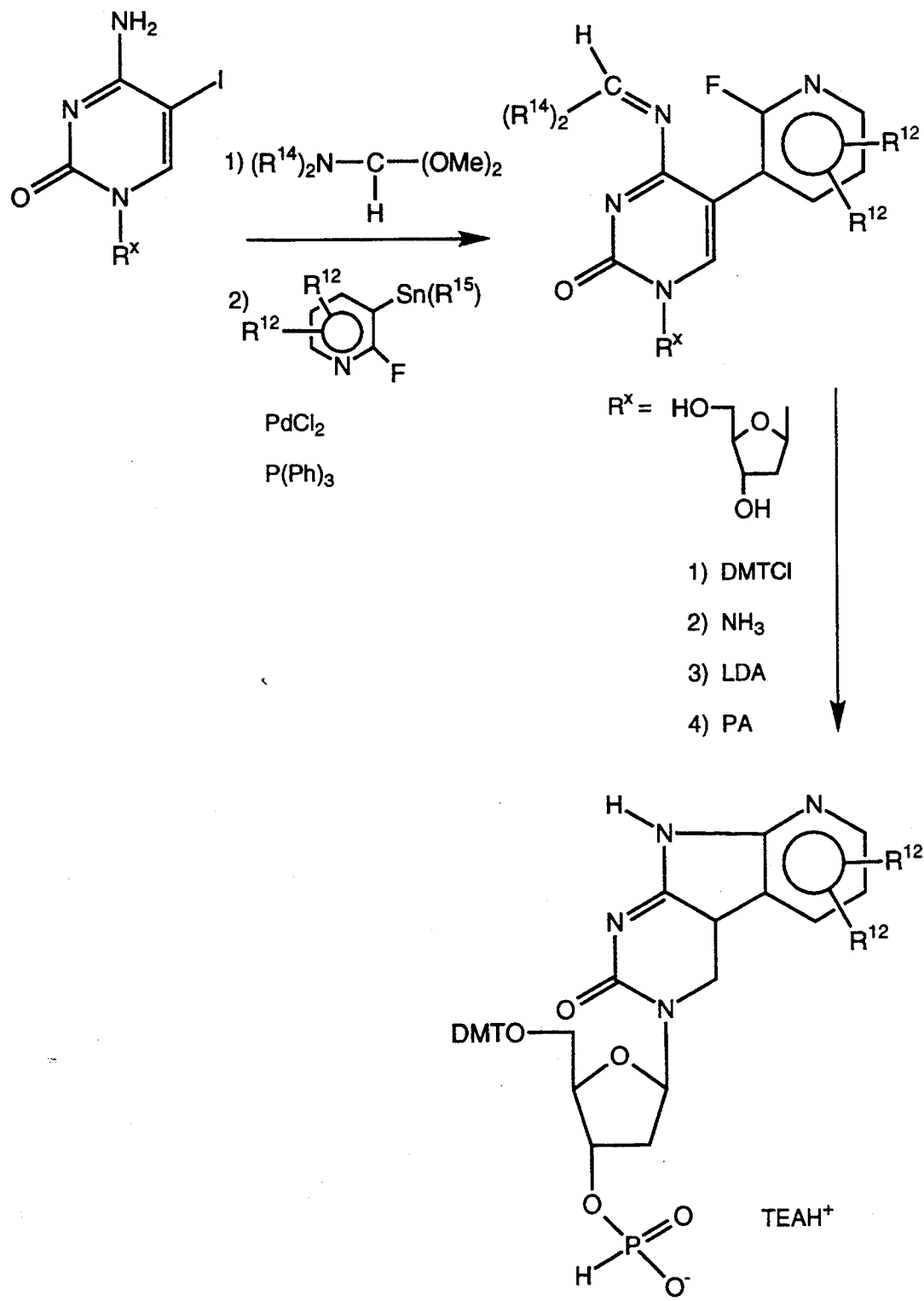

EXAMPLE 22 Representative Application of the Scheme of FIG. 36

A. 2-Fluoro-3-trimethylstannyl-pyridine (FSnP)

Metalation of 2-fluoropyridine was performed as described in Estel et al, J Org Chem (1988) 53:2740–2744. The lithium anion was quenched with 1 eq. of trimethyl tin chloride in THF (1 M) at −78° C. and stirred for 30', quenched with 1 M sodium bicarbonate and extracted with ethyl acetate. Upon $Na_2SO_4$ drying and evaporation under reduced pressure the resulting oil was used without further purification.

B. Deoxycytidine-5-(3-(2-fluoropyridine))-5'dimethoxytrityl-2'-deoxycytidine (DMT-FPdC)

500 mg of 5-Iodo-2'-deoxycytidine was heated at 100° C. in 4 ml DMF and 2 ml DMF dimethyl acetal. After 2 h. the reaction was cooled and concentrated under reduced pressure. The residue was dissolved in 4 ml DMF, 2 ml FSnP and palladium chloride bistriphenylphosphine was added under $N_2$ and heated for 16 h. at 50° C. The reaction cooled and 4 ml of ammonia-saturated methanol was added and stirred for 4 h. at 20° C. The reaction was concentrated under reduced pressure and precipitated into anhydrous ethyl ether. The precipitate was dried and dissolved in pyridine, evaporated under reduced pressure and redissolved in 4 ml pyridine. 400 mg of dimethoxytritylchloride was added and after 30 minutes at 20° C., the reaction was quenched with MeOH, extracted with methylene chloride and H₂O. The organic layer was concentrated and purified by flash chromatography on silica gel using a methanol gradient in methylene chloride (5–10%).

C. Dimethoxytrityl-2-pyridine Polycyclic Nucleoside 0.3 ml of dry diisopropylamine was combined with 4 ml dry THF under $N_2$ and cooled to 0° C. 1.2 ml of 1.7 M butyllithium in THF was added dropwise and the reaction was stirred for 5 min. 200 mg of DMT-FPdC in 10 ml of dry THF was then added dropwise. After 1 h. at 0° C. the reaction was quenched with 1M sodium bicarbonate and extracted with ethyl acetate. The organic layer dried with $Na_2SO_4$ and was concentrated under reduced pressure and purified by flash chromatography on silica gel using a gradient of methanol (5–10%) in methylene chloride. After concentration under reduced pressure the compound was converted to H-phosphonate derivative by standard procedures (see Jones et al, *J Org Chem* (1993) 58:2983–2991).

Figures 1, 38A:
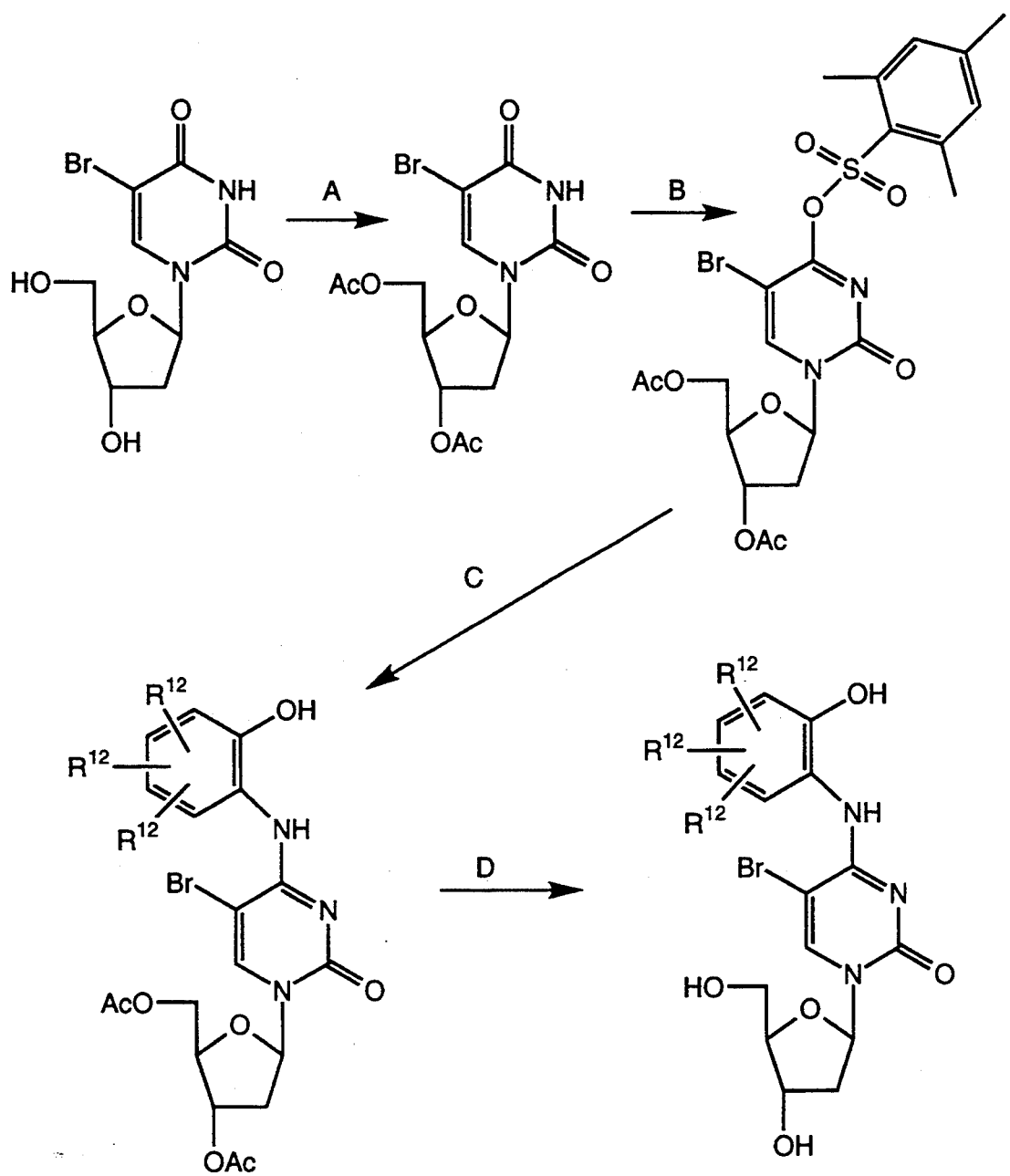
Figures 2, 38A:
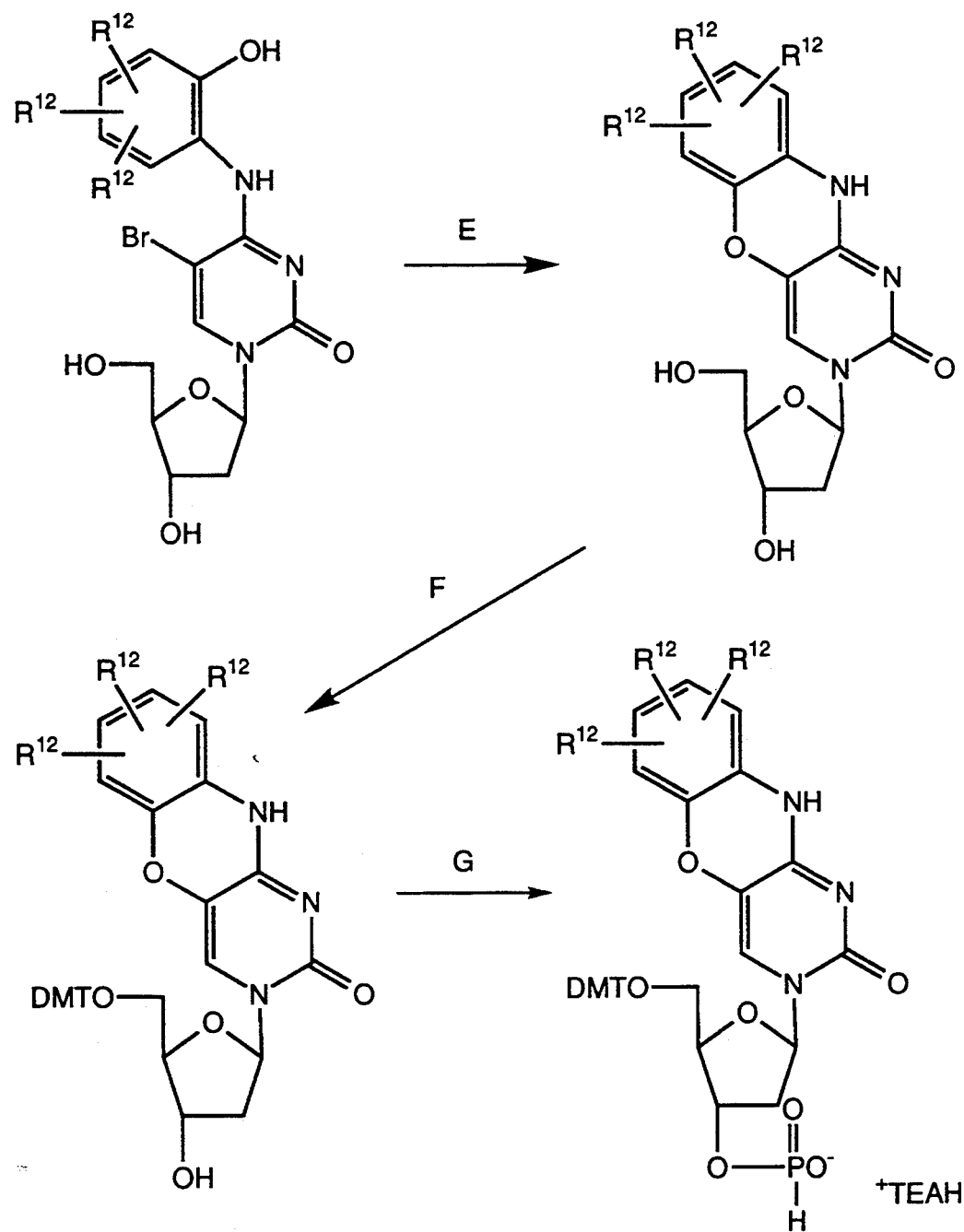
Figures 1, 39A:
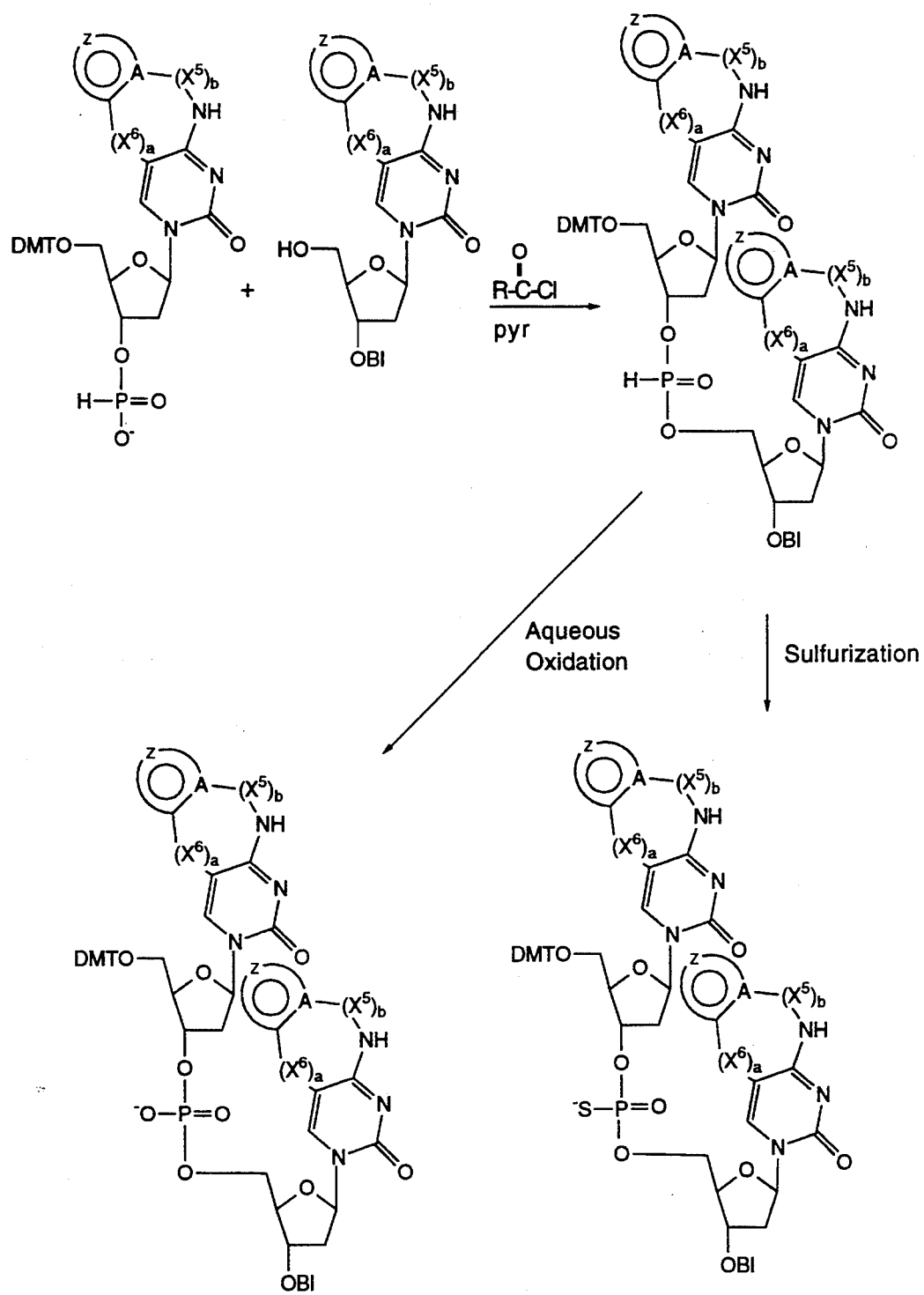
Figures 2, 39A:
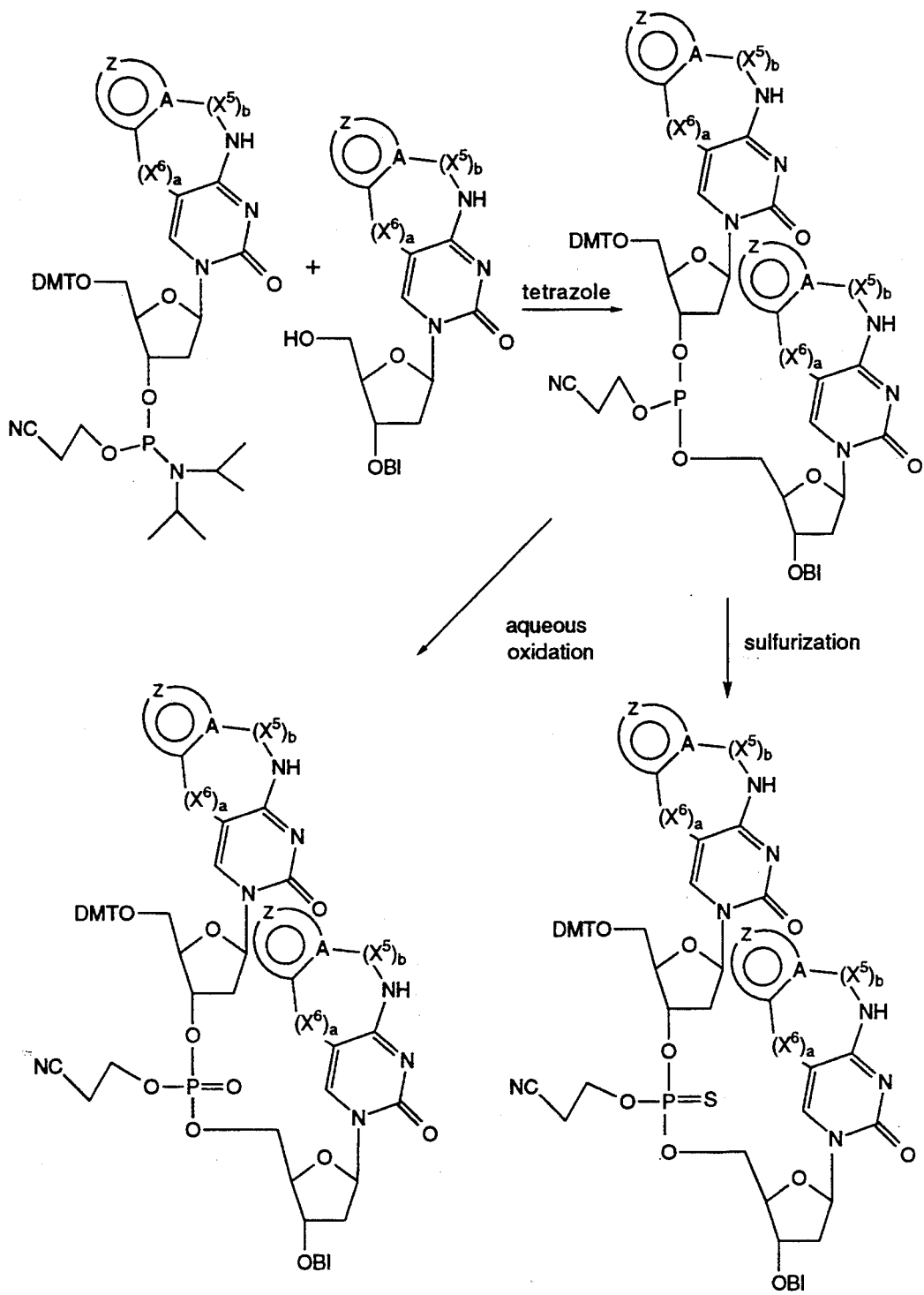
Figures 3, 39A:
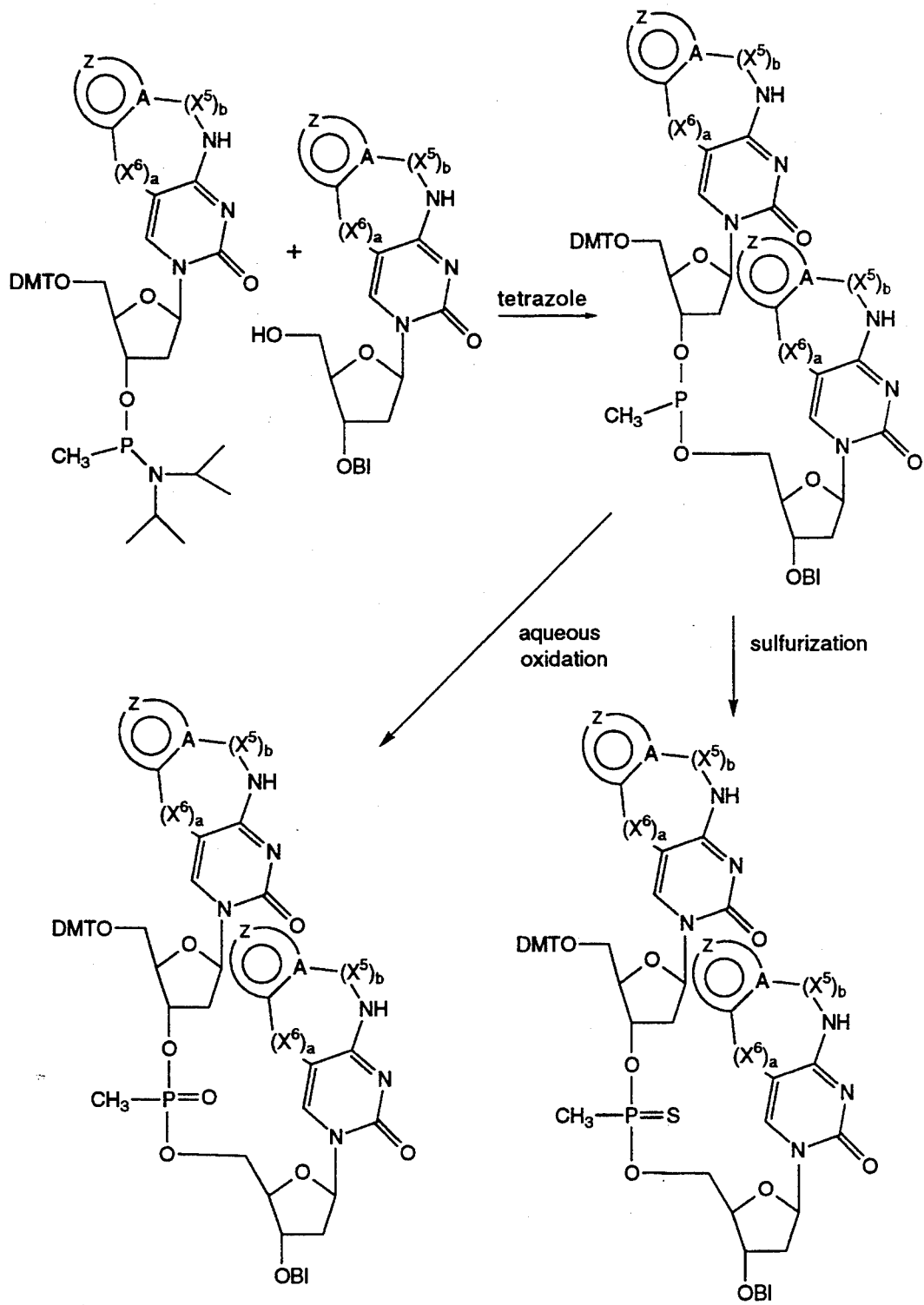

EXAMPLE 23 Representative Application of the Scheme of FIGS. 38-1 and 38-2.

A. 3′,5′,-Diacetyl -5-bromo-2′-deoxyuridine

5-Bromo-2′-deoxyuridine (7.3 g; 23.7 mmol) was dissolved in pyridine (30 ml) and treated with acetic anhydride (10 g; 95 mmol) at room temperature for 3 h. The reaction was quenched with methanol and concentrated. The residue was partitioned between $CH_2Cl_2$ and saturated $NaHCO_3$ aq. solution. The organic layer was separated, dried over $MgSO_4$, then concentrated to give the title compound quantitatively.

B.1.
5-Bromo-3′,5′-diacetyl-$N^4$-(2-hydroxyphenyl)-2′-deoxycytidine

To a solution of 3′,5′-diacetyl-5-bromo-2′-deoxyuridine (8.5 g; 21.7 mmol), methylene chloride (100 ml), triethylamine (8.8 g; 87 mmol) and DMAP (0.13 g) was added 2-mesitylsulfonyl chloride (9.5 g; 43.4 mmol). After stirring at room temperature for 18 h. DBU (6.6 g; 43.5 mmol) and 2-aminophenol (9.5 g; 87 mmol) were added and the solution was stirred for 1 hr. The reaction mixture was concentrated and the residue was partitioned between ethyl acetate and saturated sodium bicarbonate aq. solution. The organic layer was purified by flash column chromatography on silica gel to yield the title compound.

B.2.
5-Bromo-3′,5′-diacetyl-$N^4$-(2-hydroxy-m-nitrophenyl)-2′-deoxycytidine

To a solution of 3′,5′-diacetyl-5-bromo-2′-deoxyuridine (4.8 g; 12 mmol), methylene chloride (50 ml), triethylamine (5.0 g; 50 mmol) and DMAP (0.10 g) was added 2-mesitylsulfonyl chloride (5.2 g; 24 mmol). After stirring at room temperature for 4 h., DBU (3.6 g; 24 mmol) and 2-amino-4-nitrophenol (7.4 g; 48 mmol) were added and the solution was stirred for 3 h. The reaction mixture was concentrated and the residue was partitioned between ethyl acetate and saturated sodium bicarbonate. The organic layer was purified by flash column chromatography on silica gel. The isolated product had some impurity and was triturated with ethyl acetate. The yellowish precipitate was filtered off and washed with methylene chloride to yield the title compound.

B.3.
5-Bromo-3′,5′-diacetyl-$N^4$-(2-hydroxy-3,5-dimethylphenyl)-2′-deoxycytidine The title compound was synthesized by the way of synthesis of compound 3.B.1. except that the reaction used 2-amino-4,6-dimethylphenol in place of 2-amino-4-nitrophenol. The reaction mixture was purified by flash column chromatography on silica gel to afford the desired compound which containing some impurity and was used for the next reaction without further purification.

B.4.
5-Bromo-3′,5′-diacetyl-$N^4$-[2-(3-hydroxynaphthyl)]-2′-deoxycytidine

To a solution of 3′,5′-diacetyl-5-bromo-2′-deoxyuridine (4.0 g; 10 mmol), methylene chloride (50 ml), triethylamine (4.0 g; 40 mmol) and DMAP (0.1 g) was added 2-mesitylsulfonyl chloride (4.4 g; 20 mmol). After stirring at room temperature for 6 h. DBU (3.0 g; 20 mmol) and 3-amino-2-naphthol (6.4 g; 40 mmol) were added and the solution was stirred for 4 h. at room temperature. The reaction mixture was concentrated, the residue was dissolved in ethyl acetate and washed with saturated sodium bicarbonate aq. solution, but the title compound was precipitated from solution. The precipitates were filtered off and washed thoroughly with ethyl acetate, then methylene chloride, and dried. A small quantity of title compound also was obtained from the filtrate.

C.1. 5-Bromo-$N^4$-(2-hydroxyphenyl)-2′-deoxycytidine

5-Bromo-3′,5′-diacetyl-$N^4$-(2-hydroxyphenyl)-2′-deoxycytidine (Ex.3.B.) (4.3 g; 8.9 mmol) was treated with saturated ammonium in methanol at room temperature for 3 h. and concentrated to dryness. The residue was triturated with methylene chloride/hexane (1/1). The off-white solid was filtered off, washed thoroughly with methylene chloride/hexane and dried.

C.2.
5-Bromo-$N^4$-(2-hydroxy-m-nitrophenyl)-2′-deoxycytidine

The title compound was prepared from compound 3.B.2. by the way of synthesis of compound 3.C.1.

C.3.
5-Bromo-$N^4$-(2-hydroxy-3,5-dimethylphenyl)-2′-deoxycytidine

The crude compound of 3.C.2. was treated with 100 ml of saturated $NH_3$ in methanol at room temperature for 5 h. then concentrated to dryness. The residue was partitioned between methylene chloride and saturated sodium bicarbonate aq. solution. The organic phase was isolated, dried and purified by flash column chromatography on silica gel affording the title compound.

C.4.
5-Bromo-$N^4$-[2-(3-hydroxynaphthyl)]-2′-deoxycytidine

The compound produced in example 3.B.4. (3.1 g; 5.8 mmol) was treated with saturated $NH_3$ in methanol (150 ml) at room temperature for 6 h. The reaction mixture was concentrated and the residue was triturated with methylene chloride/ethyl acetate. The precipitate was filtered off, washed thoroughly with methylene chloride, dried, yielding 2.5 g, 96%.

D.1. 2'-Deoxyphenoxazine Tricyclic dC

Potassium fluoride (4.3 g; 75 mmol) was added to an ethanol solution (150 ml) of the compound prepared in example 3.C.1. (3.0 g; 7.5 mmol). The resulting solution was refluxed for 3 days. The solution was cooled to room temperature, some precipitate was filtered off and the flitrate was concentrated to dryness and used for Example 3.F.1. without further purification.

D.2. 2'-Deoxy-p-nitrohenoxazine Tricyclic dC

A solution of the compound of Example 3.C.2. (2.4 g; 5.4 mmol), potassium fluoride (3.1 g; 54 mmol), ethanol (100 ml) and DMSO (30 ml) was placed in a bomb and reacted at 120° C. for 3 days. The reaction mixture was concentrated and purified by flash column chromatography on silica gel. The crude product was used for Example 3.E. without further purification.

D.3. 2'-Deoxy-2,4-dimethylphenoxazine Tricyclic dC

The title compound was synthesized by the same procedure as in Example 3.D.1., except that the dimethylphenyl compound of Example 3.C.3. was used as starting material.

D.4. 2'-Deoxy-naphthoxazene Tricyclic dC

The compound of example 3.C.4. (2.4 g; 5.3 mmol) and potassium fluoride (3.1 g; 53 mmol) were refluxed in ethanol (100 ml) for 4 days. The reaction mixture was cooled to room temperature and concentrated to dryness, yielding the title compound.

E. 3',5'-Diacetyl-2'-deoxy-p-nitrophenoxazine

The crude product of Example 3.D.2. (0.3 g) was dissolved in pyridine (10 ml) and reacted with acetic anhydride (3 ml) at room temperature for 3 h. The mixture was quenched with methanol, concentrated and partitioned between methylene chloride and saturated sodium bicarbonate aq. solution. The organic phase was purified by flash column chromatography on silica gel affording the title compound.

F.1. 5'-O-Dimethoxytrityl-2'-deoxyphenoxazine Tricyclic dC

The crude product of Example 3.D.1. was dissolved in pyridine (35 ml) and treated with 4,4'-dimethoxytrityl chloride (5 g; 14.7 mmol) at room temperature for 1.5 h, concentrated. The residue was dissolved in methylene chloride and washed with saturated sodium bicarbonate aq. solution. The organic phase was isolated, dried, concentrated, then purified by flash column chromatography on silica gel to yield the title compound. The nucleoside was converted into its 3' hydrogen phosphonate derivative and incorporated into oligonucleotides by standard procedures.

F.2. 5-O-Dimethoxytrityl-2'-deoxy-4-nitrophenoxazine Tricyclic dC

The compound of Example 3.E. (0.27 g; 0.608 mmol) was treated with saturated $NH_3$ in methanol (20 ml) at room temperature for 4 h, then concentrated. The residue was dissolved in pyridine (10 ml) followed by addition of 4,4'-dimethoxytrityl chloride (0.25 g; 0.73 mmol). After stirring at room temperature for 3 h., the reaction mixture was concentrated, then partitioned between methylene chloride and saturated sodium bicarbonate aq. solution. The organic phase was dried and purified by flash column chromatography on silica gel, affording the title compound.

F.3. 5'-O-Dimethoxytrityl-2'-deoxy-2,4-dimethylphenoxazine Tricyclic dC

The compound of Example 3.D.3 (0.3 g; 0.87 mmol) was dissolved in pyridine (5 ml) followed by addition of 4,4'-dimethoxytrityl chloride (0.4 g; 1.2 mmol) and DMAP (10 mg). The reaction mixture was stirred at room temperature for 2 h., concentrated, then partitioned between methylene chloride and saturated sodium bicarbonate aq. solution. The organic phase was isolated, dried and purified by flash column chromatography on silica gel affording the title compound. Unreacted compound (85 mg) was recovered from aq. solution.

F.4. 5'-O-Dimethoxytrityl-2'-deoxy-2-naphthoxazene Tricyclic dC

The compound of Example 3.D.4. was dissolved in pyridine (15 ml) followed by addition of 4,4'-dimethoxytrityl chloride (3.1 g; 9.1 mmol) and DMAP (15 mg). After stirring at room temperature 3 h., the reaction mixture was concentrated, then partitioned between methylene chloride and saturated sodium bicarbonate aq. solution. The organic solution was isolated, dried over $MgSO_4$, purified by flash column chromatography on silica gel affording the title compound.

G. 5'-O-Dimethoxytrityl-2'-deoxy-phenoxazine Tricyclic dC

The nucleosides (3.F.1., 3.F.2., 3.F.3., 3.F.4.) were converted into their 3' hydrogen phosphonate derivatives and incorporated into oligonucleotides by standard procedures.

EXAMPLE 24. Representative Application of the Scheme of FIG. 37.

A.1. 5-Iodo-3',5'-diacetyl-$N^4$-(2-mercaptophenyl)-2'-deoxycytidine

To a solution of 3',5'-diacetyl-5-iodo-2'-deoxyuridine (2.19 g, 5.00 mmol) acetonitrile (ACN, 75 ml), triethylamine (TEA, 6.96 ml, 50.0 mmol) and DMAP (0.15 g, 1.25 mmol) was added mesitylsulfonyl chloride (2.19 g, 10.0 mmol). After stirring at ambient temperature for 18h, DBU (2.14 ml, 10.0 mmol) and 2-aminothiophenol was added (2.14 g, 20.0 mmol) and the solution was stirred for 1 h. The reaction mixture was concentrated and the crude product was partitioned between ethyl acetate (EA, 200 ml) and saturated aqueous sodium bicarbonate (SASB, 200 ml). The organic layer was dried ($Na_2SO_4$) and concentrated on the rotary evaporator. The crude product was purified by flash chromatography on silica gel [1–5% 2-propanol/dichloromethane (DCM)] to deliver the product. $^1H$ NMR ($CDCl_3$) δ2.10 (s, 3H), 2.15 (m, 1H, 2.17 (s, 3H, 2.77 (ddd, 1H, J=2.2, 5.2, 15.1 Hz), 4.14 (bs, 1H), 4.35 (m, 3H), 5.20 (m, 1H), 6.13 (t, 1H, J=6.5 Hz), 6.78 (m, 2H), 7.30 (m, 2H), 8.05 (s, 1H).

A.2. 5-Bromo-3',5'-diacetyl-$N^4$-(2-hydroxyphenyl)-2'-deoxycytidine

To a solution of 3',5'-diacetyl-5-bromo-2'-deoxyuridine (1.79 g, 5.00 mmol) acetonitrile (ACN, 75 ml), triethylamine (TEA, 6.96 ml, 50.0 mmol) and DMAP (0.15 g, 1.25 mmol) was added mesitylsulfonyl chloride (2.19 g, 10.0 mmol). After stirring at ambient temperature for 1 h, DBU (2.14 ml, 10.0 mmol) and 2-aminophenol were added (2.18 g, 20.0 mmol) and the solution was stirred for 1 h. The reaction mixture was concentrated and the crude product was partitioned between ethyl acetate (EA, 200 ml) and saturated aqueous sodium bicarbonate (SASB, 200 ml). The organic layer was dried ($Na_2SO_4$) and concentrated on the rotary evaporator. The crude product was purified by flash chromatography on silica gel [20–40–60–80–100% EA/Hexanes]. The product fractions were concentrated, and the product was triturated from EA.

B. 2'-Deoxyphenothiazine

A solution of diacetate from Step A (600 mg, 1.10 mmol), potassium tert-butoxide (1.0 M in THF, 2.20 ml, 2.20 mmol) and abs. ethanol (25 ml) was heated at reflux for 0.5 h. The solution was allowed to cool to ambient temperature and treated with acetic acid (0.5 ml). The solution was concentrated; toluene (50 ml) was added, and the solution was again concentrated. The crude product was purified by flash chromatography on silica gel (2–10% Methanol (ME)/DCM) to afford the phenothiazine. $^1H$ NMR ($d_6$DMSO) δ2.02 (m, 1H), 2.11 (m, 1H), 3.56 (dq, 2H, J=3.5, 12.0 Hz), 3.77 (m, 1H), 4.19 (m, 1H), 6.06 (t, 1H, J=6.3 Hz), 6.92 (m, 2H), 7.06 (m, 2H), 7.82 (s, 1H).

These compounds were dimethoxytritylated C and phosphitylated D by standard procedures.

Figure 37:
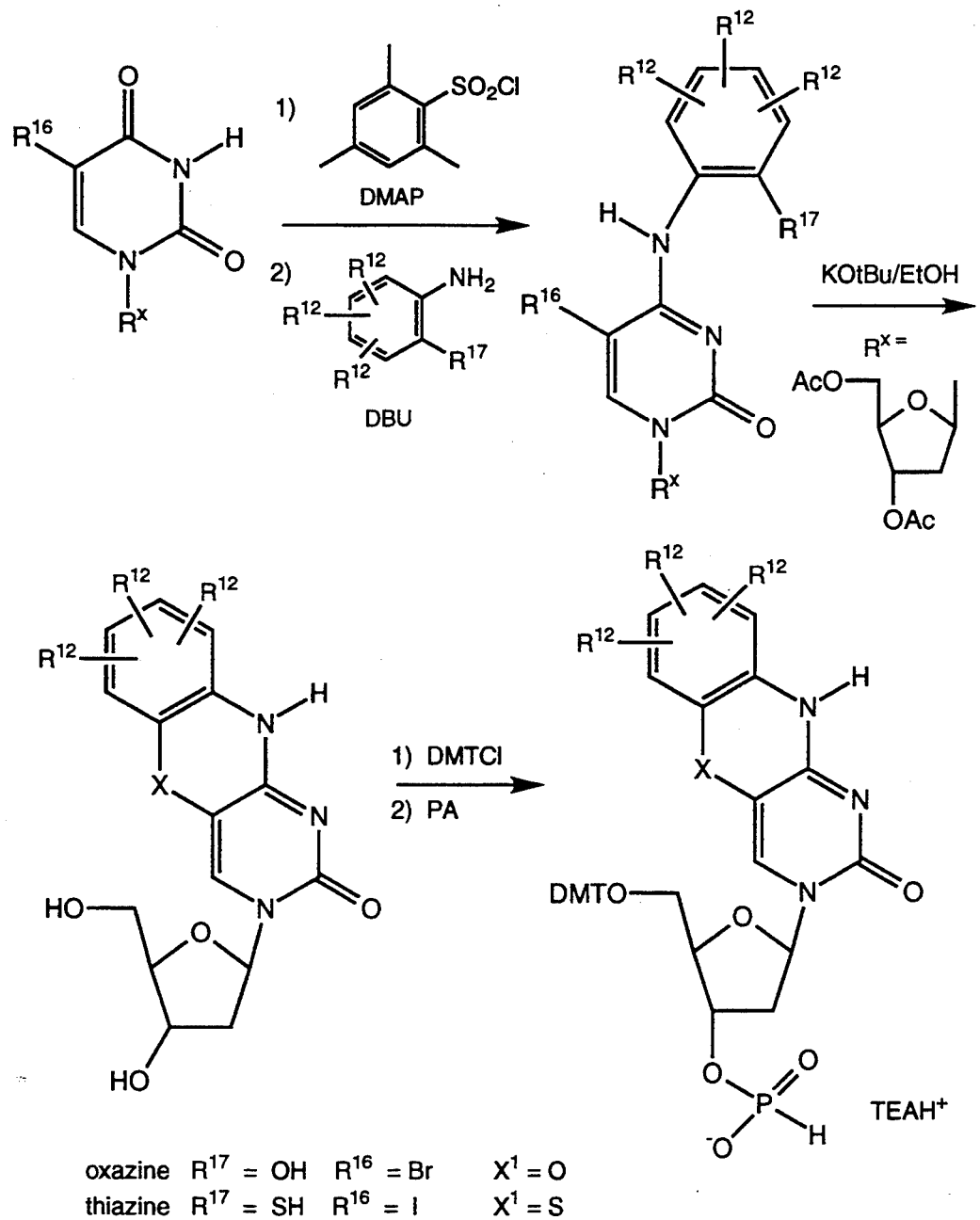

C. 5'-O-DMT-2'-deoxyphenothiazine (from FIG. 37)

$^1H$ NMR ($d_6$ DMSO) δ2.17 (m, 2H), 3.14 (dd, 1H, J=1.6, 9.7 Hz), 3.23 (dd, 1H, J=4.6, 10.4 Hz), 3.74 (s, 6H), 3.91 (m, 1H), 4.26 (m, 1H), 5.31 (d, 1H, J=4.4 Hz), 6.09 (t, 1H, J=6.4 Hz), 6.91 (m, 4H), 7.07 (m, 1H), 7.20–7.41 (m, 12H), 7.59 (s, 1H), 10.46 (s, 1H).

D. 5'-O-DMT-3'-H-phosphonate-2'-deoxyphenothiazine, triethyl ammonium salt $^1H$ NMR (d6 DMSO) δ1.15 (t, 9H, J=7.23 Hz), 2.23 (m, 1H), 2.36 (m, 1H), 3.00 (q, 6H, J=7.2 Hz), 3.15 (dd, 1H, J=2.0, 9.95 Hz), 3.27 (dd, J=4.4, 10.5 Hz), 3.72 (s, 6H), 4.08 (m, 1H), 4.70 (m, 1H), 6.09 (t, 1H, J=6.4 Hz), 6.60 (d, 1H, J=584 Hz), 6.92 (m, 4H), 7.06 (m, 1H), 7.20–7.41 (m, 12H), 7.57 (s, 1H), 10.5 (bs, 1H), 10.6 (bs, 1H). $^{31}$PNMR (d6 DMSO) 0.45 (dd, JA=8.6 Hz, J=$_{P-H}$=584 Hz).

The claims hereafter are to be construed to exclude any subject matter that, at the date of this invention, would not have been patentable under applicable statutory and judicial authority.

---

We claim as our invention:

1. An oligomer comprising at least one substitute linkage between the 3' and 5' or 2' and 5' position of adjacent nucleomonomers, said substitute linkage having the formula 2'—O—CH$_2$—CH=5' or 3'—O—CH$_2$—CH=5' or 3'—S—CH$_2$—CH=5'.

2. The oligomer of claim 1 which is a dimer, trimer or tetramer.

3. The oligomer of claim 1 comprising a detectable label.

4. An oligomer of the formula I or Ia:

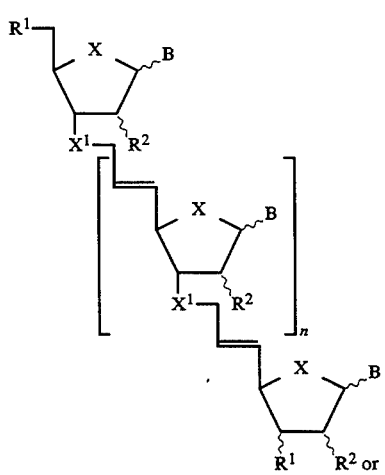

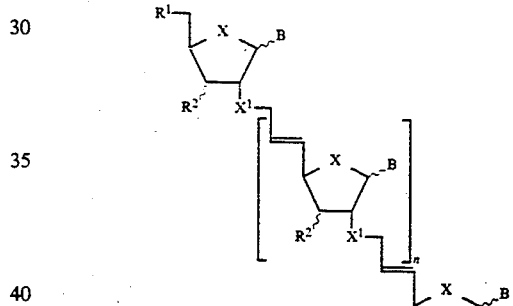

wherein;

X is S, O, CH$_2$, CHF or CF$_2$;

X$^1$ is O or S;

R$^1$ independently is H, OH, an oligomer or a blocking group;

R$^2$ independently is —O—alkyl, —S—alkyl, H, OH, OCH$_3$, SCH$_3$, OCH$_2$CHCH$_2$, OC$_3$H$_7$, SCH$_2$CHCH$_2$, or a halogen;

B is independently a base; and n is 0–100.

5. The oligomer of claim 4 wherein B is independently adenine, guanine, thymine, cytosine, 5-methylcytosine, 5-(1-propynyl)cytosine, 5-(1-propynyl)uracil, 7-deaza-7-methylguanine, 7-deaza-7-methyladenine, 7-deaza-7-(1-propynyl)guanine, 7-deaza-7-(1-propynyl)adenine, phenothiazine tricyclic cytidine, phenoxazine tricyclic cytidine, benzene tricyclic cytidine or 2-pyridine tricyclic cytidine.

6. The oligomer of claim 4 wherein R$^1$ is H-phosphonate, methylphosphonamidite, β-cyanoethylphosphoramidite or alkylphosphoramidite.

7. The oligomer of claim 4 wherein R$^1$ is OH, —PO$_3$, DMTO or MMTO.

8. The oligomer of claim 4 which is a dimer, trimer or tetramer.

9. A nucleic acid complex comprising the oligomer of claim 1 and a nucleic acid molecule having a sequence complementary to the sequence of said oligomer.

* * * * *

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i x ) FEATURE:
        ( A ) NAME/KEY: misc_difference
        ( B ) LOCATION: replace(4, "")
        ( D ) OTHER INFORMATION: /note="This position is Cme
            ( 5 - m e t h y l c y t o s i n e ) with $CH_2$—$CH_2NH$ linkage."

( i x ) FEATURE:
        ( A ) NAME/KEY: misc_difference
        ( B ) LOCATION: replace(6, "")
        ( D ) OTHER INFORMATION: /note="This position is Cme
            ( 5 - m e t h y l c y t o s i n e ) with $CH_2$—$CH_2NH$ linkage."

( i x ) FEATURE:
        ( A ) NAME/KEY: misc_difference
        ( B ) LOCATION: replace(8, "")
        ( D ) OTHER INFORMATION: /note="This position is Cme
            ( 5 - m e t h y l c y t o s i n e ) with $CH_2$—$CH_2$—NH linkage."

( i x ) FEATURE:
        ( A ) NAME/KEY: misc_difference
        ( B ) LOCATION: replace(10, "")
        ( D ) OTHER INFORMATION: /note="This position is Cme
            ( 5 - m e t h y l c y t o s i n e ) with $CH_2$—$CH_2NH$ linkage."

( x i ) SEQUENCE DESCRIPTION: SEQ ID NO:1:

TCTNTNTNTN TTTT                                1 4

( 2 ) INFORMATION FOR SEQ ID NO:2:

( i ) SEQUENCE CHARACTERISTICS:
        ( A ) LENGTH: 14 base pairs (B) TYPE: nucleic acid
(C) STRANDEDNESS: single
(D) TOPOLOGY: linear (ix) FEATURE:
(A) NAME/KEY: misc_difference
(B) LOCATION: replace(4, "")
(D) OTHER INFORMATION: /note="This position is Cme
(5-methylcytosine) with O—CH₂—CH₂NH linkage."

(ix) FEATURE:
(A) NAME/KEY: misc_difference
(B) LOCATION: replace(6, "")
(D) OTHER INFORMATION: /note="This position is Cme
(5-methylcytosine) with O—CH₂—CH₂NH linkage."

(ix) FEATURE:
(A) NAME/KEY: misc_difference
(B) LOCATION: replace(8, "")
(D) OTHER INFORMATION: /note="This position is Cme
(5-methylcytosine) with O—CH₂—CH₂—NH linkage."

(ix) FEATURE:
(A) NAME/KEY: misc_difference
(B) LOCATION: replace(10, "")
(D) OTHER INFORMATION: /note="This position is Cme
(5-methylcytosine) with O—CH₂—CH₂NH linkage."

(xi) SEQUENCE DESCRIPTION: SEQ ID NO:2:

TCTNTNTNTN TTTT 14

(2) INFORMATION FOR SEQ ID NO:3:

(i) SEQUENCE CHARACTERISTICS:
(A) LENGTH: 14 base pairs
(B) TYPE: nucleic acid
(C) STRANDEDNESS: single
(D) TOPOLOGY: linear (ix) FEATURE:
(A) NAME/KEY: misc_difference
(B) LOCATION: replace(6, "")
(D) OTHER INFORMATION: /note="This position is C with
CH₂—CH₂—O linkage."

(ix) FEATURE:
(A) NAME/KEY: misc_difference
(B) LOCATION: replace(8, "")
(D) OTHER INFORMATION: /note="This position is C with
CH₂—CH₂—O linkage."

(xi) SEQUENCE DESCRIPTION: SEQ ID NO:3:

TCTCTCTCTC TTTT 14

(2) INFORMATION FOR SEQ ID NO:4:

(i) SEQUENCE CHARACTERISTICS:
(A) LENGTH: 15 base pairs
(B) TYPE: nucleic acid
(C) STRANDEDNESS: single
(D) TOPOLOGY: linear (ix) FEATURE:
(A) NAME/KEY: misc_difference
(B) LOCATION: replace(2, "")
(D) OTHER INFORMATION: /note="This position is Cm =
5-methyl-2'-deoxycytidine."

(ix) FEATURE:
(A) NAME/KEY: misc_difference
(B) LOCATION: replace(4, "")
(D) OTHER INFORMATION: /note="This position is Cm =
5-methyl-2'-deoxycytidine."

(ix) FEATURE:
(A) NAME/KEY: misc_difference
(B) LOCATION: replace(6, "")
(D) OTHER INFORMATION: /note="This position is Cm =

( i x ) FEATURE:
    ( A ) NAME/KEY: misc_difference
    ( B ) LOCATION: replace(8, "")
    ( D ) OTHER INFORMATION: /note="This position is Cm = 5-methyl-2'-deoxycytidine."

( i x ) FEATURE:
    ( A ) NAME/KEY: misc_difference
    ( B ) LOCATION: replace(10, "")
    ( D ) OTHER INFORMATION: /note="This position is Cm = 5-methyl-2'-deoxycytidine."

( i x ) FEATURE:
    ( A ) NAME/KEY: misc_difference
    ( B ) LOCATION: replace(11, "")
    ( D ) OTHER INFORMATION: /note="This position is T* =a thymidine- thymidine dimer with an experimental linkage of the structure detailed in Table 2."

( i x ) FEATURE:
    ( A ) NAME/KEY: misc_difference
    ( B ) LOCATION: replace(13, "")
    ( D ) OTHER INFORMATION: /note="This position is T* =a thymidine- thymidine dimer with an experimental linkage of the structure detailed in Table 2."

( x i ) SEQUENCE DESCRIPTION: SEQ ID NO:4:

TNTNTNTNTN TTTTT     15

( 2 ) INFORMATION FOR SEQ ID NO:5:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

AGAGAGAGAG AAAAA     15

( 2 ) INFORMATION FOR SEQ ID NO:6:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

TTTTTCTCTC TCTCT     15

( 2 ) INFORMATION FOR SEQ ID NO:7:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

AAAAAGAGAG AGAGA     15

( 2 ) INFORMATION FOR SEQ ID NO:8:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:8:

AAAAAGAGAG AGAGA                                                                    15

( 2 ) INFORMATION FOR SEQ ID NO:9:

( i ) SEQUENCE CHARACTERISTICS:
           ( A ) LENGTH: 15 base pairs
           ( B ) TYPE: nucleic acid
           ( C ) STRANDEDNESS: single
           ( D ) TOPOLOGY: linear ( x i ) SEQUENCE DESCRIPTION: SEQ ID NO:9:

TCTCTCTCTC TTTTT                                                                    15

( 2 ) INFORMATION FOR SEQ ID NO:10:

( i ) SEQUENCE CHARACTERISTICS:
           ( A ) LENGTH: 15 base pairs
           ( B ) TYPE: nucleic acid
           ( C ) STRANDEDNESS: single
           ( D ) TOPOLOGY: linear ( i x ) FEATURE:
           ( A ) NAME/KEY: misc_difference
           ( B ) LOCATION: replace(11, "")
           ( D ) OTHER INFORMATION: /note="This position is thymidine
                with a 3'- allyl ether substitute linkage."

( i x ) FEATURE:
           ( A ) NAME/KEY: misc_difference
           ( B ) LOCATION: replace(12, "")
           ( D ) OTHER INFORMATION: /note="This position is thymidine
                with a 3'- allyl ether substitute linkage."

( x i ) SEQUENCE DESCRIPTION: SEQ ID NO:10:

TCTCTCTCTC TTTTT                                                                    15

( 2 ) INFORMATION FOR SEQ ID NO:11:

( i ) SEQUENCE CHARACTERISTICS:
           ( A ) LENGTH: 15 base pairs
           ( B ) TYPE: nucleic acid
           ( C ) STRANDEDNESS: single
           ( D ) TOPOLOGY: linear ( i x ) FEATURE:
           ( A ) NAME/KEY: misc_difference
           ( B ) LOCATION: replace(11, "")
           ( D ) OTHER INFORMATION: /note="This position is thymidine
                with a 3'- allyl sulfide substitute link..."

( i x ) FEATURE:
           ( A ) NAME/KEY: misc_difference
           ( B ) LOCATION: replace(13, "")
           ( D ) OTHER INFORMATION: /note="This position is thymidine
                with a 3'- allyl sulfide substitute link..."

( x i ) SEQUENCE DESCRIPTION: SEQ ID NO:11:

TCTCTCTCTC TTTTT                                                                    15

( 2 ) INFORMATION FOR SEQ ID NO:12:

( i ) SEQUENCE CHARACTERISTICS:
           ( A ) LENGTH: 15 base pairs
           ( B ) TYPE: nucleic acid
           ( C ) STRANDEDNESS: single
           ( D ) TOPOLOGY: linear ( i x ) FEATURE:
           ( A ) NAME/KEY: misc_difference
           ( B ) LOCATION: replace(11, "")
           ( D ) OTHER INFORMATION: /note="This position is thymidine
                with a 3'- propylether substitute linkage."

( i x ) FEATURE:
           ( A ) NAME/KEY: misc_difference (B) LOCATION: replace(13, "")
(D) OTHER INFORMATION: /note="This position is thymidine with a 3'- propylether substitute linkage."

(xi) SEQUENCE DESCRIPTION: SEQ ID NO:12:

TCTCTCTCTC TTTTT                                                                15

(2) INFORMATION FOR SEQ ID NO:13:

(i) SEQUENCE CHARACTERISTICS:
(A) LENGTH: 15 base pairs
(B) TYPE: nucleic acid
(C) STRANDEDNESS: single
(D) TOPOLOGY: linear (ix) FEATURE:
(A) NAME/KEY: misc_difference
(B) LOCATION: replace(11, "")
(D) OTHER INFORMATION: /note="This position is thymidine with a 3'- propyl sulfide substitute linkage."

(ix) FEATURE:
(A) NAME/KEY: misc_difference
(B) LOCATION: replace(13, "")
(D) OTHER INFORMATION: /note="This position is thymidine with a 3'- propyl sulfide substitute linkage."

(xi) SEQUENCE DESCRIPTION: SEQ ID NO:13:

TCTCTCTCTC TTTTT                                                                15